United States Patent
Xin-Yuan et al.

(10) Patent No.: US 10,690,666 B2
(45) Date of Patent: Jun. 23, 2020

(54) METHODS AND COMPOSITIONS FOR MODULATING $T_H$-GM CELL FUNCTION

(71) Applicant: National University of Singapore, Singapore (SG)

(72) Inventors: Fu Xin-Yuan, Singapore (SG); Wanqiang Sheng, Singapore (SG); Yongliang Zhang, Singapore (SG); Fan Yang, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 188 days.

(21) Appl. No.: 15/514,644

(22) PCT Filed: Sep. 25, 2015

(86) PCT No.: PCT/SG2015/050344
§ 371 (c)(1),
(2) Date: Mar. 27, 2017

(87) PCT Pub. No.: WO2016/048247
PCT Pub. Date: Mar. 31, 2016

(65) Prior Publication Data
US 2017/0219581 A1 Aug. 3, 2017

(30) Foreign Application Priority Data

Sep. 26, 2014 (SG) .......................... 10201406130P

(51) Int. Cl.
*G01N 33/564* (2006.01)
*C12Q 1/6883* (2018.01)
*C12N 5/0783* (2010.01)
*A61K 39/00* (2006.01)
*A61K 31/4433* (2006.01)
*G01N 33/68* (2006.01)

(52) U.S. Cl.
CPC ....... *G01N 33/564* (2013.01); *A61K 31/4433* (2013.01); *A61K 39/0008* (2013.01); *C12N 5/0636* (2013.01); *C12N 5/0637* (2013.01); *C12Q 1/6883* (2013.01); *G01N 33/6863* (2013.01); *G01N 33/6869* (2013.01); *C12N 2501/2307* (2013.01); *C12N 2501/24* (2013.01); *C12N 2501/51* (2013.01); *C12N 2501/515* (2013.01); *C12N 2501/60* (2013.01); *C12N 2501/727* (2013.01); *C12Q 2600/118* (2013.01); *C12Q 2600/158* (2013.01); *G01N 2333/4706* (2013.01); *G01N 2333/535* (2013.01); *G01N 2333/5403* (2013.01); *G01N 2333/5418* (2013.01); *G01N 2800/102* (2013.01); *G01N 2800/285* (2013.01)

(58) Field of Classification Search
None
See application file for complete search history.

(56) References Cited

FOREIGN PATENT DOCUMENTS

| EP | 2669295 | 12/2013 |
|---|---|---|
| WO | 2005/029091 | 3/2005 |
| WO | 2007/137405 | 12/2007 |
| WO | 2010/063488 | 6/2010 |

OTHER PUBLICATIONS

"Bhlhe40 controls cytokine production by T cells and is essential for pathogenicity in autoimmune neuroinflamation" to Lin et al. published Apr. 3, 2014.
Provisional Opinion Accompanying the Partial Search Result for EP Application No. 15843971.1 dated Feb. 3, 2018.
Noster, R. et al "IL-17 and GM-CSF Expression Are Antagonistically Regulated by Human T Helper Cells" Science Translational Medicine (2014) vol. 6, issue 241, published online Jun. 2014.
Zhang, J. et al "A novel subset of helper T cells promotes immune responses by secreting GM-CSF" Cell Death and Differentiation (2013) vol. 20, pp. 1731-1741.
Prystowksy, M.B. et al "Alloreactive cloned T cel lines. VI. Multiple lymphokine activities secreted by helper and cytolytic cloned T lymphocytes" The Journal of Immunology (1982) vol. 129, pp. 2337-2344.
Wurster, A.L. et al "NF-κB and BRG1 bind a distal regulatory element in the IL-3/GM-CSF locus" Molecular Immunology (2011) vol. 48, pp. 2178-2188.
Miklossy et al "Terapeutic modulaators of STAT signalling for human diseases" Nature Reviews Drug Discovery (2013) col. 12, pp. 611-629.
Sheng, W. et al "STAT5 programs a distinct subset of GM-CSF-producing T helper cells that is essential for autoimmune neuroinflammation" Cell Research, (2014), vol. 24, pp. 1387-1402 published online Nov. 21, 2014.
Hartmann, F.J. et al "Multiple sclerosis-associated IL2RA polymorphism controls GM-CSF production in human TH cells" Nature Communications (2014), vol. 5, pp. 5056 published online Oct. 3, 2014.
O'Shea et a. "Mechanisms Underlying Lineage Commitment and Plasticity of Helper CD4+ T Cells" Science, Feb. 26, 2010.
Littman et al. "Th17 and Regulatory T cells in Mediating and Restraining Inflammation" Cell, Mar. 19, 2010.

(Continued)

*Primary Examiner* — Daniel E Kolker
*Assistant Examiner* — Jegatheesan Seharaseyon
(74) *Attorney, Agent, or Firm* — Foley & Lardner LLP

(57) ABSTRACT

Disclosed herein is a T-helper cell ("$T_H$-GM" cell) that is regulated by IL-7/STAT5 and which secrete GM-CSF/IL-3. Also disclosed are methods and compositions for modulating $T_H$-GM function for the treatment of, e.g., inflammatory disorders. Diagnostic and prognostic methods for specifically identifying $T_H$-GM-mediated inflammatory disorders (e.g., rheumatoid arthritis), as distinct from and/or in addition to non-$T_H$-GM-mediated (e.g., TNF-α-mediated) inflammatory disorders, are also provided.

11 Claims, 38 Drawing Sheets

(56) References Cited

OTHER PUBLICATIONS

Dong, Chen. "TH17 cells in development: an updated view of their molecular identity and genetic programming" Nature Reviews Immunology, May 2008.
Thierfelder et al. "Requirement for Stat4 in interleukin-12-mediated responses of natural killer and T cells" Nature, Jul. 11, 1996.
Szabo et al. "A Novel Transcription Factor, T-bet, Directs Th1 Lineage Commitment" Cell, Mar. 17, 2000.
Harris et al. "Cutting Edge: An In Vivo Requirement for STAT3 Signaling in TH17 Development and TH17 Dependent Autoimmunity" The Journal of Immunology, Apr. 17, 2017.
Zhu et al. "CD4T cells: fates, functions, and faults" Blood, Sep. 1, 2008.
Becher et al. "TH17 cytokines in autoimmune neuro-inflammation" Current Opinion in Immunology, Sep. 9, 2011.
Joan Goverman. "Autoimmune T cell responses in the central nervous system" Nature Reviews Immunology, May 15, 2009.
Becher et al. "Experimental autoimmune encephalitis and inflammation in the absence of interleukin-12" The Journal of Clinical Investigation, Aug. 2002.
Chu et al. "Failure to Suppress the Expansion of the Activated CD4T Cell Population in Interferon gamma-deficient Mice Leads to Exacerbation of Experimental Autoimmune Encephalomyelitis" J. Exp. Med., Jul. 3, 2000.
Kreymborg et al "IL-22 is Expressed by TH17 Cells in an IL-23 Dependent Fashion, but Not Required for the Development of Autoimmune Encephalomyelitis" The Journal of Immunology, 2007.
Yao et al. "Nonredundant roles for Stat5a/b in directly regulating Foxp3" Blood, May 15, 2007.
Cui et al. "Inactivation of Stat5 in Mous Mammary Epithelium during Pregnancy Reveals Distinct Functions in Cell Proliferation, Survival, and Differentiation" Molecular and Cellular Biology, Jan. 14, 2004.
Sporici et al. "CXCR3 blockade inhibits T-cell migration into the CNS during EAE and prevents development of adoptively transferred, but not actively induced, disease" Eur. J. Immunol., 2010.
Mirabella et al. "The Human IL-3/Granulocyte-Macrophage Colony-Stimulating Factor Locus Is Epigenetically Silent in Immature Thymocytes and Is Progressively Activated during T Cell Development" The Journal of Immunology, 2010.
Durant et al. "Diverse Targets of the Transcription Factor STAT3 Contribute to T Cell Pathogenicity and Homeostasis" Immunity, May 28, 2010.
Zhu et al. "Differentiation of Effector CD4 T Cell Populations" Annual Review of Immunology, Jan. 4, 2010.
Noster et al. "IL-17 and GM-CSF Expression Are Antagonistically Regulated by Human T Helper Cells" Science Translational Medicine, Jun. 18, 2014.
Chen et al. "Histone Dynamics on the Interleukin-2 Gene in Response to T-Cell Activation" Molecular and Cellular Biology, Apr. 2005.
Thomas Malek. "The Biology of Interleukin-2" Annual Review of Immunology, Dec. 6, 2007.
Rochman et al. "New insights into the regulation of T cells by gamma-c family cytokines" Nature Reviews Immunology, Jul. 2009.
Ariello et al. "IL-7 Induces Myelopoiesis and Erythropoiesis" The Journal of Immunology, 2007.
Lee et al. "IL-7 Promotes TH1 Development and Serum IL-7 Predicts Clinical Response to Interferon-beta in Multiple Sclerosis" Science Translational Medicine, Jul. 27, 2011.
Welte et al. "STAT3 deletion during hematopoiesis causes Crohn's disease-like pathogenesis and lethality: A critical role of STAT3 in innate immunity" Proc Ntal Acad Sci, Nov. 22, 2002.
Zhang et al. "MKP-1 Is Necessary for T Cell Activation and Function" The Journal of Biological Chemistry, Nov. 6, 2009.
Uhlig et al. "Differential Activity of IL-12 and IL-23 in Mucosal and Systemic Innate Immune Pathology" Immunity 25, Aug. 2006.
Afkarian et al. "T-bet is a STATl-induced regulator of IL-12R expression in Naïve CD4+T cells" Nature Immunology, Jun. 2002.
Ansel et al. "Regulation of TH2 Differentiation and Il4 Locus Accessibility" Annual Review of Immunology, 2006.
Baron et al. "Surface Expression of alpha-4 Integrin by CD4 T Cells Is Required for Their Entry into Brain Parenchyma" J. Exp. Med., Jan. 1, 1993.
Bell et al. "Measurement of colony-stimulating factors in synovial fluid: potential clinical value" Rheumatol Int, Aug. 19, 1994.
Berner et al. "Analysis of Th1 and Th2 Cytokines Expressing CD4+ and CD8+ T Cells in Rheumatoid Arthritis by Flow Cytometry" The Journal of Rheumatology, 2000.
Bettelli et al. "Reciprocal developmental pathways for the generation of pathogenic effector TH17 and regulatory T cells" Nature, 2006.
Brustle et al. "The development of inflammatory TH-17 cells requires interferon-regulatory factor 4" Nature Immunology, Aug. 5, 2007.
Burchill et al. "IL-2 Receptor Beta-Dependent STAT5 Activation Is Required for the Development of Foxp3+ Regulatory T Cells" The Journal of Immunology, 2007.
Campbell et al. "Protection from Collagen-Induced Arthritis in Granulocyte-Macrophage Colony-Stimulating Factor-Deficient Mice" The Journal of Immunology, 1998.
Campbell et al. "Differentiation of Inflammatory Dendritic Cells is Mediated by NF-kappaB1-Dependent GM-CSF Production in CD4 T Cells" The Journal of Immunology, 2011.
Choy et al. "Cytokine Pathways and Joint Inflammation in Rheumatoid Arthritis" Mechanisms of Disease, Mar. 22, 2001.
Codarri et al. "RORgammaT drives production of the cytokine GM-CSF in helper T cells, which is essential for the effector phase of autoimmune neuroinflammation" Nature Immunology, Jun. 2011.
Cook et al. "Blockade of collagen-induced arthritis post-onset by antibody to granulocyte-macrophage colony-stimulating factor (GM-CSF): requirement for GM-CSF in the effector phase of disease" Arthritis Res, 2001.
Cope et al. "The central role of T cells in rheumatoid arthritis" Clinical and Experimental Rheumatology, 2007.
Cornish et al. "G-CSF and GM-CSF as therapeutic targets in rheumatoid arthritis" Nature Reviews Rheumatol, Oct. 2009.
Croxford et al. "IL-23: One cytokine in control of autoimmunity" European Journal of Immunology, 2012.
Cua et al. "Interleukin-23 rather than interleukin-12 is the critical cytokine for autoimmune inflammation of the brain" Nature, 2003.
El-Behi et al. "The encephalitogenicity of TH17 cells is dependent on IL-1- and IL-23-induced production of the cytokine GM-CSF" Nature Immunology, 2011.
Gran et al. "IL-12p35-Deficient Mice Are Susceptible to Experimental Autoimmune Encephalomyelitis: Evidence for Redundancy in the IL-12 System in the Induction of Central Nervous System Autoimmune Demyelination" The Journal of Immunology, 2002.
Gregory et al. "Interleukin 7 receptor alpha chain (IL7R) shows allelic and functional association with multiple sclerosis" Nature Genetics, Sep. 2007.
Greter et al. "GM-CSF Controls Nonlymphoid Tissue Dendritic Cell Homeostasis but Is Dispensable for the Differentiation of Inflammatory Dendritic Cells" Immunity, Jun. 29, 2012.
Guedez et al. "Genetic Ablation of Interferon-gamma Up-Regulates Interleukin-1beta Expression and Enables the Elicitation of Collagen-Induced Arthritis in a Nonsusceptible Mouse Strain" Arthritis & Rheumatism, Oct. 2001.
Gutcher et al. "APC-derived cytokines and T cell polarization in autoimmune inflammation" The Journal of Clinical Investigation, May 2007.
Haak et al. "IL-17A and IL-17F do not contribute vitally to autoimmune neuro-inflammation in mice" The Journal of Clinical Investigation, 2009.
John Hamilton. "Colony-stimulating factors in inflammation and autoimmunity" Nature Reviews Immunology, Jul. 2008.
Harrington et al. "Interleukin 17-producing CD4+ effector T cells develop via a lineage distinct from the T helper type 1 and 2 lineages" Nature Immunology, Nov. 2005.

(56) References Cited

OTHER PUBLICATIONS

Hofstetter et al. "Therapeutic efficacy of IL-17 neutralization in murine experimental autoimmune encephalomyelitis" Cellular Immunology, Dec. 28, 2005.
Irmler et al. "Exacerbation of Antigen-Induced Arthritis in IFN-gamma-Deficient Mice as a Result of Unrestricted IL-17 Response" The Journal of Immunology, 2007.
Ivanov et al. "The Orphan Nuclear Receptor RORgammaT Directs the Differentiation Program of Proinflammatory IL-17+ T Helper Cells" Cell, Sep. 22, 2006.
Kaplan et al. "Stat6 Is Required for Mediating Responses to IL-4 and for the Development of Th2 Cells" Immunity, Mar. 1996.
Kaplan et al. "Impaired IL-12 responses and enhanced development of Th2 cells in Stat4-deficient mice" Nature, Jul. 11, 1996.
Kolaczkowska et al. "Neutrophil recruitment and function in health and inflammation" Nature Reviews Immunology, Mar. 2013.
Komatsu et al. "Autoimmune Arthritis: The Interface Between the Immune System and Joints" Advances in Immunology, 2012.
Korn et al. "IL-21 initiates an alternative pathway to induce proinflammatory TH17 cells" Nature, 2007.
Langrish et al. "IL-23 drives a pathogenic T cell population that induces autoimmune inflammation" The Journal of Experimental Medicine, Jan. 17, 2005.
Laurence et al. "Interleukin-2 Signaling via STAT5 Constrains T Helper 17 Cell Generation" Cell, Mar. 2007.
Lawlor et al. "Acute CD4+ T Lymphocyte-Dependent Interleukin-1-Driven Arthritis Selectively Requires Interleukin-2 and Interleukin-4, Joint Macrophages, Granulocyte-Macrophage Colony-Stimulating Factor, Interleukin-6, and Leukemia Inhibitory Factor" Arthritis & Rheumatism, Dec. 2005.
Lee et al. "Anti-IL-7 receptor-alpha reverses established type 1 diabetes in nonobese diabetic mice by modulating effector T-cell function" PNAS, Jul. 31, 2012.
Leonard et al. "Prevention of Experimental Autoimmune Encephalomyelitis by Antibodies Against Interleukin 12" The Journal of Experimental Medicine, Jan. 1, 1995.
Lighvani et al. "T-bet is rapidly induced by interferon-gamma in lymphoid and myeloid cells" PNAS, Dec. 18, 2001.
Liu et al. "Loss of STAT3 in CD4+ T Cells Prevents Development of Experimental Autoimmune Diseases" The Journal of Immunology, 2008.
Lock et al. "Gene-microarray analysis of multiple sclerosis lesions yields new targets validated in autoimmune encephalomyelitis" Nature Medicine, May 2002.
Okada et al. "Genetics of rheumatoid arthritis contributes to biology and drug discovery" Nature, Feb. 20, 2014.
Lundmark et al. "Variation in interleukin 7 receptor alpha chain (IL7R) influences risk of multiple sclerosis" Nature Genetics, Jul. 29, 2007.
Manoury-Schwartz et al. "High susceptibility to collagen-induced arthritis in mice lacking IFN-gamma receptors." The Journal of Immunology, 1997.
McGeachy et al. "The interleukin 23 receptor is essential for the terminal differentiation of interleukin 17-producing effector T helper cells in vivo" Nature Immunology, Feb. 1, 2009.
McInnes et al. "Cytokines in the pathogenesis of rheumatoid arthritis" Nature Reviews Immunology, Jun. 2007.
McInnes et al. "The Pathogenesis of Rheumatoid Arthritis" The New England Journal of Medicine, Dec. 8, 2011.
Muller-Ladner et al. "Cells of the synovium in rheumatoid arthritis synovial fibroblasts" Arthritis Research & Therapy, Dec. 20, 2007.
Muller et al. "Discovery of Chromone-Based Inhibitors of the Transcription Factor STAT5" ChemBioChem, 2008.
Nurieva et al. "Essential autocrine regulation by IL-21 in the generation of inflammatory T cells" Nature, Jul. 26, 2007.
A. B. Pernis "Th17 cells in rheumatoid arthritis and systemic lupus erythematosus" Journal of Internal Medicine, 2009.
Plater-Zyberk et al. "GM-CSF neutralization suppresses inflammation and protects cartilage in acute streptococcal cell wall arthritis of mice" Ann Rheum Dis, Oct. 4, 2006.
Ponomarev et al. "GM-CSF Production by Autoreactive T Cells Is Required for the Activation of Microglial Cells and the Onset of Experimental Autoimmune Encephalomyelitis" The Journal of Immunology, 2007.
Reboldi et al. "C-C chemokine receptor 6-regulated entry of TH-17 cells into the CNS through the choroid plexus is required for the initiation of EAE" Nature Immunology, May 2009.
Segal et al. "IL-12 Unmasks Latent Autoimmune Disease in Resistant Mice" The Journal of Experimental Medicine, Aug. 1, 1996.
Shimoda et al. "Lack of IL-4-induced Th2 response and IgE class switching in mice with disrupted Stat6 gene" Nature, Apr. 18, 1996.
Sonderegger et al. "GM-CSF mediates autoimmunity by enhancing IL—dependent Th17 cell development and survival" The Journal of Experimental Medicine, Sep. 8, 2008.
Lawrence Steinman. "A brief history of TH17, the first major revision in the TH1/TH2 hypothesis of T cell-mediated tissue damage" Nature Medicine, Feb. 6, 2007.
Stritesky et al. "IL-23 Promotes Maintenance by not Commitment to the TH17 Lineage" The Journal of Immunology, 2008.
Szabo et al. "Distinct Effects of T-bet in TH1 Lineage Commitment and IFN-gamma Production in CD4 and CD8 T Cells" Science, 2002.
Takeda et al. "Essential role of Stat6 in IL-4 signalling" Nature, Apr. 18, 1996.
Veldhoen et al. "The aryl hydrocarbon receptor links TH17-cell-mediated autoimmunity to environmental toxins" Nature, May 2008.
Veldhoen et al. "TGFbeta in the Context of an Inflammatory Cytokine Milieu Supports De Novo Differentiation of IL-17-Producing T Cells" Immunity, Feb. 2006.
Vermeire et al. "Accelerated collagen-induced arthritis in IFN-gamma receptor-deficient mice." The Journal of Immunology, 1997.
Willenborg et al. "IFN-gamma Plays a Critical Down-Regulatory Role in the Induction and Effector Phase of Myelin Oligodendrocyte Glycoprotein-Induced Autoimmune Encephalomyelitis" Cutting Edge, Aug. 19, 1996.
Wright et al. "The multifactorial role of neutrophils in rheumatoid arthritis" Nature Reviews Rheumatology, Oct. 2014.
Yamada et al. "Th1 but not Th17 cells predominate in the joints of patients with rheumatoid arthritis" Ann Rheum Dis, 2008.
Yang et al. "STAT3 Regulates Cytokine-mediated Generation of Inflammatory Helper T Cells" The Journal of Biological Chemistry, Mar. 30, 2007.
Yang et al. "T Helper 17 Lineage Differentiation is Programmed by Orphan Nuclear Receptors RORalpha and RORgamma" Immunity, Jan. 2008.
Yang et al. "Opposing regulation of the locus encoding IL-17 through direct, reciprocal actions of STAT3 and STAT5" Nature Immunology, Jan. 30, 2011.
Yang et al. "Identification of a distant T-bet enhancer responsive to IL-12/Stat4 and IFNgamma/Stat1 signals" Blood, Jun. 15, 2007.
Yang et al. "Dependence of Interleukin-1-Induced Arthritis on Granulocyte-Macrophage Colony-Stimulating Factor" Arthritis & Rheumatism, Jan. 2001.
Yao et al. "Stata/b are essential for normal lymphoid development and differentiation" PNAS, Jan. 24, 2006.
Zhang et al. "Induction of Experimental Autoimmune Encephalomyelitis in IL-12 Receptor-beta 2-Deficient Mice: IL-12 Responsiveness Is Not Required in the Pathogenesis of Inflammatory Demyelination in the Central Nervous System" The Journal of Immunology, 2003.
Zhou et al. "IL-6 programs TH-17 cell differentiation by promoting sequential engagement of the IL-21 and IL-23 pathways" Nature Immunology, Sep. 2007.
Zhu et al. "Peripheral CD4+ T-cell differentiation regulated by networks of cytokines and transcription factors" Immunological Reviews, 2010.
International Search Report and Written Opinion for PCT/SG2015/050344, dated Sep. 25, 2015.
Search Report for Singapore Application No. 11201702475V.
Extended European Search Report for Application No. 15843971.1 dated Jul. 10, 2018.

(56) References Cited

OTHER PUBLICATIONS

"Persepectives of the relationship between Il-7 and autoimmune diseases." Xiao-Song Wang et al. Clinical rheumatology vol. 32, No. 12, Aug. 11, 2013, pp. 1703-1709.

"Bhlhe40 controls cytokine production by T cells and is essential for pathogenicity in autoimmune neuroinflamation" Chih-Chung Lin et al. Nature communications vol. 5, Apr. 3, 2014.

"Circulating Cytokine Profiles and Their Relationships with Autoantibodies, Acute Phase Reactants, and Disease Activity in Patients with Rheumatoid Arthritis" Pieter W.A. Meyer et al. Mediators of Inflammation vol. 2010, Jan. 1, 2010, pp. 1-10.

"Interleukin-12 (IL-12), but not IL-23, induces the expression of IL-7 in microglia and macrophages: implications for multiple sclerosis" Malabendu Jana et al. Immunology vol. 141, No. 3, Mar. 11, 2013, pp. 549-563.

"Expression of GM-CSF in T Cells Is Increased in Multiple Sclerosis and Suppressed by IFN-b Therapy" The Journal of Immunology, vol. 194, No. 11, Apr. 27, 2015, pp. 5085-5093.

"Transcriptional Analysis of Multiple Sclerosis Brain Lesions Reveals a Complex Pattern of Cytokine Expression" S.E. Baranzini et al. The Hournal of Immunology vol. 165, No. 11, Dec. 1, 2000, pp. 6576-6582.

"Results of a phase I study in patients suffering from secondary-progressive multiple sclerosis demonstrating the safety of the amino acid copolymer PI-2301 and a possible induction of a anti inflammatory cytokine response" Kovalchin J. et al. Journal of Neuroimmunology, vol. 225, No. 1-2, Aug. 25, 2010, pp. 156-163.

Office Action issued in corresponding Japanese Patent Application No. 2017-516733 dated Sep. 3, 2019.

Wang, H. et al., "The molecular mechanism of curcumol on inducing cell growth arrest and apoptosis in Jurkat cels, a model of CD4 $T^+$ cells" International Immunopharmacology, May 2014, vol. 21, p. 375-382.

Steidl, S. et al., "In vitro affinity maturation of human GM-CSF antibodies by targeted CDR-diversification" Molecular Immunology, 2008, vol. 46, p. 135-144.

Zhu, T. et al. "THU0256 Pharmacodynamics of ASP015K, A Novel Janus Kinase Inhibitor, in Healthy Volunteers", Ann Rheum Dis,2013,vol. 72, Suppl.3, col. THU0256.

Pongratz, G. et al., "IL-7 receptor α expressing B cells act proinflammatory in collagen-induced arthritis and are inhibited by sumpathetic neurotransmitters" Ann Rheum Dis, Jan. 2014, vol. 73, p. 306-312.

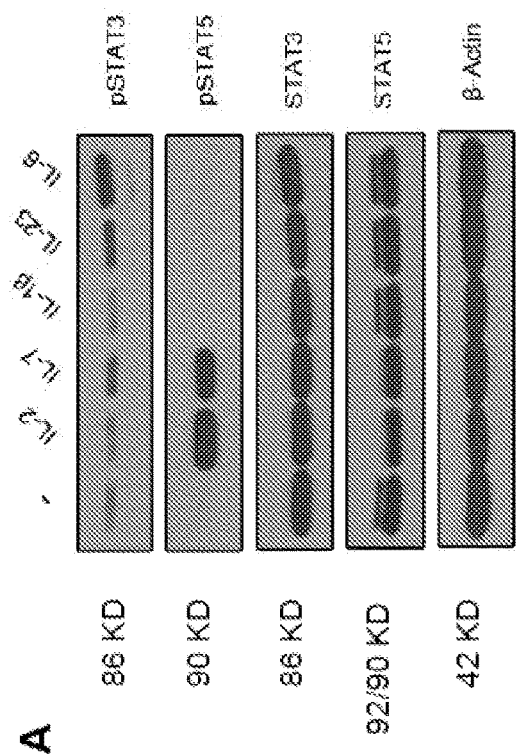
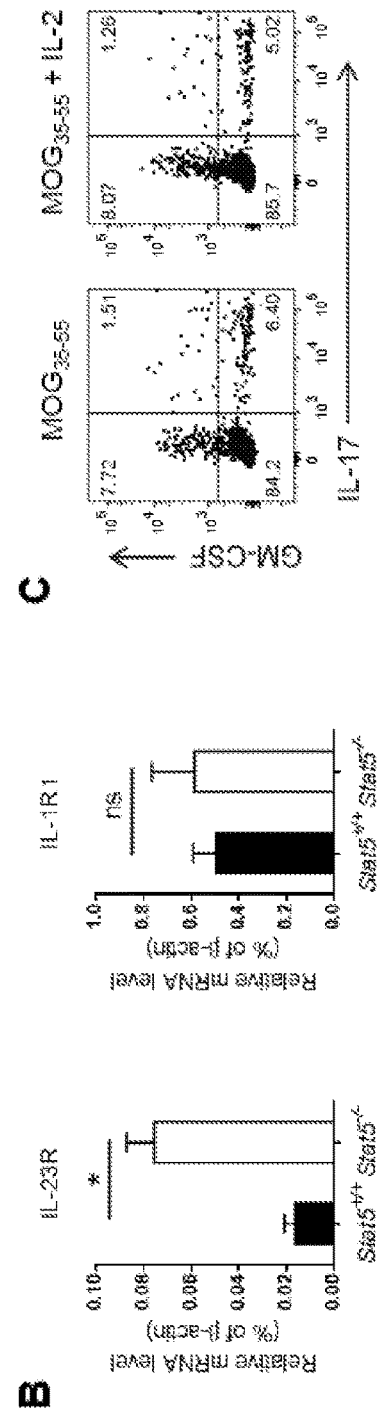
FIGS. 10A-10C

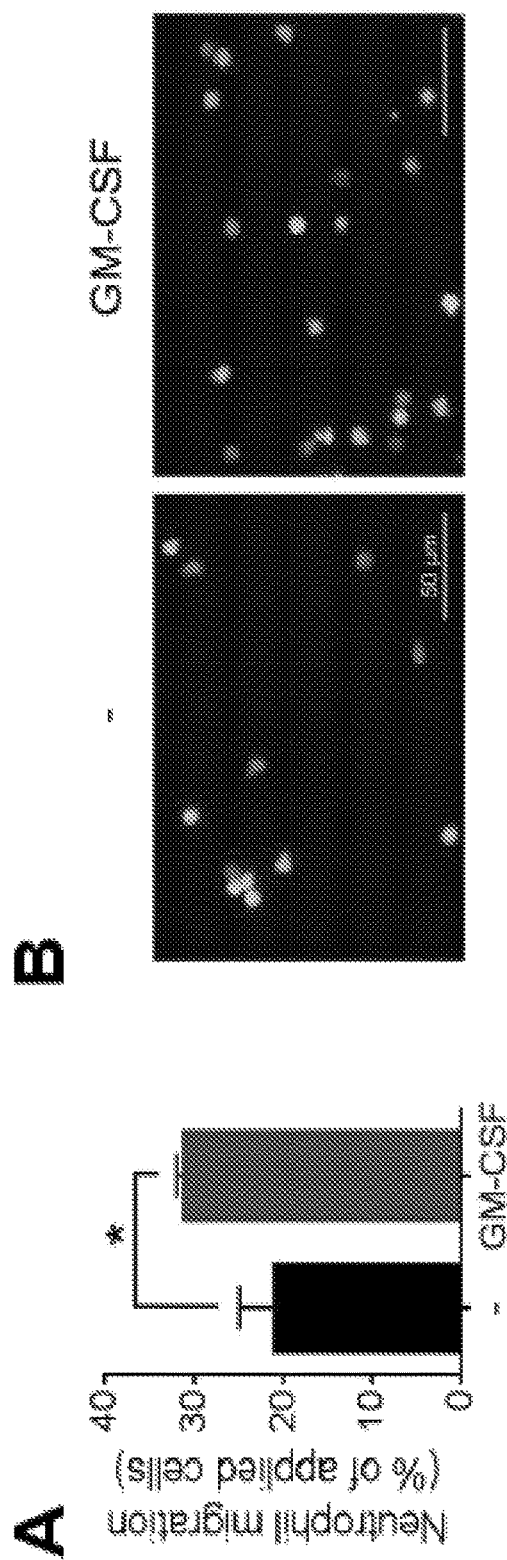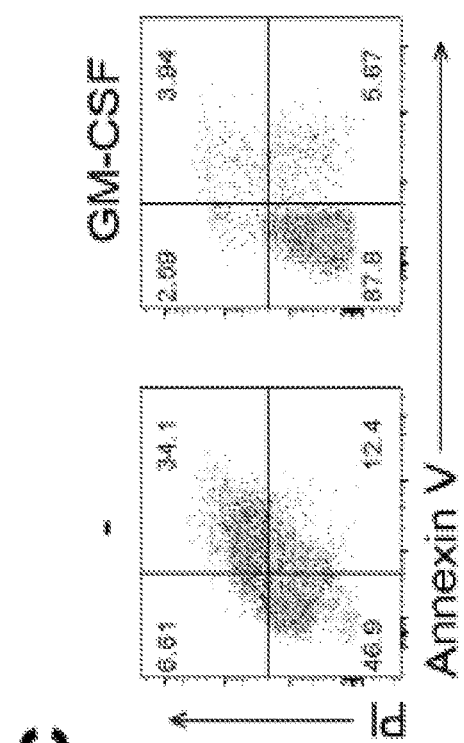
FIGS. 33A-33C

METHODS AND COMPOSITIONS FOR MODULATING $T_H$-GM CELL FUNCTION

RELATED APPLICATION

This application claims the benefit of Singapore Patent Application No. 10201406130P, filed Sep. 26, 2014. The entire teachings of the above application are incorporated herein by reference.

BACKGROUND OF THE INVENTION

A significant body of research has led to the current model of immunity and inflammation, as well as the dysregulation in immune and inflammatory disorders. It is currently understood that CD4$^+$ helper T ($T_H$) cells play a crucial role in host defense against various pathogens by orchestrating adaptive and innate immune responses. Upon T-cell receptor (TCR) activation by cognate antigen, naïve CD4$^+$ T cells are committed to differentiate into at least five major subsets: $T_H1$, $T_H2$, $T_H17$, $iT_{reg}$ and $T_{FH}$, which are modulated by cytokine milieus. $T_H1$ and $T_H17$ cells are known to be the primary effectors of inflammation. However, the pathogenic roles of either $T_H1$ or $T_H17$ in various inflammatory disorders remain unclear. For example, recent studies conflict with previously understood paradigm of $T_H17$ in multiple sclerosis (MS) pathogenicity (Haak et al., 2009), making it more challenging to identify potential drug targets for MS therapy. Similarly, while rheumatoid arthritis (RA) is traditionally understood to be a disorder mediated by tumor necrosis factor α (TNF-α), up to 40% of RA patients fail to respond to anti-TNF-α treatment.

Accordingly, there remains a significant unmet need for effective treatment methods for autoimmune and inflammatory disorders such as, e.g., MS and RA.

SUMMARY OF THE INVENTION

The present disclosure relates, in part, to the identification of an interleukin-7 (IL-7)/signal transducer and activator of transcription 5 (STAT5)-regulated granulocyte macrophage colony-stimulating factor (GM-CSF)/IL-3-producing $T_H$ cells, termed $T_H$-GM, which represent a distinct helper T cell subset with unique developmental and functional characteristics. Identified herein is an inflammatory pathway mediated by $T_H$-GM cells ($T_H$-GM-mediated inflammatory pathway), which represents an independent inflammatory pathway apart from known non-$T_H$-GM-mediated inflammatory pathways (e.g., TNF-a, IL-6, and IL-1b pathways of inflammation). The present disclosure provides methods and compositions for diagnosing inflammatory disorders that are $T_H$-GM-mediated, and modulating $T_H$-GM cell function for the treatment of inflammatory disorders mediated by the $T_H$-GM pathway.

Accordingly, in one aspect, the present disclosure provides a method of diagnosing a $T_H$-GM-mediated inflammatory disorder in a patient suffering from an inflammatory disorder, comprising: a) contacting a sample collected from a patient suffering from an inflammatory disorder with a detecting agent that detects a polypeptide or nucleic acid level of STAT5 (e.g., phospho-STAT5 (Tyr694)), IL-7, GM-CSF or IL-3, or a combination thereof; and b) quantifying the polypeptide or nucleic acid level of STAT5 (e.g., phospho-STAT5 (Tyr694)), IL-7, GM-CSF or IL-3, or a combination thereof, wherein an increased level of STAT5 (e.g., phospho-STAT5 (Tyr694)), interleukin-7 (IL-7), GM-CSF or interleukin-3 (IL-3), or a combination thereof relative to a reference level indicates that the patient suffers from a $T_H$-GM-mediated inflammatory disorder.

In another aspect, the present disclosure provides an isolated population of GM-CSF-secreting T-helper cells ($T_H$-GM), wherein the $T_H$-GM cells are differentiated from cluster of differentiation 4 (CD4+) precursor cells in the presence of IL-7 and activated STAT5, and wherein the $T_H$-GM cells express GM-CSF and IL-3.

In another aspect, the present disclosure provides a method of modulating $T_H$-GM function, comprising contacting the $T_H$-GM, or CD4+ precursor cells, or both, with a modulating agent that modulates $T_H$-GM function.

In some aspects, the present disclosure provides a method of treating a $T_H$-GM-mediated inflammatory disorder in a patient in need thereof, comprising administering to said patient an effective amount of a modulating agent that modulates $T_H$-GM cell function.

In other aspects, the present disclosure provides a method of treating rheumatoid arthritis in a patient who exhibits limited response to anti-tumor necrosis factor alpha (TNF-α) therapy, comprising administering to said patient an effective amount of a modulating agent that modulates $T_H$-GM function.

In another aspect, the present disclosure provides a method of treating a STAT5-mediated inflammatory disorder in a patient in need thereof, comprising administering to the patient an effective amount of an agent that modulates STAT5 function.

In further aspects, the present disclosure provides a method of screening to identify a modulator of $T_H$-GM cell function, comprising contacting an isolated population of $T_H$-GM cells, or an isolated population of CD4+ precursor cells, with a candidate agent, and determining a readout of $T_H$-GM function in the presence or absence of the candidate agent, wherein a change in the readout of $T_H$-GM function indicates that the candidate agent is a modulator of $T_H$-GM function.

The present disclosure enables the identification or classification between inflammatory disorders that are either primarily $T_H$-GM-mediated, or primarily non-$T_H$-GM-mediated (e.g., mediated by TNF-α, IL-6, and/or IL-1β), or both. Thus, using the methods described herein, it is possible to determine whether a patient suffering from, e.g., RA, suffers from an RA that is primarily $T_H$-GM-mediated, or primarily non-$T_H$-GM-mediated, or both. This differentiation allows for a more targeted and tailored method of treating inflammatory disorders such as RA, for which current treatments are only 40% effective. Further, the present disclosure provides methods and compositions for prognosing the progression of an inflammatory disorder so as to tailor the treatment according to the stage of the disease. Also provided herein are compositions and methods for and the treatment of inflammatory disorders, particularly those that are $T_H$-GM-mediated.

BRIEF DESCRIPTION OF THE DRAWINGS

The foregoing will be apparent from the following more particular description of example embodiments of the invention.

In FIGS. 8A-8D, splenocytes were obtained from MOG$_{35-55}$/CFA-immunized Stat5$^{+/+}$ and Stat5$^{-/-}$ mice (n=3 per group) before disease onset and challenged with MOG$_{35-55}$ at various concentrations for 24 h. GM-CSF secretion was measured by ELISA (FIG. 8A). Golgiplug was added in the last 4 h of MOG$_{35-55}$ (20 µg/ml) challenge and the frequencies of IL-17$^+$ and GM-CSF$^+$ cells among CD4$^+$CD44$^{hi}$ T cells were measured (FIG. 8B). In FIGS. 8C and 8C, splenocytes were obtained from MOG$_{35-55}$/CFA-immunized Stat5$^{-/-}$, Stat3$^{-/-}$ or wild-type control mice and stimulated with PMA/Ionomycin in the presence of Golgiplug for 4 h. The frequencies of IL-17$^+$ and GM-CSF$^+$ cells among splenic CD4$^+$CD44$^{hi}$ T cells were measured by intracellular cytokine staining. *p<0.05, ***p<0.001.

In FIG. 9A, IL-17, IFN-γ and GM-CSF expression by CNS-infiltrating CD4$^+$ T cells of Stat5$^{+/+}$ and Stat5$^{-/-}$ mice was measured at peak of disease. The percentage of GM-CSF$^+$ cells among IL-17$^+$ or IFN-γ$^+$ cells was calculated (bottom right, FIG. 9A). IL-17, IFN-γ and GM-CSF expression by CNS-infiltrating CD4$^+$ T cells of Rag2$^{-/-}$ recipient mice at peak of disease in adoptive transfer EAE (FIG. 9B). Time-course analysis of cytokine mRNA expression in the CNS of naïve and MOG$_{35-55}$/CFA-immunized Stat5$^{+/+}$ and Stat5$^{-/-}$ mice (n=3 per group at each time point). The RT-PCR data were normalized to Rn18S, and expression in naïve mice was set to 1 (FIG. 9C). Data represent two independent experiments. *p<0.05.

FIGS. 10A-10C show STAT5-mediated GM-CSF induction is independent of IL-23 or IL-1β signaling. In FIG. 10A, purified CD4$^+$ T cells were cultured with TGF-β and IL-6 for 3 days, followed by starvation for 6 h. Then cells were treated with various cytokines for 30 min, and pSTAT3 and pSTAT5 was determined by immunoblotting. STAT3 and STAT5 were further detected after stripping. FIG. 10B shows the mRNA expression of IL-23R and IL-1R1 in splenic CD4$^+$ T cells of Stat5$^{+/+}$ and Stat5$^{-/-}$ EAE mice (n=3 per group). The RT-PCR data were normalized to β-Actin. In FIG. 10C, splenocytes were obtained from MOG$_{35-55}$/CFA-immunized WT mice before disease onset and challenged with MOG$_{35-55}$ (20 µg/ml) in the absence or presence of IL-2 for 48 h. The frequencies of GM-CSF$^+$ and IL-17$^+$ cells among CD4$^+$CD44$^{hi}$ T cells were measured by flow cytometry. *p<0.05.

FIGS. 12D and 12E illustrate the frequencies of GM-CSF+, IL-17+ and IFN-γ+ cells among CD4+ T cells in the CNS of EAE mice receiving different treatment. The mRNA expression of IFN-γ, IL-17 and GM-CSF in the CNS of EAE mice (FIG. 12F). *p<0.05

In FIG. 14B, sorted naïve CD4+ T cells were stimulated with anti-CD3 and anti-CD28 in the presence of neutralizing antibodies against IL-12 and IFN-γ without or with the addition of IL-6. The frequencies of GM-CSF+ and IL-17+ cells were measured by intracellular staining (FIG. 14B). In FIG. 14C, naïve CD4+ T cells from $Stat3^{+/+}$ and $Stat3^{-/-}$ mice were polarized under conditions as indicated for 72 h. The frequencies of GM-CSF+ and IL-17+ cells were analyzed. In FIG. 14D, naïve CD4+ T cells were activated with anti-CD3 and anti-CD28 in the presence of IL-2 or anti-IL-2. The frequencies of GM-CSF+, IL-17+ and IFN-γ+ cells were analyzed.

In FIGS. 15C and 15D, $Stat5^{+/+}$ and $Stat5^{-/-}$ naïve CD4+ T cells were activated with anti-CD3 and anti-CD28 in the presence IL-7 for 3 days. GM-CSF, IL-17 and IFN-γ expression was analyzed by intracellular cytokine staining (FIG. 15C). GM-CSF secretion was measured by ELISA (FIG. 15D). Immunoblotting of pSTAT5 and STAT5 in IL-7-stimulated CD4+ T cells isolated from $Stat5^{-/-}$ or control mice (FIG. 15E). The ChIP assay was performed with $Stat5^{+/+}$ and $Stat5^{-/-}$ CD4+ T cells using normal IgG or STAT5-specific antibody. The binding of antibodies to Csf2 promoter region was detected by RT-PCR (FIG. 15F).

FIGS. 17A-17C show flow cytometry of CD25 and CD127 on the surface of naïve CD4+ T cells or cells activated with anti-CD3 and anti-CD28 at various time points as indicated. Activation of STAT5 in naïve CD4+ T cells stimulated with IL-2 or IL-7 for 30 min (FIG. 17D). FIG. 17E shows the mRNA expression of GM-CSF in naïve CD4+ T cells stimulated with anti-CD3 and anti-CD28 in the presence of IL-2 or IL-7. The RT-PCR data were normalized to β-Actin, and expression in naïve T cells activated for 2 h without cytokine was set to 1.

As shown in FIGS. 18A and 18B, CD4+ T cells were activated with anti-CD3 and anti-CD28 for 3 days. After resting in fresh medium, cells were stimulated with IL-2 or IL-7 at various time points. The pTyr-STAT5 and β-Actin were detected by immunoblotting (FIG. 18A). GM-CSF mRNA expression was measured by RT-PCR (FIG. 18B). The RT-PCR data were normalized to β-Actin, and expression in cells without cytokine stimulation was set to 1. The ChIP assay shown in FIG. 18C was performed with normal IgG or STAT5-specific antibody. The binding of antibodies to Csf2 promoter region was detected by RT-PCR.

In FIGS. 20A and 20B, naïve CD4+ T cells were activated with anti-CD3 and anti-CD28 under $T_H1$-(IL-12+anti-IL-4), $T_H17$-(TGF-β+IL-6+anti-IFN-γ+anti-IL-4) and $T_H$-GM-(GM-CSF+ $T_H$, IL-7+anti-IFN-γ+anti-IL-4) polarizing conditions. GM-CSF and IL-3 expression was analyzed by intracellular staining (FIG. 20A). The mRNA expression of IL-3, EBI-3, PENK or RANKL cytokines was measured by RT-PCR (FIG. 20B). Frequency of IL-3+ cells differentiated without or with IL-7 (FIG. 20C). GM-CSF and IL-3 expression by WT or STAT5-deficient GM-CSF-producing TH cells (FIG. 20D).

FIGS. 22A-27E depict inhibition of STAT5 activation suppresses $T_H$-GM cell differentiation in vitro. CD4+ T cells were pre-incubated with STAT5 inhibitor (Calbiochem) (FIG. 22A) or JAK3 inhibitor (FIG. 22B) at indicated concentrations or vehicle (−) for 1 h before stimulation with IL-7 for 30 min. Activation (Tyr694 phosphorylation) of STAT5 was determined by immunoblotting. CD4+ T cells were pre-incubated with STAT5 inhibitor at indicated concentrations or vehicle (−) for 1 h before stimulation with IL-6 for 30 min. Activation (Tyr705 phosphorylation) of STAT3 was determined by immunoblotting (FIG. 22C). In FIG. 22D, CD4+ T cells were pre-incubated with STAT5 inhibitor at indicated concentrations or vehicle (−) for 1 h before stimulation with IFN-γ for 30 min. Activation (Tyr701 phosphorylation) of STAT1 was determined by immunoblotting. In FIG. 22E, naïve CD4+ T cells were isolated and activated under neutral condition or $T_H$-GM cell-favoring condition with the addition of different concentrations of STAT5 inhibitor for 3 days. GM-CSF and IFN-γ expression was analyzed by intracellular cytokine staining and flow cytometry.

(FIG. 23A) Clinical EAE scores of wild-type control mice (n=5) or administrated with STAT5 inhibitor (Calbiochem). Arrow indicates the treatment points. (FIG. 23B) Histology of spinal cords at day 18 of EAE mice receiving different treatments. (FIG. 23C) Intracellular staining and flow cytometry of CNS-infiltrating CD4$^+$ T cells at peak of disease. (FIG. 23D) Whole CNS was harvest for RNA extraction. GM-CSF mRNA expression was analyzed by RT-PCR. Data represent two independent experiments. *p<0.05.

In FIGS. 24B and 24C, peripheral blood mononuclear cells (PBMCs) were collected from healthy control (HC) and rheumatoid arthritis (RA) patients, and were stimulated for 4 h with PMA/Ionomycin in the presence of Golgiplug, followed by intracellular cytokine staining. Representative flow cytometry of GM-CSF, IFN-γ and IL-17 in CD4$^+$ T cells (FIG. 24B) and statistics of n>=9 per group (FIG. 24C) are shown. FIG. 24D shows the correlation between the frequency of GM-CSF$^+$ IFN-γ$^-$ $T_H$ cells and the level of plasma GM-CSF in peripheral blood of RA patients (n=18). Cytokine expression by CD4$^+$ T cells derived from synovial fluid of RA patients was analyzed by intracellular cytokine staining and flow cytometry (FIG. 24E). A representative image of three cases was shown. *p<0.05, p<0.01, *p<0.001; ns, not significant.

FIG. 25A shows knee joint swelling of wild-type mice over 7 days after intraarticular injection of 100 μg mBSA in AIA model, receiving treatment with control IgG, GM-CSF-specific and TNF-α-specific neutralizing antibodies separately or in combination (n=5 per group) at indicated times (arrows). FIG. 25B shows knee joint swelling of Stat5$^{+/+}$ and Stat5$^{-/-}$ mice (n=6 per group) over 7 days after arthritis induction. Data are representative of more than three independent experiments. Representative images of joint sections stained with H&E (FIG. 25C) or Safranin-O/Fast Green (FIG. 25D) at day 7 after arthritis induction as in FIG. 25C. Bars, 500 μm (FIG. 25C upper panels and FIG. 25D) or 100 μm (FIG. 25C lower panels). Arrow in upper panels (FIG. 25C) indicated bone destruction. In FIG. 25E, serum concentrations of GM-CSF, IFN-γ and TNF-α in Stat5$^{+/+}$ and Stat5-/- AIA mice were quantified by ELISA. Statistics of n>=8 per group were shown. *p<0.05, p<0.01, *p<0.001.

(FIG. 26A) Representative images of paw swelling of Stat5$^{+/+}$ and Stat5$^{-/-}$ mice at day 40 after collagen II/CFA immunization in CIA model. (FIG. 26B) Clinical score of Stat5$^{+/+}$ and Stat5$^{-/-}$ mice (n=5 per group) over 40 days after collagen II/CFA immunization. Data are representative of two independent experiments. (FIG. 26C) Representative images of paw sections stained with H&E at day 40. (FIG. 26D) Serum concentrations of TNF-α (n=8 per group) were quantified by ELISA. *p<0.05, p<0.01, *p<0.001.

FIGS. 27A-27E depicts STAT5-deficient CD4$^+$ T cells are defective in arthritogenic potential. (FIGS. 27A and 27B) Representative flow cytometry of CD4$^+$ T cells in spleens (FIG. 27A) and inguinal lymph nodes (FIG. 27B) of Stat5$^{+/+}$ and Stat5$^{-/-}$ mice at day 7 after AIA induction. (FIGS. 27C and 27D) Synovial tissues were harvested from Stat5$^{+/+}$ and Stat5$^{-/-}$ mice at day 7 after AIA induction, and dissociated into single cells. Cell numbers of CD45$^+$ leukocytes were calculated (FIG. 27C). The percentages of CD4$^+$ T cells among CD45$^+$ fraction were analyzed by flow cytometry, and cell numbers were calculated (FIG. 27D). (FIG. 27E) Histological analysis of joint sections from wild-type naïve mice at day 7 after being transferred with in vitro-expanded antigen-reactive CD4$^+$ T cells and followed with intraarticular injection of mBSA. Bars, 100 μm. Data represent two independent experiments. *p<0.05; ns, not significant.

(FIG. 28A) Splenic fractions of wild-type AIA mice (n=3) were stimulated under indicated conditions for 18 h. GM-CSF levels in supernatant were quantified by ELISA. (FIGS. 28B-28D) Intracellular staining and flow cytometry of GM-CSF, IL-17 and IFN-γ in splenic CD4$^+$CD44$^{hi}$ effector T cells (FIG. 28B) or in synovial infiltrating CD4$^+$ T cells (FIGS. 28C and 28D) after restimulation for 4 h with PMA/Ionomycin in the presence of Golgiplug. Representative images and statistics of n=5 (FIG. 28B, right panels) or n=3 (FIG. 28D, right panels) per group were shown. Data represent two independent experiments. (FIG. 28E) Protein expression of several proinflammatory cytokines in synovial tissues was measured by ELISA. (FIGS. 28F and 28G) Representative images of joint sections stained with H&E (FIG. 28F) or Safranin-O/Fast Green (FIG. 28G) at day 7 after intraarticular injection of mBSA alone to the right knee joints and mBSA supplemented with GM-CSF to the left knee joints. Bars, 500, 50 or 200 μm as indicated. Data represent two independent experiments.*p<0.05, p<0.01, p<0.05, p<0.01, ***p<0.001; ns, not significant. "Splenocytes" represent the left-most bars in each group, "splenocytes depleted of CD4+ T cells" represent the middle bars in each group, and "CD4+ T cells" represent the right-most bars in each group.

(FIG. 29A) Golgiplug was added in the last 4 h of culture, followed by intracellular staining and flow cytometry. Representative plots of GM-CSF, IL-17 and IFN-γ expression in CD4$^+$CD44$^{hi}$ effector T cells was shown, representing two independent experiments. (FIGS. 29B and 29C) Secreted cytokines in the supernatant (n=3 per group) were quantified by ELISA. Data represent two independent experiments. *p<0.05; ns, not significant.

(FIGS. 30A-30C) The mRNA (FIGS. 30A and 30 C) and protein (FIG. 30B) expression of several proinflammatory cytokines in synovial tissues of Stat5$^{+/+}$ and Stat5$^{-/-}$ mice (n>=3 per group) at day 5 or 7 after arthritis induction was measured by qPCR and ELISA. The qPCR data were normalized to Rn18S.

(FIG. 31A) The frequencies of CD11b$^+$ cells in spleens of Stat5$^{+/+}$ and Stat5$^{-/-}$ AIA mice were analyzed by flow cytometry. Statistics of n=3 per group (right panel) were shown. (FIG. 31B) Synovial tissues were harvested from Stat5$^{+/+}$ and Stat5$^{-/-}$ mice at day 7 after arthritis induction, and dissociated into single cell suspensions. The percentage of CD11b$^+$ myeloid cells among CD45$^+$ fraction was analyzed by flow cytometry. Statistics of n=5 per group were shown in right panel. (FIG. 31C) Representative flow cytometry of CD11b$^+$ and CD4$^+$ cells gated on synovial CD45$^+$ fraction over 7 days after arthritis induction. (FIG. 31D) Flow cytometric analysis of CD4$^+$, CD11b$^+$ and B220$^+$ cell infiltration in synovial tissues of Stat5$^{+/+}$ and Stat5$^{-/-}$ mice at day 7 after intraarticular injection of mBSA alone to the right knee joints and mBSA supplemented with GM-CSF to the left knee joints. Representative images were shown. All data shown are representative of two independent experiments. **p<0.01; ns, not significant.

(FIG. 32A) Flow cytometric analysis of Ly6C and Ly6G expression gated on synovial CD45$^+$CD11b$^+$ fraction over 7 days after arthritis induction. (FIG. 32B) Giemsa stain of sorted Ly6C$^{hi}$Ly6G$^-$ and Ly6C$^{lo}$Ly6G$^{hi}$ cells from synovial tissues of AIA mice. Scale bar, 100 μm (left) or 20 μm (right). (FIG. 32C) Flow cytometric analysis of Ly6C$^{hi}$Ly6G$^-$ and Ly6C$^{lo}$Ly6G$^{hi}$ populations in synovial tissues of Stat5$^{+/+}$ and Stat5$^{-/-}$ mice at day 7 after intraarticular injection of mBSA alone to the right knee joints and mBSA supplemented with GM-CSF to the left knee joints. (FIG. 32D) Knee joint swelling of wild-type mice treated with Ly6G-specific neutralizing antibody (1A8) or IgG control (n=5 per group) over 3 days after intraarticular injection of mBSA in AIA model. Arrows indicate time points of antibody administration. *p<0.05.

FIGS. 33A-33C depicts GM-CSF enhances neutrophil transmigration and delay apoptosis in vitro. (FIG. 33A) Percentages of migrated neutrophils with or without GM-CSF as chemoattractant in transmigration assay at 3 h post start. (FIG. 33B) Microscopic images of CFSE-labeled neutrophils in the bottom of the lower chamber in transmigration assay. (FIG. 33C) Sorted neutrophils were cultured in vitro with or without GM-CSF (20 ng/ml) for 24 h. Neutrophils undergoing apoptosis were examined by Annexin V and propidium iodide (PI) co-staining. A representative flow cytometry of three repeats was shown. *p<0.05.

(FIG. 34A) Flow cytometry plots depicting the fractionation into different populations based on differential expression of surface markers. (FIG. 34B) The mRNA expression of several proinflammatory cytokines in sorted CD45$^+$ TCRβ$^+$ (TCRβ$^+$ in short), CD45$^+$ TCRβ$^-$CD11c$^-$CD11b$^+$ (CD11b$^+$) and CD45$^+$ TCRβ$^-$CD11c$^+$ (CD11c$^+$) populations was measured by qPCR. The qPCR data were normalized to GAPDH. (FIG. 34C) The mRNA expression of IL-6, IL-1β and TNF-α in sorted Ly6C$^{hi}$Ly6G$^-$ and Ly6C$^{lo}$Ly6G$^{hi}$ populations (gated on CD11b$^+$ cells). The qPCR data were normalized to GAPDH. (FIGS. 34D and 34E) The mRNA expression of IL-6 and IL-1β by BMDMs (FIG. 34D) and BMDCs (FIG. 34E) upon stimulation with 20 ng/ml GM-CSF for 1 h. The qPCR data were normalized to GAPDH. (FIGS. 34F and 34G) BMDMs (FIG. 34F) and BMDCs (FIG. 34G) were stimulated with GM-CSF at indicated concentrations (n=3 per group) for 18 h. The secretion of IL-6 in the culture supernatant was quantified by ELISA. (FIG. 34H) BMDMs were primed with LPS (100 μg/ml) in the presence of GM-CSF at indicated concentrations (n=3 per group) for 6 h, followed by stimulation with ATP (5 mM) for 30 min. The secretion of IL-1β in the culture supernatant was quantified by ELISA. (FIG. 34I) Cells were cultured in DMEM medium supplemented with 10% FBS for over 20 days with more than 5 passages to obtain synovial fibroblasts. Synovial fibroblasts were stimulated with GM-CSF (20 ng/ml) for 1 h and harvested for RNA extraction. The mRNA expression of IL-1β was measured by qPCR. The qPCR data were normalized to GAPDH. All data shown represent two independent experiments. *p<0.05, **p<0.01.

DETAILED DESCRIPTION OF THE INVENTION

Figures 1A, 1B, 1C, 1D:
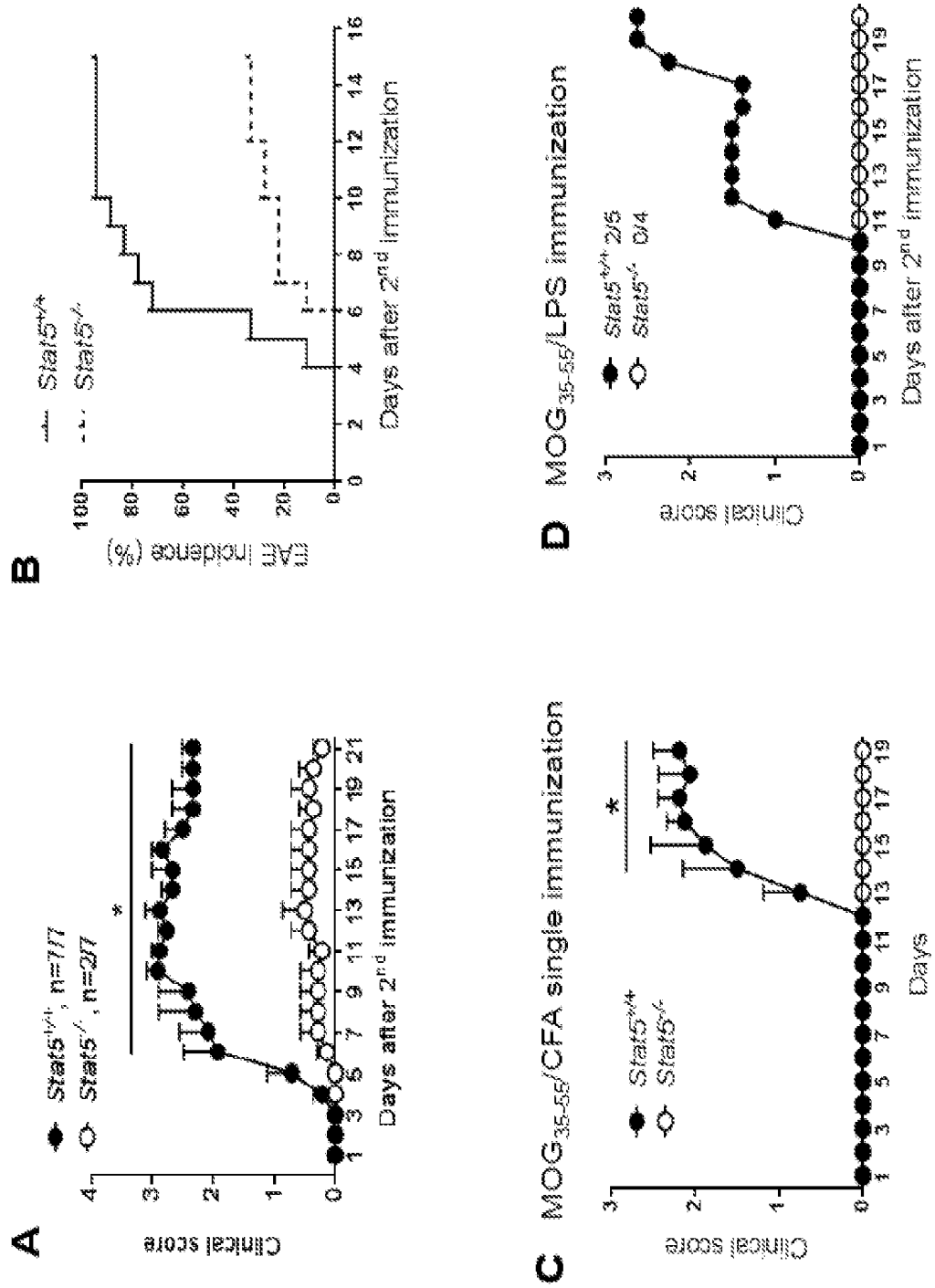
FIGS. 1A-1D depict Stat5-conditional mutant mice are resistant to EAE. Clinical EAE scores (FIG. 1A) and incidence (FIG. 1B) of Stat5$^{+/+}$ and Stat5$^{-/-}$ mice immunized twice with MOG$_{35-55}$/CFA. Data are representative of three independent experiments (FIG. 1A) or pooled from three experiments (FIG. 1B, n=18 per group). Clinical scores of EAE mice immunized once with MOG$_{35-55}$/CFA (FIG. 1C, n=5 per group) or immunized twice with MOG$_{35-55}$/LPS (FIG. 1D). Data are representative of two independent experiments.

A description of example embodiments of the invention follows.

The present disclosure relates, in part, to the identification of a granulocyte macrophage colony stimulating factor (GM-CSF)-secreting T helper cell, termed "$T_H$-GM". As detailed herein, IL-7/STAT5 signaling programs the differentiation of precursor CD4+ cells to $T_H$-GM, a process which is further modulated by IL-2 and IL-23 signaling. $T_H$-GM cells are characterized by, e.g., GM-CSF and IL-3 production. $T_H$-GM cells are distinct from the known helper T cells $T_H$1 and $T_H$17, with respect to, e.g., differentiation conditions, transcriptional regulation and effector cytokine expression. For example, IL-12/IFN-γ and TGF-β/IL-6, which mediate (e.g., promote the development of) $T_H$1 and $T_H$17, respectively, potently suppress the development of $T_H$-GM from naïve CD4$^+$ precursor cells, establishing that $T_H$-GM cells develop via a lineage distinct from $T_H$1 and $T_H$17. Thus, the present disclosure provides a distinct network of factors, unique from factors known to mediate $T_H$1 or $T_H$17, that mediate $T_H$-GM function (e.g., its differentiation and pathogenicity).

As shown herein, $T_H$-GM cells preferentially induce EAE as compared with $T_H$1 and $T_H$17 cells, indicating that $T_H$-GM cells represent the primary effectors in the pathogenesis of autoimmune neuroinflammation in humans. Moreover, blockade of IL-7 signaling and/or inhibition of STAT5 function (e.g., abrogation of expression or inhibition of STAT5 activity) attenuates autoimmune neuroinflammation associated with diminished GM-CSF production by $T_H$-GM cells. Further, blockade of $T_H$-GM cell-secreted GM-CSF ameliorates experimental arthritis in a TNF-α-independent manner, indicating an approach for the treatment of, e.g., rheumatoid arthritis patients who are unresponsive to TNF-α antagonistic drugs. Thus, the present disclosure enables one to distinguish between an inflammatory disorder (e.g., RA) that is mediated by the $T_H$-GM pathway (e.g., a disorder that results from $T_H$-GM pathogenicity through the action of, e.g., GM-CSF and/or IL-3, or any factor associated with the $T_H$-GM pathway), or an inflammatory disorder that is mediated by, e.g., TNF-α, IL-6, and/or IL-1β pathways (i.e., non-$T_H$-GM-mediated pathway). For example, a patient who has, e.g., RA may be afflicted with a type of RA that is primarily $T_H$-GM-mediated, or primarily non-$T_H$-GM-mediated (e.g., TNF-α-mediated or IL-6 mediated). The present disclosure enables the classification between $T_H$-GM-mediated and non-$T_H$-GM-mediated inflammation, allowing for a more precise diagnosis, prognosis, and treatment in an individual who is afflicted with an inflammatory disorder such as RA or MS.

As demonstrated herein, the present disclosure identifies a helper T cell subset (T-$_H$-GM), provides the molecular basis for the commitment and development of this subset from naïve precursor cells in vitro and in vivo, and demonstrates $T_H$-GM cells as the primary pathogenic cells in autoimmune diseases and inflammatory disorders, for example, MS and RA. Thus, provided herein are compositions and methods for diagnosing inflammatory conditions primarily mediated by $T_H$-GM cells, thereby enabling the identification of, e.g., RA patients who are non-responsive to TNF-α therapy (e.g., TNF-α inhibitor based therapy), as well as compositions and methods for modulating $T_H$-GM function to treat autoimmune and inflammatory disorders. The methods of modulating $T_H$-GM function include, e.g., administering agents to modulate the function (e.g., signaling, expression or activity) of the network of factors (e.g., IL-2/IL-7/STAT5/GM-CSF/IL-3) that mediate $T_H$-GM function in an effective amount to modulate the function (e.g., development and pathogenicity) of $T_H$-GM cells. In particular, the disclosure provides methods and composition for differentiating and diagnosing an inflammatory disorder, e.g., multiple sclerosis (MS), rheumatoid arthritis (RA) as primarily mediated by either $T_H$-GM cells (i.e., $T_H$-GM pathway mediated) or by non-$T_H$-GM mechanism (e.g., TNF-α, IL-6, and/or IL-1β pathways), or both. Also provided herein are compositions and methods for and the treatment of inflammatory disorders, particularly those that are $T_H$-GM-mediated.

Accordingly, in one aspect, the present disclosure provides a method of diagnosing a $T_H$-GM-mediated inflammatory disorder in a patient suffering from an inflammatory disorder. In some embodiments, the method comprises contacting a sample collected from a patient suffering from an inflammatory disorder with a detecting agent that detects a polypeptide or nucleic acid level of a $T_H$-GM-mediating factor, such as, e.g., STAT5, IL-7, GM-CSF or IL-3, or a combination thereof; and quantifying the polypeptide or nucleic acid level of the $T_H$-GM-mediating factor (e.g., STAT5, IL-7, GM-CSF or IL-3, or a combination thereof), wherein an increased level of a $T_H$-GM-mediating factor (e.g., STAT5, IL-7, GM-CSF or IL-3, or a combination thereof) relative to a reference level indicates that the patient suffers from a $T_H$-GM-mediated inflammatory disorder, thereby diagnosing a $T_H$-GM-mediated inflammatory disorder in a patient suffering from an inflammatory disorder.

As used herein, a "$T_H$-GM-mediated" inflammatory disorder refers to a subtype of an inflammatory disorder (e.g., a subtype of RA or MS) that results from the physiological action of any one or more of the network of factors in the pathway that modulate $T_H$-GM function (a "$T_H$-GM-mediating factor"), as described herein. Such factors include, e.g., GM-CSF, activated STAT5, IL-7, IL-2, and IL-3. In a particular embodiment, STAT5 is activated STAT5, wherein tyrosine at position 694 is phosphorylated.

In some embodiments, the level of a $T_H$-GM-mediating factor (e.g., STAT5, IL-7, GM-CSF or IL-3, or a combination thereof) that is not increased relative to a reference level indicates that the patient suffers from a non-$T_H$-GM-mediated inflammatory disorder.

In certain embodiments, the method further comprises administering to the patient a TNF-α therapy, as described herein, if the level of a $T_H$-GM-mediating factor (e.g., STAT5, IL-7, GM-CSF or IL-3, or a combination thereof) is not increased relative to a reference level.

As used herein, a "non-$T_H$-GM-mediated" inflammatory disorder refers to an inflammatory disorder (e.g., RA or MS) that is primarily caused by, e.g., TNF-α, IL-6, or IL-1β (and/or factors in the TNF-α, IL-6, or IL-1β pathway). As such, a "$T_H$-GM-mediated" inflammatory disorder results primarily (or exclusively) from a pathway that is distinct from one or more of the pathways that leads to a "non-$T_H$-GM-mediated" inflammatory disorder (e.g., the pathways associated with TNF-α, IL-6, or IL-1β).

However, as those of skill in the art would appreciate, a $T_H$-GM-mediated inflammatory disorder does not necessarily exclude the possibility that the inflammatory disorder could also be partially non-$T_H$-GM-mediated (e.g., mediated by TNF-α, IL-6, or IL-1β, and/or factors in the TNF-α, IL-6, or IL-1β pathway). Thus, a classification or diagnosis as "$T_H$-GM-mediated" is synonymous with "primarily/predominantly $T_H$-GM-mediated", and a classification as "non-$T_H$-GM-mediated" is synonymous with "primarily/predominantly non-$T_H$-GM-mediated." For example, without wishing to be bound by any particular theory, an inflammatory disorder in its early stage may be $T_H$-GM-mediated. As the inflammatory condition advances to a late stage characterized by, e.g., tissue damage, the inflammatory disorder becomes progressively non-$T_H$-GM-mediated. In some embodiments, a $T_H$-GM-mediated inflammatory disorder is a condition that is responsive to modulation of $T_H$-GM function, as determined by clinical standards; a non-$T_H$-GM-mediated inflammatory disorder is a condition that is responsive to, e.g., TNF-α, IL-6, or IL-1β therapy, as determined by clinical standards. In certain embodiments, an inflammatory disorder can be responsive to modulation of $T_H$-GM function as well as TNF-α, IL-6, and/or IL-1β therapy.

In some embodiments, the sample can be e.g., peripheral blood, cerebrospinal fluid, synovial fluid, or synovial membrane, or a combination thereof.

In some embodiments, the inflammatory disorder is an autoimmune disorder. In certain embodiments, the inflammatory disorder can be any inflammatory disorder mediated by $T_H$-GM cells, and includes, but is not limited to rheumatoid arthritis, multiple sclerosis, ankylosing spondylitis, Crohn's disease, diabetes, Hashimoto's thyroiditis, hyperthyroidism, hypothyroidism, Irritable Bowel Syndrome (IBS), lupus erythematosus, polymyalgia rheumatic, psoriasis, psoriatic arthritis, Raynaud's syndrome/phenomenon, reactive arthritis (Reiter syndrome), sarcoidosis, scleroderma, Sjögren's syndrome, ulcerative colitis, uveitis, or vasculitis.

As used herein, a "detecting agent" refers to, e.g., an antibody, a peptide, a small molecule, or a nucleic acid that binds to a polypeptide or nucleic acid to be detected (e.g., STAT5 (e.g., phospho-STAT5 (Tyr694)), IL-7, GM-CSF or IL-3), and enables the quantification of the polypeptide or nucleic acid to be detected. The detecting agent can be detectably labeled, or quantifiable by other means known in the art.

In some embodiments, the detecting agent is an antibody that binds to the polypeptide of STAT5, IL-7, GM-CSF or IL-3. In one embodiment, the antibody is one that binds to an activated STAT5 (e.g., phosphorylated STAT5), as described herein. Antibodies to STAT5 (e.g., phospho-STAT5 (Tyr694)), IL-7, GM-CSF or IL-3 suitable for use in the present method are known and commercially available in the art (e.g., STAT5 Ab: C-17 from Santa Cruz Biotech; Phospho-STAT5 (Tyr694) Ab: #9351 or #9359 from Cell Signaling; IL-7 Ab: clone BVD10-40F6 from BD Pharmingen; IL-7R Ab: clone SB/14 from BD Pharmingen; GM-CSF Ab: clone MP1-22E9 from BD Pharmingen; IL-3 Ab: clone MP2-8F8 from BD Pharmingen.

In other embodiments, the detecting agent is a nucleic acid that binds to the nucleic acid of STAT5, IL-7, GM-CSF and/or IL-3. Nucleic acid molecules encoding a, e.g., STAT5, IL-7, GM-CSF and/or IL-3 sequence, or fragments or oligonucleotides thereof, that hybridize to a nucleic acid molecule encoding a e.g., STAT5, IL-7, GM-CSF and/or IL-3 polypeptide sequence at high stringency may be used as a probe to monitor expression of nucleic acid levels of STAT5, IL-7, GM-CSF and/or IL-3 in a sample for use in the diagnostic methods of the disclosure. Methods of quantifying nucleic acid levels are routine and available in the art.

In some embodiments, the method further comprises contacting the sample with a detecting agent that detects a polypeptide or nucleic acid level of one or more genes (as well as the gene product) listed in Table 1. As described herein, Table 1 lists genes that are differentially expressed in T$_H$-GM cells as well as genes that are differentially expressed on the surface of T$_H$-GM cells, as compared to T$_H$1 or T$_H$17 cells.

In a particular embodiment, the method further comprises contacting the sample with a detecting agent that detects the polypeptide or nucleic acid level of basic helix-loop-helix family member e40 (BHLHe40), chemokine (C-C Motif) Receptor 4 (CCR4), and/or CCR6.

Standard methods may be used to quantify polypeptide levels in any sample. Such methods include, e.g., ELISA, Western blotting, immunohistochemistry, fluorescence activated cells sorting (FACS) using antibodies directed to a polypeptide, and quantitative enzyme immunoassay techniques known in the art. Such methods are routine and available in the art. Similarly, methods for quantifying nucleic acid levels (e.g., mRNA) are known in the art.

In the diagnostic method of the present disclosure, an increased level of STAT5 (e.g., activated phospho-STAT5 (Tyr694)), IL-7, GM-CSF and/or IL-3 relative to a reference level indicates that the patient suffers from a T$_H$-GM-mediated inflammatory disorder.

In some embodiments, a STAT5 (e.g., activated phospho-STAT5 (Tyr694)), IL-7, GM-CSF and/or IL-3 level that is increased by at least 10%, at least 20%, at least 30%, at least 40%, at least 50%, at least 60%, at least 70%, at least 80%, at least 90%, at least 100%, at least 110%, at least 120%, at least 130%, at least 140%, at least 150%, at least 160%, at least 170%, at least 180%, at least 190%, at least 200%, at least 220%, at least 240%, at least 260%, at least 280%, at least 300%, at least 350%, at least 400%, at least 450%, at least 500%, at least 550%, or at least 600% relative to a reference level indicates that the patient suffers from a T$_H$-GM-mediated inflammatory disorder. In a particular embodiment, an increase of at least 40%, at least 50%, at least 60%, at least 70%, at least 80%, at least 90%, at least 100%, or at least 150% relative to a reference level indicates that the patient suffers from a T$_H$-GM-mediated inflammatory disorder.

In some embodiments, a STAT5 (e.g., activated phospho-STAT5 (Tyr694)), IL-7, GM-CSF and/or IL-3 level that is not increased by at least 40%, at least 50%, at least 60%, at least 70%, at least 80%, at least 90%, at least 100%, or at least 150% relative to a reference level indicates that the patient suffers from a non-T$_H$-GM-mediated inflammatory disorder.

In certain embodiments, a STAT5 (e.g., activated phospho-STAT5 (Tyr694)), IL-7, GM-CSF and/or IL-3 level that is comparable (or unchanged) relative to a reference level indicates that the patient suffers from a non-T$_H$-GM-mediated disorder. As used herein, a level that is "comparable" to that of a reference level refers to a level that is unchanged, or a change relative to the reference level that is statistically insignificant according to clinical standards. In certain embodiments, a comparable level (or unchanged level) can include a level that is not increased by at least 40%, at least 50%, at least 60%, or at least 70% relative to a reference level as, for example, it may not indicate a clinically significant change. In some embodiments, a level of a T$_H$-GM-mediating factor (e.g., STAT5 (e.g., activated phospho-STAT5 (Tyr694)), IL-7, GM-CSF, and/or IL-3) that is decreased relative to a reference level can also indicate that the patient suffers from a non-T$_H$-GM-mediated disorder.

In some embodiments, the reference level is a level that is used for comparison purposes, and may be obtained from, for example, a prior sample taken from the same patient; a normal healthy subject; a sample from a subject not having an autoimmune disease or an inflammatory disorder; a subject that is diagnosed with a propensity to develop an autoimmune disease but does not yet show symptoms of the disease; a patient that has been treated for an autoimmune disease; or a sample of a purified reference polypeptide or nucleic acid molecule of the disclosure (e.g., STAT5) at a known normal concentration. By "reference standard or level" is meant a value or number derived from a reference sample, or a value or range accepted in the art as indicative of being healthy (e.g., an individual that does not have an inflammatory disorder). A normal reference standard or level can also be a value or number derived from a normal subject who does not have an autoimmune disease. In one embodiment, the reference sample, standard, or level is matched to the sample subject by at least one of the following criteria: age, weight, body mass index (BMI), disease stage, and overall health. A standard curve of levels of purified DNA, RNA or mRNA within the normal reference range can also be used as a reference. A standard curve of levels of purified protein within the normal reference range can also be used as a reference.

In some embodiments, the patient afflicted with an inflammatory disorder who has been diagnosed or classified as having a T$_H$-GM-mediated inflammatory disorder does not have a non-T$_H$-GM-mediated inflammatory disorder (i.e., does not have a TNF-α, IL-6, or IL-1β-mediated inflammatory disorder). That is, the patient diagnosed as suffering from a T$_H$-GM-mediated inflammatory disorder responds to modulation of T$_H$-GM function (e.g., inhibition of STAT5, IL-7, GM-CSF and/or IL-3), but does not respond (or exhibits a limited response) to TNF-α therapy, as determined by clinical standards. However, as described herein, a T$_H$-GM-mediated inflammatory disorder does not exclude the possibility that the inflammatory disorder is also partially (though not primarily) contributed by a non-T$_H$-GM-mediated pathway (e.g., TNF-α, IL-6, IL-1β).

In some embodiments, the methods of the present disclosure further comprise administering an effective amount of a modulating agent that modulates T$_H$-GM cell function to the patient diagnosed or classified as having a T$_H$-GM-mediated inflammatory disorder. As described herein, in some embodiments, the modulating agent inhibits T$_H$-GM function.

In some embodiments, the methods of the present disclosure further comprise administering an effective amount of, e.g., a TNF-α therapy, an IL-6 therapy, or an IL-1β therapy to a patient diagnosed or classified as having a non-T$_H$-GM-mediated inflammatory disorder, as described herein.

In some aspects, the present disclosure also provides a method of classifying a patient suffering from an inflammatory disorder as having a T$_H$-GM-mediated inflammatory disorder or a non-T$_H$-GM-mediated inflammatory disorder. In some embodiments, the method comprises contacting a sample collected from a patient suffering from an inflammatory disorder with a detecting agent that detects a polypeptide or nucleic acid level of a T$_H$-GM-mediating factor, such as, e.g., STAT5 (e.g., phosphorylated STAT5, Tyr694), IL-7, GM-CSF or IL-3, or a combination thereof. In certain aspects, the method further comprises quantifying the polypeptide or nucleic acid level of the T$_H$-GM-mediating factor, such as, e.g., STAT5, IL-7, GM-CSF or IL-3, or a combination thereof, wherein an increased level of the T$_H$-GM-mediating factor, such as, e.g., STAT5, IL-7, GM-CSF or IL-3, or a combination thereof relative to a reference level indicates that the patient suffers from a T$_H$-GM-mediated inflammatory disorder; or a comparable level of the T$_H$-GM-mediating factor, such as, e.g., STAT5, IL-7, GM-CSF or IL-3, or a combination thereof relative to a reference level indicates that the patient suffers from a non-$T_H$-GM-mediated inflammatory disorder, thereby classifying the patient suffering from an inflammatory disorder as a $T_H$-GM-mediated inflammatory disorder or a non-$T_H$-GM-mediated inflammatory disorder.

In other aspects of the present disclosure, the methods disclosed herein can further comprise measuring the polypeptide or nucleic acid level of a factor that mediates a non-$T_H$-GM-mediated inflammatory disorder. Such factors include, e.g., TNF-α, IL-6, and IL-1β.

For example, in some aspects, the present disclosure provides a method of determining a treatment regimen in a patient suffering from an inflammatory disorder. To illustrate, the method comprises quantifying a polypeptide or nucleic acid level of, e.g., activated STAT5 or GM-CSF in a sample collected from a patient suffering from an inflammatory disorder, and quantifying the polypeptide or nucleic acid level of, e.g., TNF-α in a sample collected from the patient. At least four scenarios can be considered.

In the first scenario, if the activated STAT5 or GM-CSF level is increased (e.g., by at least 40%, at least 50%, at least 60%, at least 70%, at least 80%, at least 90%, at least 100%, or at least 150%) relative to a first reference level and the TNF-α level is comparable to a second reference level, then the patient is classified as having a $T_H$-GM-mediated inflammatory disorder and the patient can be treated with an agent that modulates $T_H$-GM function, as described herein.

In a second scenario, if the activated STAT5 or GM-CSF level is comparable to the first reference level and the TNF-α level is increased (e.g., by at least 40%, at least 50%, at least 60%, at least 70%, at least 80%, at least 90%, at least 100%, or at least 150%) relative to the second reference level, then the patient is classified as having a non-$T_H$-GM-mediated inflammatory disorder and the patient can be treated with, e.g., a TNF-α therapy.

In a third scenario, if the activated STAT5 or GM-CSF level is increased relative to the first reference level and the TNF-α level is also increased relative to the second reference level, and the increase is equivalent within clinical and/or statistical standards (e.g. both GM-CSF and TNF-α are at least 50% increased relative to the respective reference levels), then the patient is classified as having an inflammatory disorder that is equally $T_H$-GM-mediated and non-$T_H$-GM mediated (e.g., TNF-α-mediated). In such a case, the patient can be treated with an effective amount of an agent that modulates $T_H$-GM function and an effective amount of, e.g., a TNF-α therapy. As demonstrated herein, the combination of both agents can have a synergistic effect.

In a fourth scenario, if the activated STAT5 or GM-CSF level is increased relative to the first reference level and the TNF-α level is also increased relative to the second reference level, but one is increased more than the other, then the inflammatory disorder is primarily mediated by the pathway that shows a greater increase. For example, if GM-CSF is increased by 40% relative to a reference level, and TNF-α is increased by 90% relative to a reference level, then the inflammatory disorder is primarily non-$T_H$-GM-mediated. However, in this scenario, the patient may receive a combined treatment with an agent that modulates $T_H$-GM function as well a TNF-α therapy (e.g., anti-TNF-α therapy), since GM-CSF is increased by, e.g., at least 40% relative to a reference level.

In some embodiments, the first and second reference levels are obtained from the same reference sample.

In a related aspect, the disclosure also provides a method of tailoring the treatment of a patient suffering from an inflammatory disorder according to the progression of a patient's inflammatory disorder. In the above illustrative example, the first scenario (increased $T_H$-GM-mediating factor, e.g. STAT5 or GM-CSF but TNF-α level is comparable to a reference level) may indicate that the patient is in an early stage of an inflammatory disorder. Without wishing to be bound by any particular theory, during, for example, the early stages of an inflammatory disorder, naïve T cells are stimulated by antigen and programmed by IL-7/STAT5 to differentiate into GM-CSF/IL-3 producing $T_H$-GM cells. During, for example, the late stages of an inflammatory disorder, $T_H$-GM cytokines (e, g, IL-3 and GM-CSF) progressively stimulate more inflammatory cells such as macrophages and neutrophils resulting in the production of, e.g., TNF-α, IL-6, IL-1β, resulting in full-scale inflammation. Thus, in the above illustrative example, the second scenario (activated STAT5 or GM-CSF level is comparable to the first reference level and the TNF-α level is increased) may indicate that the patient is in a late stage of an inflammatory disorder characterized by, e.g., tissue damage. Accordingly, the present disclosure enables the prognosis of a patient depending on the quantifiable level of one or more $T_H$-GM-mediating factor (e.g., STAT5 (e.g., activated phospho-STAT5 (Tyr694)), IL-7, GM-CSF, and/or IL-3) and one or more non-$T_H$-GM-mediating factor (e.g., TNF-α, IL-6, IL-1β), thereby tailoring the treatment according to the progression of the disease. Accordingly, as would be appreciated by those of skill in the art, a patient suffering from an inflammatory disorder can be monitored for disease progression to ensure effective and tailored treatment according to the level of one or more $T_H$-GM-mediating factor, as described herein, and one or more non-$T_H$-GM-mediating factor (e.g., TNF-α, IL-6, IL-1β).

In related aspects, the present disclosure also provides a method of prognosing progression of an inflammatory disorder in a patient in need thereof. In some embodiments, the method comprises a) quantifying a polypeptide or nucleic acid level of a $T_H$-GM-mediating factor, such as, e.g., STAT5, IL-7, GM-CSF or IL-3, or a combination thereof, in a first sample collected from a patient suffering from an inflammatory disorder, and b) quantifying a polypeptide or nucleic acid level of, e.g., TNF-α, IL-6, or IL-1β, or a combination thereof, in a second sample collected from the patient, wherein i) an increased level of the $T_H$-GM-mediating factor, such as, e.g., STAT5, IL-7, GM-CSF or IL-3, or a combination thereof relative to a first reference level and an unchanged level of TNF-α, IL-6, or IL-1β, or a combination thereof relative to a second reference level indicates that the patient is in an early stage of the inflammatory disorder, as described herein; or ii) an unchanged level of the $T_H$-GM-mediating factor, such as, e.g., STAT5, IL-7, GM-CSF or IL-3, or a combination thereof relative to the first reference level and an increased level of TNF-α, IL-6, or IL-1β, or a combination thereof relative to the second reference level indicates that the patient is in a late stage of the inflammatory disorder, as described herein. In some embodiments, the method further comprises administering an effective amount of an agent that modulates $T_H$-GM function and/or, e.g., a TNF-α therapy, as described herein.

In some embodiments, the first sample and the second sample are the same.

In various aspects, the present disclosure also provides an isolated population of GM-CSF-secreting T-helper cells ($T_H$-GM). In one embodiment, the $T_H$-GM cells are differentiated from a precursor cell (e.g., CD4+ cells) in the presence of signal transducer and activator of transcription 5 (STAT5) and/or IL-7, and wherein the $T_H$-GM cells express GM-CSF and IL-3.

In some embodiments, the $T_H$-GM cells are differentiated from a precursor cell (e.g., CD4+ cells) in the presence of an agent that inhibits IL-12, IFN-γ, TGF-β, and/or IL-6. Similarly, the differentiation of a precursor cell (e.g., CD4+ precursor cell) into a $T_H$-GM cell is inhibited by IL-12, IFN-γ, TFG-β, and/or IL-6.

In some embodiments, the $T_H$-GM cells are differentiated from a precursor cell in vitro, under artificial conditions, but wherein the $T_H$-GM cells retain physiological properties as described herein.

In some embodiments, the $T_H$-GM cells are further characterized by an overexpression of one or more genes listed in Table 1. For example, the $T_H$-GM cells are further characterized by an overexpression of, for example, basic helix-loop-helix family, member e40 (BHLHe40), preproenkephalin (PENK), IL-2, serine (or cysteine) peptidase inhibitor, clade B member 6b (Serpinb6b), neuritin 1 (Nrn1), stearoyl-Coenzyme A desaturase 1 (Scd1), or phosphotriesterase related C1q-like 3 (Pter), or a combination thereof.

In some embodiments, the $T_H$-GM cells are further characterized by an underexpression of one or more genes listed in Table 1. For example, the $T_H$-GM cells are further characterized an underexpression of lymphocyte antigen 6 complex, locus A (Ly6a); CD27; or selectin, lymphocyte (Sell).

As described herein, the identification of a distinct network of factors (unique from factors known to mediate $T_H1$ or $T_H17$) that mediate $T_H$-GM function (e.g., its differentiation and pathogenicity) enables targeted modulation of $T_H$-GM function to treat $T_H$-GM-mediated disorders, e.g., disorders that result from aberrant $T_H$-GM function. Thus, in some aspects, the present disclosure provides a method of modulating $T_H$-GM function, comprising contacting the $T_H$-GM, or cluster of differentiation 4 (CD4+) precursor cells, or both, with a modulating agent that modulates $T_H$-GM function. In one embodiment, the modulating agent is contacted with the $T_H$-GM cells or CD4+ precursor cells in vitro or in vivo.

As used herein, "$T_H$-GM function" refers to the commitment, development, maintenance, survival, proliferation, or activity, or a combination thereof, of $T_H$-GM cells. Thus, an agent that modulates (e.g., enhances or inhibits) $T_H$-GM function is one that modulates $T_H$-GM commitment, development, survival, proliferation, or activity, or combination thereof, of $T_H$-GM cells. For example, $T_H$-GM function can be modulated by modulating its: commitment from a CD4+ precursor T cell; development of a CD4+ precursor cell that has been committed to the $T_H$-GM developmental pathway; maintenance of a $T_H$-GM phenotype; survival or proliferation under development or effector $T_H$-GM cells; and/or activity of effector $T_H$-GM cells (e.g., modulating function of a secreted factor such as GM-CSF or IL-3). For example, a modulation in $T_H$-GM function includes, but is not limited to, a modulation in: the number of $T_H$-GM cells; the survival of $T_H$-GM cells; the proliferation of $T_H$-GM cells; and/or the activity of $T_H$-GM cells. The activity of $T_H$-GM cells herein includes the activity induced by the cytokines, chemokines, growth factors, enzymes and other factors secreted by $T_H$-GM cells, as described herein, and the activity induced by direct contact with $T_H$-GM cells.

As used herein, a T helper subset cell "$T_H$-GM" refers to a cell that, similar to $T_H1$ and $T_H17$ cells, differentiates from precursor CD4+ precursor cells, but which commits and develops through a pathway that is mediated by a subset of factors (the $T_H$-GM-mediating factors) that is distinct and unique from the known subset of factors that commit and develop $T_H1$ or $T_H17$ cell subtypes, as described herein. In some embodiments, a $T_H$-GM cell produces a distinct and unique set of genes (see, e.g., Table 1) and effects pathogenicity through a different mechanism and pathway than the known factors that mediate pathogenicity of $T_H1$ or $T_H17$ cell subtypes. For example, a $T_H$-GM cell commits and develops by IL-7/STAT5 function (its regulators), and effects pathogenicity by GM-CSF/IL-3 (its effectors).

In some aspects, the present disclosure provides a method of treating a $T_H$-GM-mediated inflammatory disorder in a patient in need thereof, comprising administering to said patient an effective amount of a modulating agent that modulates $T_H$-GM cell function. In certain embodiments, the patient is previously diagnosed as having a $T_H$-GM-mediated inflammatory disorder, as described herein.

In some aspects, the present disclosure also provides a method of treating rheumatoid arthritis in a patient who exhibits limited response to TNF-α therapy, comprising administering to said patient an effective amount of a modulating agent that modulates $T_H$-GM function.

As used herein, "limited response" refers to no response or insignificant response such that a patient is not treated by the therapy, as determined by clinical standards.

"Treatment" or "treating" refers to therapy, prevention and prophylaxis and particularly refers to the administration of medicine or the performance of medical procedures with respect to a patient, for either prophylaxis (prevention) or to reduce the extent of or likelihood of occurrence of the condition or event in the instance where the patient is afflicted. It also refers to reduction in the severity of one or more symptoms associated with the disease or condition. In the present application, it may refer to amelioration of one or more of the following: pain, swelling, redness or inflammation associated with an inflammatory condition or an autoimmune disease. As used herein, and as well-understood in the art, "treatment" is an approach for obtaining beneficial or desired results, including clinical results. For purposes of this disclosure, beneficial or desired clinical results include, but are not limited to, alleviation or amelioration of one or more symptoms, diminishment of extent of disease, stabilized (e.g., not worsening) state of disease, delay or slowing of disease progression, and/or amelioration or palliation of the disease state. "Treatment" can also mean prolonging survival as compared to expected survival if not receiving treatment.

An "effective amount" of an agent is that amount sufficient to effect beneficial or desired results, including clinical results. An "effective amount" depends upon the context in which it is being applied. In the context of administering a composition that modulates an autoimmune response, an effective amount of an agent which is a modulator of $T_H$-GM function is an amount sufficient to achieve such a modulation as compared to the response obtained when there is no agent administered. An effective amount can confer immediate, short term or long term benefits of disease modification, such as suppression and/or inhibition of $T_H$-GM function, as defined herein. An effective amount can be administered in one or more administrations. An "effective amount" as used herein, is intended to mean an amount sufficient to reduce by at least 10%, at least 25%, at least 50%, at least 75%, or an amount that is sufficient to cause an improvement in one or more clinically significant symptoms in the patient.

In some embodiments, the modulating agent inhibits $T_H$-GM function to, e.g., reduce inflammation. The inhibition conferred by the modulating agent (the inhibitor) does not imply a specific mechanism of biological action. Indeed, the term "antagonist" or "inhibitor" as used herein includes all possible pharmacological, physiological, and biochemical interactions with factors that mediate $T_H$-GM function (e.g., IL-7, IL-7 receptor, STAT5, GM-CSF, IL-3, IL-2, IL-2 receptor, PENK, RANKL, JAK1/3, or any of the genes that are differentially expressed in $T_H$-GM cells, e.g., genes in Tables 1 and 2), whether direct or indirect, and includes interaction with a factor (or its active fragment) that mediates $T_H$-GM function at the protein and/or nucleic acid level, or through another mechanism.

In certain embodiments, a modulating agent that inhibits $T_H$-GM function includes an antibody, a polypeptide (e.g., a soluble receptor that binds and inhibits, for example, IL-7), a small molecule, a nucleic acid (e.g., antisense, small interfering RNA molecule, short hairpin RNA, microRNA), or a protein (e.g., cytokine), or a combination thereof that prevents the function (e.g., expression and/or activity) of a factor that mediates $T_H$-GM function. Methods of designing, producing, and using such inhibitors are known and available in the art.

As used herein, "binds" is used interchangeably with "specifically binds," which means a polypeptide (e.g., a soluble receptor) or antibody which recognizes and binds a polypeptide of the present disclosure, but that does not substantially recognize and bind other molecules in a sample, for example, a biological sample, which naturally includes a polypeptide of the present disclosure. In one example, an antibody specifically binds an activated STAT5 polypeptide does not bind a non-STAT5 polypeptide.

As used herein, "antibody" refers to an intact antibody or antigen-binding fragment of an antibody, including an intact antibody or antigen-binding fragment that has been modified or engineered, or that is a human antibody.

In a particular embodiment, the antibody binds to and inhibits the function of any one or more of the factors that mediate $T_H$-GM function. For example, the antibody binds to and inhibits the function of IL-7, IL-7 receptor (IL-7R), IL-2, IL-2 receptor (IL-2R), STAT5 or janus kinase 1/3 (JAK1/3), or a combination thereof. In other examples, the antibody binds to and inhibits the function of GM-CSF (or its receptor), IL-3, PENK, or RANKL, or a combination thereof. In some embodiments, the antibody binds to and inhibits the function of a gene listed in Table 1. In some embodiments, the antibody binds to and inhibits the protein or any functional fragment thereof. Methods of designing, producing and using suitable antibodies are known and available to those of skill in the art. Examples of antibodies suitable for use in the present disclosure include, e.g., daclizumab, basiliximab, mavrilimumab, MOR103, KB003, namilumab, and MOR Ab-022.

The terms "protein" and "polypeptide" are used interchangeably, and can include full-length polypeptide or functional fragments thereof (e.g., degradation products, alternatively spliced isoforms of the polypeptide, enzymatic cleavage products of the polypeptide), the polypeptide bound to a substrate or ligand, or free (unbound) forms of the polypeptide. The term "functional fragment", refers to a portion of a full-length protein that retains some or all of the activity (e.g., biological activity, such as the ability to bind a cognate ligand or receptor) of the full-length polypeptide.

In some embodiments, the modulating agent that inhibits $T_H$-GM function can be a particular biological protein (e.g., cytokines) that inhibits, directly or indirectly, one or more of the factors that mediate $T_H$-GM function. Such cytokines include, e.g., IL-12, IFN-γ, TGF-β, and IL-6.

In some embodiments, the modulating agent that inhibits $T_H$-GM function can be a small molecule that inhibits, directly or indirectly, one or more of the factors that mediate $T_H$-GM function. As used herein a "small molecule" is an organic compound or such a compound complexed with an inorganic compound (e.g., metal) that has biological activity and is not a polymer. A small molecule generally has a molecular weight of less than about 3 kilodaltons. Examples of known small molecules include CAS 285986-31-4 (Calbiochem), pimozide, and tofacitinib.

In other embodiments, the modulating agent enhances $T_H$-GM function in disorders such as, e.g., viral, fungal and bacterial infections, cancers and/or conditions associated with therewith. In one embodiment, modulating agents that enhance $T_H$-GM function include, e.g., CD28 activator; IL-7 and/or IL-2 on naïve (precursor) $CD4^+$ T cells; activator of STAT5; or effectors of $T_H$-GM cells (e.g., GM-CSF, IL-3).

In another aspect, the present disclosure provides a method of treating a STAT5-mediated inflammatory disorder in a patient in need thereof, comprising administering to the patient an effective amount of an agent that modulates STAT5 function.

As used herein, "STAT5-mediated" inflammatory disorder refers to an inflammatory disorder that is caused by aberrant STAT5 function (aberrantly enhanced or inhibited), and which is responsive to modulation of STAT5 function, as determined by clinical standards. In some embodiments, the STAT5 is activated STAT5 (e.g., phospho-STAT5, Tyr694).

In some embodiments, the inflammatory disorder is an autoimmune disorder. In certain embodiments, the inflammatory disorder can be any inflammatory disorder mediated by STAT5 (e.g., activated STAT5), and includes, but is not limited to rheumatoid arthritis, multiple sclerosis, ankylosing spondylitis, Crohn's disease, diabetes, Hashimoto's thyroiditis, hyperthyroidism, hypothyroidism, Irritable Bowel Syndrome (IBS), lupus erythematosus, polymyalgia rheumatic, psoriasis, psoriatic arthritis, Raynaud's syndrome/phenomenon, reactive arthritis (Reiter syndrome), sarcoidosis, scleroderma, Sjögren's syndrome, ulcerative colitis, uveitis, or vasculitis.

In some embodiments, the term "patient" refers to a mammal, preferably human, but can also include an animal in need of veterinary treatment, e.g., companion animals (e.g., dogs, cats, and the like), farm animals (e.g., cows, sheep, pigs, horses, and the like), and laboratory animals (e.g., rats, mice, guinea pigs, and the like).

In some embodiments, the agent inhibits STAT5 function (e.g., expression and/or activity). Examples of agents that inhibit STAT5 (e.g., activated STAT5, Tyr694) are described herein.

In certain embodiments, the methods of the present disclosure further comprise administering to the patient a TNF-α therapy. In certain embodiments, TNF-α therapy is administered in a patient determined to have an inflammatory condition that is non-$T_H$-GM-mediated. As described herein, in certain embodiments, a TNF-α therapy is administered if a quantified TNF-α level is increased by, e.g., at least 40% relative to a reference level.

Examples of TNF-α therapy include those that are TNF-α-inhibitor based, and those that are non-TNF-α-inhibitor based. In particular, TNF-α-inhibitor based therapy includes etanercept, adalimumab, infliximab, golimumab, and certolizumab pegol. Examples of non-TNF-α-inhibitor based therapy includes corticosteroid medications (e.g., prednisone), nonsteroidal anti-inflammatory drugs (e.g., methotrexate), and JAK inhibitors (e.g., tofacitinib). Other examples of non-TNF-α-inhibitor based therapy include anakinra, abatacept, rituximab and tocilizumab.

The TNF-α therapy can be administered before, simultaneously with, or after the administration of an effective amount of an agent that modulates $T_H$-GM function. Accordingly, an agent that modulates $T_H$-GM function and the TNF-α therapy can be administered together in a single dose, or can be administered in separate doses, e.g., either simultaneously or sequentially, or both. The duration of time between the administration of an agent that modulates $T_H$-GM function and a TNF-α therapy will depend on the nature of the therapeutic agent(s). In addition, an agent that modulates $T_H$-GM function and a TNF-α therapy may or may not be administered on similar dosing schedules. For example, the agent that modulates $T_H$-GM function and the TNF-α therapy may have different half-lives and/or act on different time-scales such that the agent that modulates $T_H$-GM function is administered with greater frequency than the TNF-α therapy, or vice-versa. The number of days in between administration of therapeutic agents can be appropriately determined by persons of ordinary skill in the art according to the safety and pharmacodynamics of each drug.

The identification of the $T_H$-GM cells as well as the identification of genes differentially produced by $T_H$-GM cells relative to $T_H1$ or $T_H17$ enables the use of $T_H$-GM cells to identify novel therapeutics for modulating $T_H$-GM function, thereby enabling new therapeutics for treating $T_H$-GM-mediated disorders (e.g., inflammatory disorders). Thus, in further aspects, the present disclosure provides a method of screening to identify a modulator of $T_H$-GM cell function, comprising contacting an isolated population of $T_H$-GM cells, or an isolated population of CD4+ precursor cells, with a candidate agent, and measuring a readout of $T_H$-GM function in the presence or absence of the candidate agent, wherein a change in the readout of $T_H$-GM function indicates that the candidate agent is a modulator of $T_H$-GM function.

As used herein, a candidate agent refers to an agent that may modulate $T_H$-GM function by modulating the function (e.g., expression and/or activity) of a factor that mediates $T_H$-GM function. Such candidate agents include, e.g., an antibody, a peptide, a small molecule, a nucleic acid (e.g., antisense, small interfering RNA molecule), or a protein (e.g., cytokine), or a combination thereof. A candidate agent can be designed to target any of the factors (at the protein and/or nucleic acid level) that mediate $T_H$-GM function, as described herein, including the genes listed in Table 1 (e.g., genes preferentially upregulated in $T_H$-GM cells, genes preferentially overexpressed/underexpressed on the surface of $T_H$-GM cells).

As used herein, "readout" refers to any change (or lack of change) in $T_H$-GM function that can be measured or quantified. For example, a candidate agent can be assessed for its effect on, e.g., GM-CSF secretion by $T_H$-GM cells, or its effect on the abundance of $T_H$-GM cells (through an effect on the commitment/development/proliferation of $T_H$-GM cells), as described herein. Assays for determining such readouts are known and available in the art, and are exemplified herein.

In some embodiments, the change in the presence of the candidate agent is a reduction in the measurement of the readout, indicating an inhibition of $T_H$-GM function (e.g., decrease in GM-CSF or IL-3 production, or decrease in the abundance of $T_H$-GM cells), thereby identifying the candidate agent as an inhibitor of $T_H$-GM function.

In certain embodiments, the change in the presence of the candidate agent is an increase in the measurement of the readout, indicating an enhancement of $T_H$-GM function (e.g., increase in GM-CSF or IL-3 production, or increase in the abundance of $T_H$-GM cells), thereby identifying the candidate agent as an enhancer of $T_H$-GM function.

In some embodiments, the readout can be any one or more of the genes listed in Tables 1 and 2 which are preferentially upregulated or downregulated in $T_H$-GM cells. Thus, a candidate agent that downregulates a gene that is preferentially upregulated in a $T_H$-GM cell is a inhibitor of $T_H$-GM function. Similarly, a candidate agent that upregulates a gene that is preferentially downregulated in a $T_H$-GM cell is an enhancer of $T_H$-GM function.

In certain aspects, the method of screening, if performed with precursor CD4+ cells, is performed under $T_H$-GM polarizing conditions, as described herein. For example, the method can be performed in the presence of IL-7/STAT5, TCR activation, CD28 co-stimulation, in combination with the blockade of IFN-gamma and IL-4.

Unless indicated otherwise, the definitions of terms described herein apply to all aspects and embodiments of the present disclosure The practice of the present disclosure includes use of conventional techniques of molecular biology such as recombinant DNA, microbiology, cell biology, biochemistry, nucleic acid chemistry, and immunology as described for example in: Molecular Cloning: A Laboratory Manual, second edition (Sambrook et al., 1989) and Molecular Cloning: A Laboratory Manual, third edition (Sambrook and Russel, 2001), jointly and individually referred to herein as "Sambrook"); Oligonucleotide Synthesis (M. J. Gait, ed., 1984); Animal Cell Culture (R. I. Freshney, ed., 1987); Handbook of Experimental Immunology (D. M. Weir & C. C. Blackwell, eds.); Gene Transfer Vectors for Mammalian Cells (J. M. Miller & M. P. Calos, eds., 1987); Current Protocols in Molecular Biology (F. M. Ausubel et al., eds., 1987, including supplements through 2001); PCR: The Polymerase Chain Reaction, (Mullis et al., eds., 1994); Current Protocols in Immunology (J. E. Coligan et al., eds., 1991); The Immunoassay Handbook (D. Wild, ed., Stockton Press NY, 1994); Bioconjugate Techniques (Greg T. Hermanson, ed., Academic Press, 1996); Methods of Immunological Analysis (R. Masseyeff, W. H. Albert, and N. A. Staines, eds., Weinheim: VCH Verlags gesellschaft mbH, 1993), Harlow and Lane (1988) Antibodies, A Laboratory Manual, Cold Spring Harbor Publications, New York, and Harlow and Lane (1999) Using Antibodies: A Laboratory Manual Cold Spring Harbor Laboratory Press, Cold Spring Harbor, N.Y. jointly and individually referred to herein as "Harlow and Lane"), Beaucage et al. eds., Current Protocols in Nucleic Acid Chemistry (John Wiley & Sons, Inc., New York, 2000); and Agrawal, ed., Protocols for Oligonucleotides and Analogs, Synthesis and Properties (Humana Press Inc., New Jersey, 1993).

Exemplification

Methods

Mice

Stat5$^{f/f}$ mice were provided by L. Hennighausen (National Institute of Diabetes and Digestive and Kidney Diseases). Stat3$^{f/f}$ mice were generated as described[2]. Cd4-Cre transgenic mice were purchased from Taconic Farms. Rag2$^{-/-}$ mice were obtained from Jean-Pierre Abastado (Singapore Immunology Network). All mice are on a C57BL/6 genetic background and housed under specific-pathogen-free conditions at National University of Singapore. All experiments were performed with mice 6~8 weeks old and approved by the Institutional Animal Care and Use Committee of NUS.

Patients and Controls

Blood samples (n=47) and synovial fluid samples (n=3) were collected from RA patients admitted to the Department of Rheumatology and Immunology, the Affiliated Drum Tower Hospital of Nanjing University Medical School. All patients fulfilled the American College of Rheumatology criteria for the classification of RA. Age and gender matched healthy controls (n=32) were obtained from Medical Examination Center of the Affiliated Drum Tower Hospital. The study protocol was approved by the Ethics Committee of the Affiliate Drum Tower Hospital of Nanjing University Medical School.

In Vitro T Cell Differentiation $CD4^+$ T cells were obtained from spleens and lymph nodes by positive selection and magnetic separation (Miltenyi Biotech), followed by purification of naïve $CD4^+$ T cell population ($CD4^+CD25^-CD62L^{hi}CD44^{lo}$) sorted with FACS Aria. Naïve $CD4^+$ T cells were stimulated with plate-bound anti-CD3 (3 µg/ml; BD Pharmingen) and anti-CD28 (1 µg/ml; BD Pharmingen) in presence of different combinations of neutralizing antibodies and cytokines for 3~4 days: for neutral conditions, no addition of any cytokine or neutralizing antibody; for $T_H1$ conditions, IL-12 (10 ng/ml), and anti-IL-4 (10 µg/ml, BD Pharmingen); for $T_H17$ conditions, hTGF-β (3 ng/ml), IL-6 (20 ng/ml), anti-IFN-γ (10 µg/ml, eBioscience), and anti-IL-4 (10 µg/ml); for an alternative $T_H17$ conditions, IL-6 (20 ng/ml), IL-23 (10 ng/ml), IL-1β (10 ng/ml), anti-IFN-γ (10 µg/ml), and anti-IL-4 (10 µg/ml). For GM-CSF-expressing cell differentiation, naïve $CD4^+$ T cells were stimulated with plate-bound anti-CD3 (2 µg/ml) and soluble anti-D28 (1 µg/ml) with the addition of IL-7 and/or anti-IFN-γ (10 µg/ml) as indicated. All cytokines were obtained from R&D Systems. All cells were cultured in RPMI 1640 supplemented with 10% FBS, 100 units/ml penicillin, 0.1 mg/ml streptomycin, 1 mM sodium pyruvate, 0.1 mM nonessential amino acid and 5 µM beta-mercaptoethanol. After 3~4 days polarization, cells were washed and restimulated with phorbol 12-myristate 13-acetate (PMA) and ionomycin in presence of Golgiplug for 4-5 h, followed by fixation and intracellular staining with a Cytofix/Cytoperm kit from BD Pharmingen. Foxp3 staining was done with a kit from eBioscience. Cells were acquired on the LSR II (BD Biosciences) and analyzed with FlowJo software (Tree Star).

EAE Induction

EAE induction procedures were modified from previous report[3]. For active EAE induction, mice were immunized in two sites on the hind flanks with 300 µg $MOG_{35-55}$ in 100 µl CFA containing 5 mg/ml heat-killed *M. tuberculosis* strain H37Ra (Difco) at day 0 and day 7. Pertussis toxin (List Bio Lab) was administrated intraperitoneally at the dosage of 500 ng per mouse at day 1 and day 8. For single $MOG_{35-55}$/CFA immunization, the similar procedure was performed at day 0 and day 1 only. In an alternative active EAE induction, LPS (600 µg/ml in IFA, O111:B4 from Sigma) was used as adjuvant. For active EAE induction in $Rag2^{-/-}$ mice, $CD4^+$ T cells derived from $Stat5^{f/f}$ or Cd4-Cre; $Stat5^{f/f}$ mice were transferred, followed by $MOG_{35-55}$/CFA immunization as described above. Clinical symptoms were scored as follows: 0, no clinical sign; 1, loss of tail tone; 2, wobbly gait; 3, hind limb paralysis; 4, hind and fore limb paralysis; 5, death. IL-7Rα neutralizing antibody (SB/14, BD Pharmingen) and isotype control was administrated intraperitoneally at 200 µg per mouse every other day. For analysis of CNS-infiltrating cells, both spinal cord and brain were collected and minced from perfused mice, and mononuclear cells were isolated by gradient centrifuge with Percoll (GE Healthcare).

For passive EAE induction with $Stat5^{+/+}$ or $Stat5^{-/-}$ $CD4^+$ T cells, splenocytes and LNs were harvested 10-14 days post-immunization and passed through a 70 µm cell strainer (BD Falcon). Cells were cultured in vitro for 3 days with $MOG_{35-55}$ (20 µg/ml) in the presence of IL-23 (5 ng/ml) and IL-1β (2 ng/ml). After harvesting, $CD4^+$ T cells were purified by positive selection to a purity >90%. $CD4^+$ T cells (2 million in sterile PBS) were injected intraperitoneally into $Rag2^{-/-}$ mice, followed by Pertussis toxin administration on the following day. Mice were observed daily for the signs of EAE as described above. For EAE induction by transferring various $T_H$ subsets, similar procedures was performed as described above. Different subsets skewing conditions were as follows: Non-skewed, $MOG_{35-55}$ only; $T_H1$: $MOG_{35-55}$ plus IL-12 (10 ng/ml) and anti-IL-4 (5 µg/ml); $T_H17$: $MOG_{35-55}$ plus TGF-β (3 ng/ml), IL-6 (10 ng/ml), anti-IFN-γ (5 µg/ml) and anti-IL-4 (5 µg/ml); GM-CSF-expressing $T_H$: $MOG_{35-55}$ plus IL-7 (2 ng/ml) and anti-IFN-γ (5 µg/ml). $6 \times 10^5$ $CD4^+$ T cells were transferred per recipient mouse.

Antigen-Induced Arthritis (AIA)

Briefly, mice were immunized subcutaneously in two sites on the hind flanks with 100 µg methylated bovine serum albumin (mBSA, Sigma) in 100 µl complete Freund's adjuvant (CFA) containing 5 mg/ml heat-killed *M. tuberculosis* strain H37Ra (Difco) at day 0. Pertussis toxin (List Bio Lab) was administrated intraperitoneally at the dosage of 250 ng per mouse at day 1. Arthritis was induced by intraarticular injection of 100 µg mBSA (in 10 µl saline) into the hind right knee joint at day 7 after immunization. The hind left knee joint was injected with same volume of saline as control. Joint swelling was recorded by measuring the difference between right and left knee joint diameters with a caliper over 7 days after arthritis induction. To assess the effect of GM-CSF administration, AIA was induced by intraarticular injection of mBSA alone to the right knee joint or mBSA supplemented with 100 ng GM-CSF (ImmunoTools) to the left knee joint. To assess the effect of GM-CSF and/or TNF-α blockade, mice were administrated intraperitoneally with neutralizing antibodies (100 µg for each antibody per mouse) specific for GM-CSF (MP1-22E9, BD Pharmingen) and/or TNF-α (MP6-XT3, BD Pharmingen) at indicated times.

For AIA induction by adoptive transfer, splenocytes and inguinal LN cells were isolated from mBSA/CFA-immunized mice at day 7, and cultured in vitro with mBSA (10 µg/ml) in the presence of IL-7 (2 ng/ml) for 3 days. After harvesting, $CD4^+$ T cells were purified by positive selection (Miltenyi Biotec) to a purity >90%. Then $CD4^+$ T cells (1 million in sterile PBS) were transferred into WT naïve mice, followed by intraarticular injection of mBSA on the next day.

Collagen-Induced Arthritis (CIA)

CIA was induced in a similar procedure as AIA as described above, by immunizing mice with chicken collagen II/CFA emulsion (purchased from Chondrex, Inc), followed with pertussis toxin injection. Mice were monitored and scored for arthritis: 0, normal; 1, mild swelling of ankle or wrist, or apparent swelling limited to individual digits; 2, moderate swelling of entire paw; 3, severe swelling of entire paw with ankylosis. Scores for four limbs were summed for each mouse.

Histological Analysis

For paraffin-embedded tissues, spinal cords were fixed in 4% PFA. Knee joints or paws were removed, fixed in 10% formalin and decalcified in 5% formic acid before dehydration and embedding. Sections (5 µm) were stained with hematoxylin and eosin (H&E) to assess immune cell infiltration and inflammation, or with Safranin-O/Fast Green to assess cartilage depletion. For frozen tissues, spinal cords were embedded in OCT (Tissue-Tek) and snap frozen on dry ice. Sections (10 µm) were fixed in ice-cold acetone and stained with primary anti-CD4 (Biolegend) and anti-CD11b (eBioscience), followed by incubation with fluorescence-conjugated secondary antibodies (Invitrogen). For AIA experiments, knee joint were fixed in 10% formalin for 5 days, followed by decalcification in 5% formic acid for 5 days. Sections (10 µm) were stained with hematoxylin and eosin (H&E) to assess immune cell infiltration and inflammation, or stained with Safranin-O/fast green to access cartilage destruction.

Cell Sorting and May Grünwald-Giemsa Staining

Monocytes/macrophages (Ly6C$^{hi}$Ly6G$^-$) and neutrophils (Ly6C$^{lo}$Ly6G$^{hi}$) gated on CD45$^+$CD11b$^+$ were sorted with FACS Aria from spleens or synovial single cell suspensions. Sorted cells were cytospun onto glass slides and subsequently stained with May Grünwald and Giemsa dye following a standard procedure.

Real-Time PCR

Total RNA was extracted from cells with RNeasy kit (Qiagen) according to the manufacturer's instruction. Complementary DNA (cDNA) was synthesized with Superscript reverse transcriptase (Invitrogen). Gene expressions were measured by 7500 real-time PCR system (Applied Biosystems) with SYBR qPCR kit (KAPA). Actinb, Gapdh or Rn18S was used as internal control. The primer sequences are available upon request.

ELISA

TNF-α, IL-6, IL-1β, IFN-γ, GM-CSF and IL-2 levels were assayed by Ready-SET-Go ELISA kit (eBioscience), and IL-17 level was measured by DuoSet ELISA kit (R&D Systems) according to the manufactures' instructions.

Chromatin Immunoprecipitation Assays

CD4$^+$ T cells isolated from Stat5$^{f/f}$ or Cd4-Cre; Stat5$^{f/f}$ mice were activated with plate-bound anti-CD3 and anti-CD28 for 3 days. Cells were stimulated with IL-7 (20 ng/ml) or IL-2 (25 ng/ml) for 45 min. Crosslink was performed by addition of formaldehyde at final concentration of 1% for 10 min followed by quenching with Glycine. Cell lysates were fragmented by sonication and precleared with protein G Dynabeads, and subsequently precipitated with anti-STAT5 antibody (Santa Cruz) or normal rabbit IgG (Santa Cruz) overnight at 4° C. After washing and elution, crosslink reversal was done by incubating at 65° C. for 8 hr. The eluted DNA was purified and analyzed by RT-PCR with primers specific to Csf2 promoter as described previously[5].

Statistics

Statistical significance was determined by Student's t test using GraphPad Prism 6.01. The p value<0.05 was considered significant. The p values of clinical scores were determined by two-way multiple-range analysis of variance (ANOVA) for multiple comparisons. Unless otherwise specified, data were presented as mean and the standard error of the mean (mean±SEM).

Example 1. Stat5 Conditional Knockout Mice are Resistant to EAE

Figures 2A, 2B, 2C, 2D:
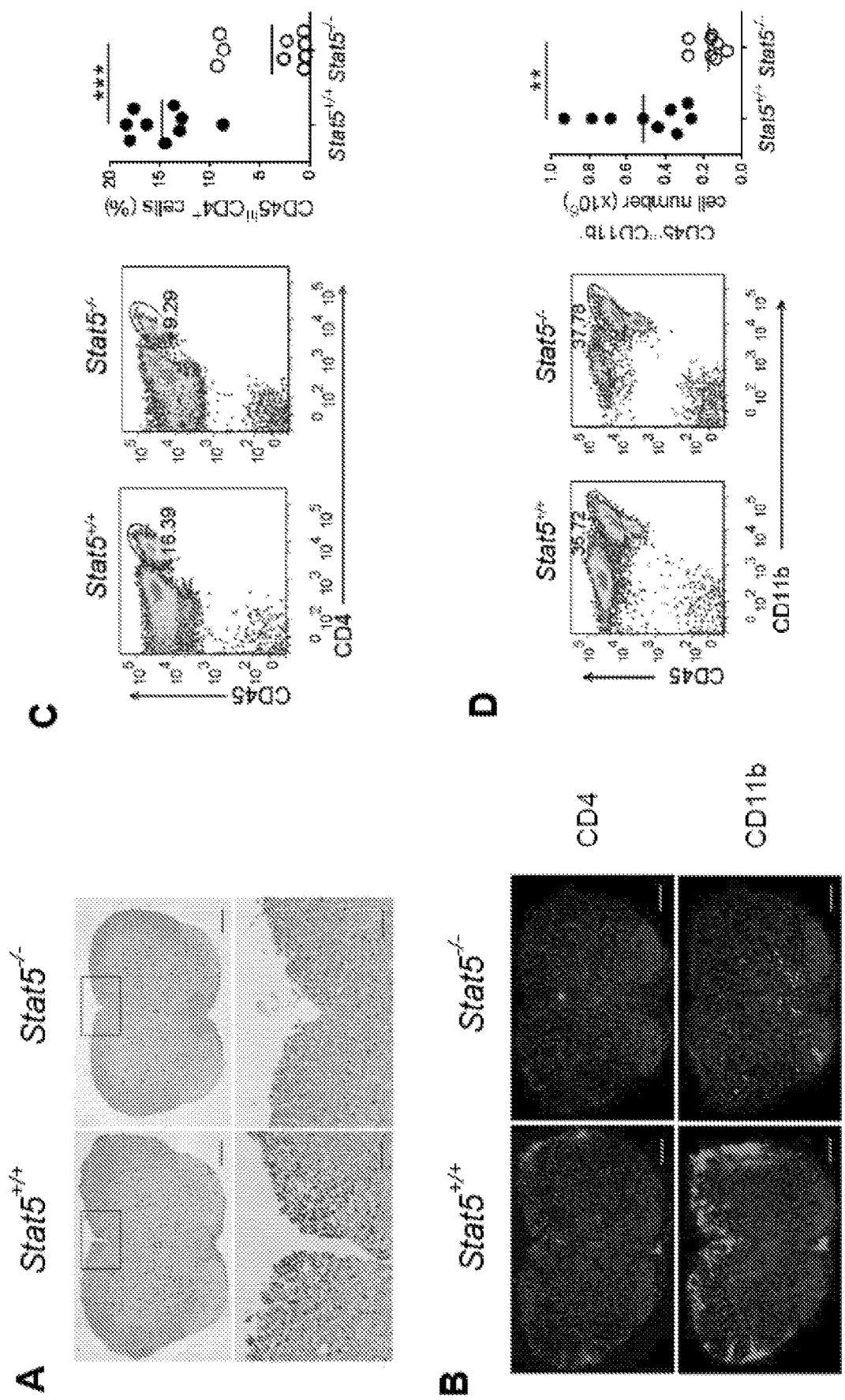
FIGS. 2A-2D depict reduced neuroinflammation in Stat5 conditional mutant mice. Histology of spinal cord sections obtained from EAE mice at day 9 after $2^{nd}$ immunization (FIG. 1A). Images shown are representative of two independent experiments with three mice per group. Scale bars, 200 µm (top), 50 µm (bottom). CD4$^+$ and CD11b$^+$ cells in spinal cord sections were stained by immunofluorescence (FIG. 1B). Images shown are representative of two independent experiments with three mice per group. Scale bars, 200 µm. CNS mononuclear cells were analyzed by flow cytometry at peak of disease (FIGS. 2C and 2D). Right panels are cell proportions (FIG. 2C, right) or cell numbers (FIG. 2D, right) pooled from two experiments (n=9).
Figures 3A, 3B:
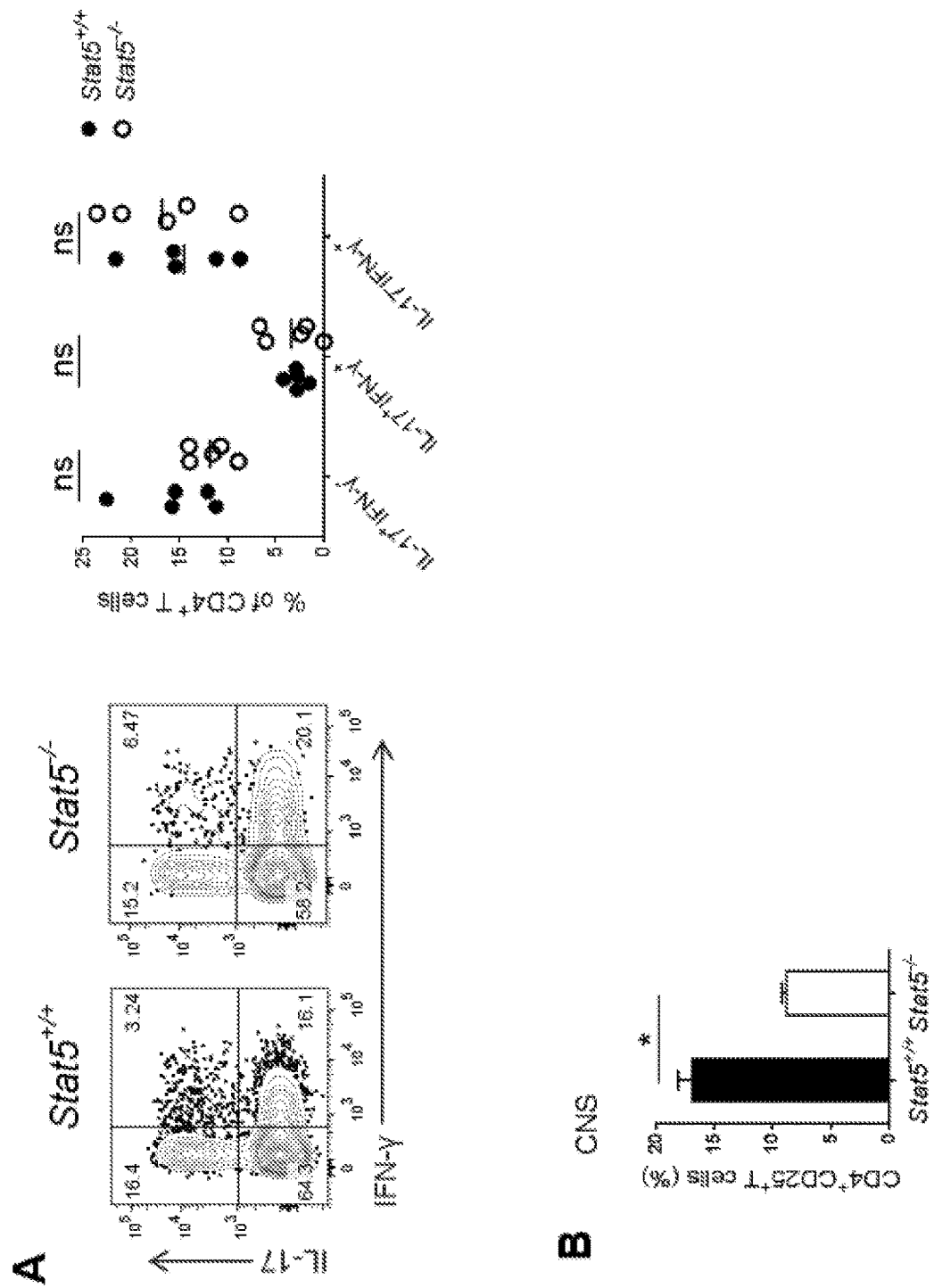
FIGS. 3A and 3B depict the resistance to EAE in Stat5-deficient mice is independent of $T_H1$, $T_H17$ or $T_{reg}$ cells. Flow cytometric analysis of IL-17 and IFN-γ expression by CNS-infiltrating CD4$^+$ T cells at peak of disease (FIG. 3A). Data are representative of three independent experiments. Percentage of CD25$^+$ among CD4$^+$ T cells in the CNS of Stat5$^{+/+}$ and Stat5$^{-/-}$ EAE mice at peak of disease were analyzed by flow cytometry (FIG. 3B).

STAT5 negatively regulates $T_H17$ differentiation by restraining IL-17 production (Laurence et al., 2007; Yang et al., 2011). However, the function of STAT5 in $T_H17$-mediated pathogenesis is not well understood. To explore this question, EAE was induced in Cd4-Cre; Stat5$^{f/f}$ (Stat5$^{-/-}$) mice, where Stat5 was specifically deleted in T cell compartment, and in littermate controls by immunizing the mice with MOG$_{35-55}$/CFA at day 0 and day 7. Development of paralysis was assessed by daily assignment of clinical scores. Surprisingly, diminished occurrence and severity of clinical disease in Stat5$^{-/-}$ mice was observed (FIGS. 1A and 1B), a result that was opposite to expectations based on an antagonistic role for STAT5 in $T_H17$ generation. Similar results were observed when a single MOG$_{35-55}$/CFA immunization was performed or replaced CFA with LPS as the adjuvant to induce EAE (FIGS. 1C and 1D). Consistent with reduced EAE disease in Stat5$^{-/-}$ mice, a remarkable reduction of immune cell infiltration in the spinal cord of Stat5$^{-/-}$ mice was observed (FIG. 2A). Furthermore, the infiltration of various immune cell populations, including CD4$^+$, CD8$^+$, B220$^+$ and CD11b$^+$ cells was reduced in Stat5$^{-/-}$ mice (FIGS. 2B-D and data not shown). However, the frequencies of IL-17$^+$ and IFN-γ$^+$ cells among CD4$^+$ T cells in the CNS were comparable between Stat5$^{+/+}$ and Stat5$^{-/-}$ mice (FIG. 3A), suggesting the resistance to EAE in Stat5$^{-/-}$ mice is independent of $T_H1$ and $T_H17$ cell development. Nevertheless, decreased CD4$^+$CD25$^+$ $T_{reg}$ population in the CNS of Stat5$^{-/-}$ mice was detected (FIG. 3B), indicating the resistance to EAE in Stat5$^{-/-}$ mice was unlikely due to altered $T_{reg}$ cells.

Figures 4A, 4B, 4C:
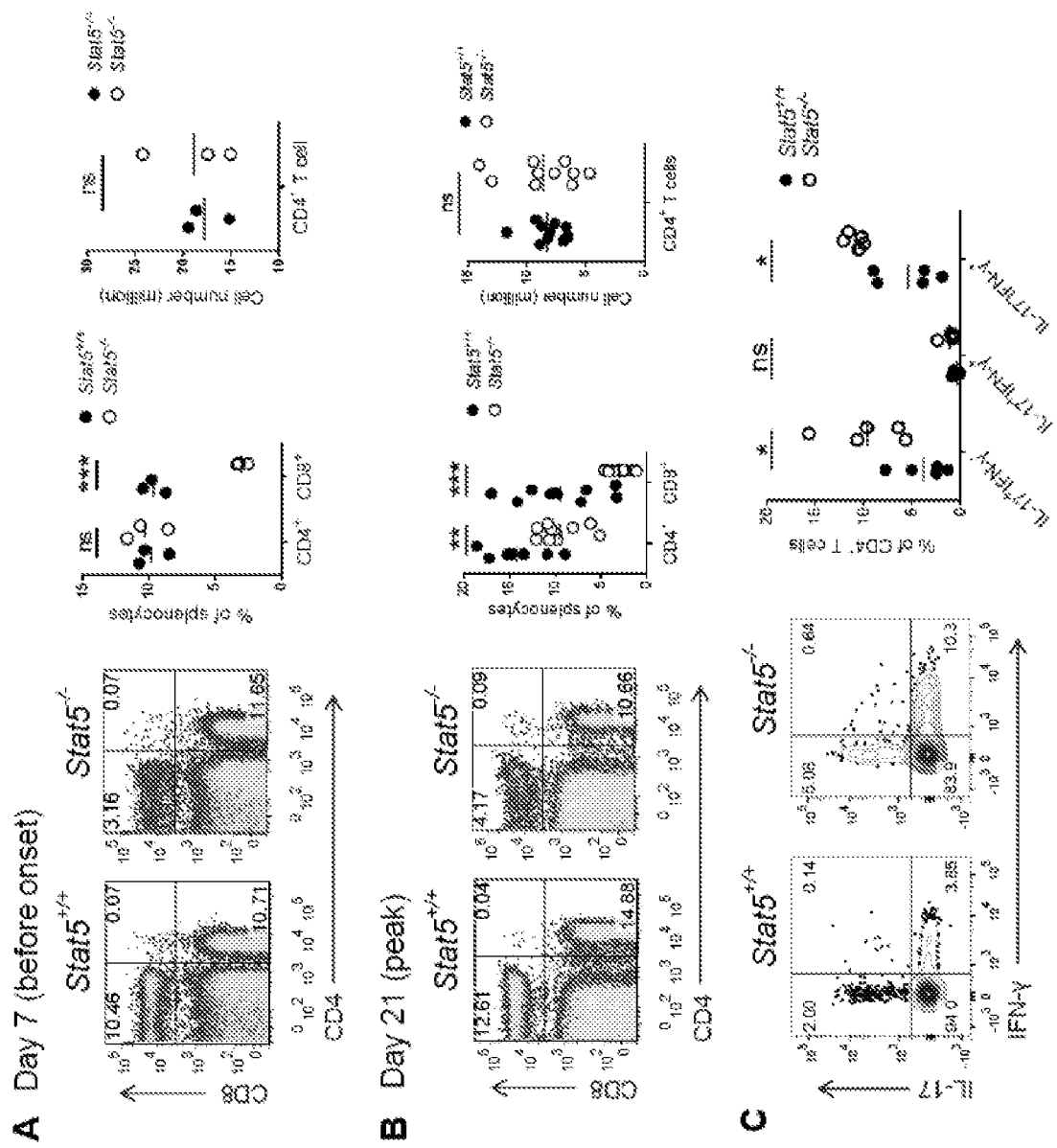
FIGS. 4A-4C depict conditional Stat5 mutant mice have no defect in CD4$^+$ T cell generation in periphery. Spleens were obtained from MOG$_{35-55}$/CFA-immunized Stat5$^{+/+}$ and Stat5$^{-/-}$ mice at day 7 (FIG. 4A) and day 21 (FIG. 4B). The proportions of CD4$^+$ and CD8$^+$ T cells were analyzed by flow cytometry. The absolute number of CD4$^+$ T cells was calculated (right panels). Data are representative of two independent experiments (FIG. 4A) or pooled from two independent experiments (FIG. 4B). IL-17 and IFN-γ expression by splenic CD4$^+$ T cells of Stat5$^{+/+}$ and Stat5$^{-/-}$ EAE mice was determined by intracellular cytokine staining (FIG. 4C). Data are representative of three independent experiments. *p<0.5, p<0.005, *p<0.0005.

Example 2. Resistance to EAE in Stat5-Mutant Mice is Due to an Intrinsic Defect of Antigen Specific CD4$^+$ T Cells Independent of $T_H1$ and $T_H17$ Generation Stat5 deletion (Cd4-cre; Stat5$^{f/-}$) mice was reported to develop peripheral lymphopenia, with a reduction of both CD4$^+$ and CD8$^+$ T cells (Yao et al., 2006). However, another study showed that Stat5 deletion (Cd4-cre; Stat5$^{f/f}$) did not affect the proportion of peripheral CD4$^+$ T cells (Burchill et al., 2007). In the experimental setting, a change in the absolute number of peripheral CD4$^+$ T cells was not detected by Stat5 deletion during EAE development (FIGS. 4A and 4B), suggesting the resistance to EAE in Stat5$^{-/-}$ mice was not caused by peripheral lymphopenia. Furthermore, increased frequencies of IL-17$^+$ and IFN-γ$^+$ cells were detected among CD4$^+$ T cells in spleens of Stat5$^{-/-}$ mice (FIG. 4C), which further support the idea that the resistance to EAE in Stat5$^{-/-}$ mice is likely independent of $T_H1$ and $T_H17$ generation. To validate the function of STAT5 in $T_H1$ and $T_H17$ generation, the in vitro differentiation was performed by activating naïve CD4$^+$ T cells under $T_H1$- and $T_H17$-polarizing conditions. In agreement with previous reports, that STAT5 mediated the suppressive effect of IL-2 on $T_H17$ differentiation (data not shown). Interestingly, IL-7, which also signals through STAT5, was not observed to have a demonstrable effect on $T_H17$ differentiation (data not shown). Nevertheless, a slight decrease of IFN-γ$^+$ cells under $T_H1$-polarizing condition was observed when STAT5 was deleted (data not shown).

To confirm if the resistance of EAE in Stat5$^{-/-}$ mice is mediated by CD4$^+$ T cells, Rag2$^{-/-}$ mice were reconstituted with Stat5$^{+/+}$ or Stat5$^{-/-}$ CD4$^+$ T cells followed by EAE induction. We found that Rag2$^{-/-}$ mice that received Stat5$^{-/-}$ CD4$^+$ T cells were resistant to the disease compared with mice receiving wild-type cells (data not shown), demonstrating that Stat5$^{-/-}$ CD4$^+$ T cells were impaired in their ability to promote EAE development.

Figures 5A, 5B, 5C, 5D:
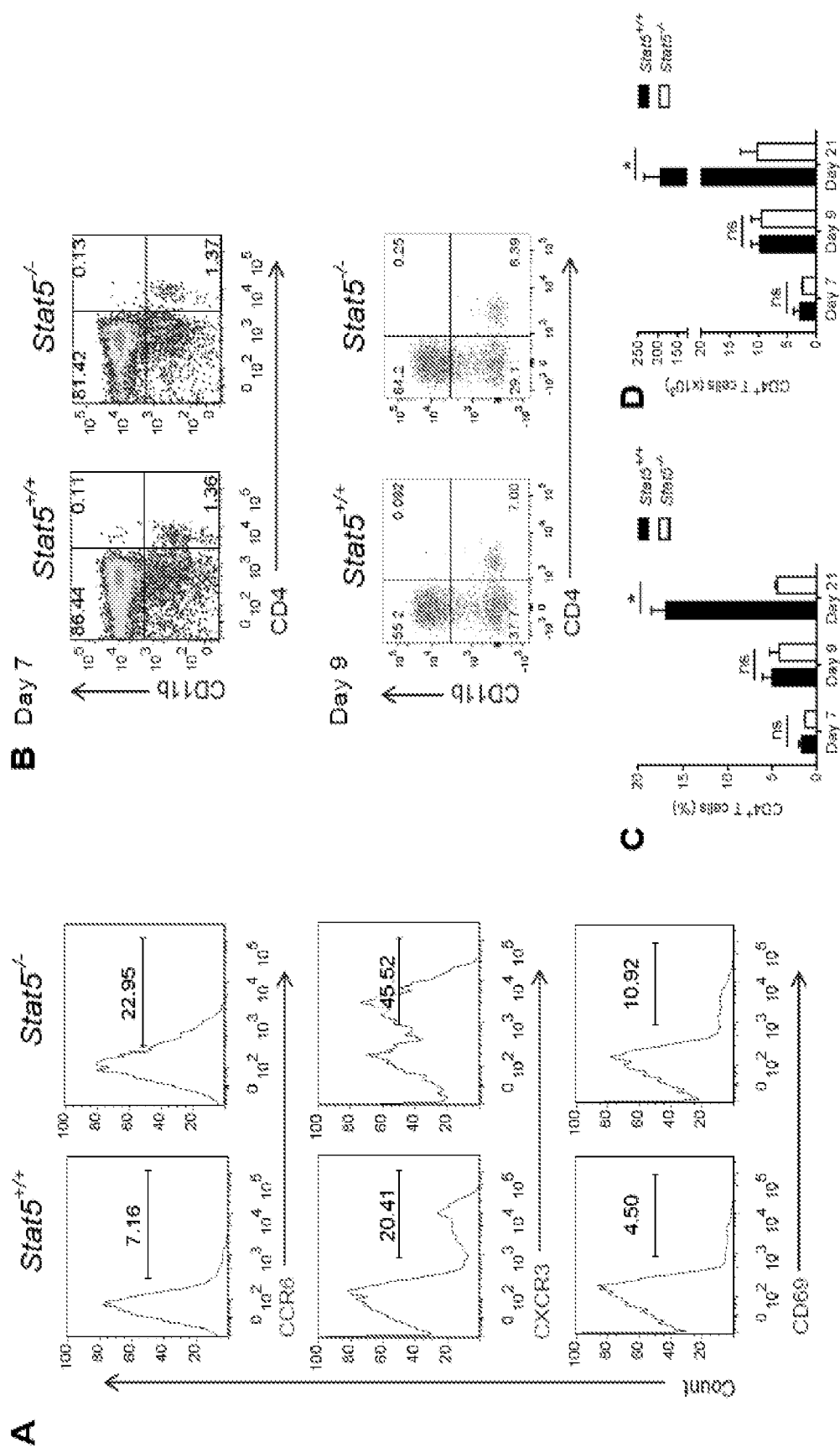
FIGS. 5A-5D depict Stat5-deficient CD4$^+$ T cells can infiltrate CNS but fail to induce effective neuroinflammation. CCR6, CXCR3 and CD69 expression by splenic CD4$^+$ T cells of Stat5$^{+/+}$ and Stat5$^{-/-}$ EAE mice was measured. Data are representative of two independent experiments with three to five mice per group (FIG. 5A). CNS-infiltrating CD4$^+$ T cells were analyzed at day 7, 9 and 21 after first MOG$_{35-55}$/CFA immunization (FIGS. 5B-5D). Cell numbers were calculated (FIG. 5D). Data are representative of two independent experiments with three mice per group. *p<0.5.

Next, whether the lack of encephalitogenicity was caused by defects in migration of Stat5$^{-/-}$ CD4$^+$ T cells to the CNS was examined. It has been shown that the chemokine receptor CCR6 is essential for T$_H$17 cell entry into the CNS through the choroid plexus (Reboldi et al., 2009). Thus, CCR6 expression in both Stat5$^{-/-}$ and Stat5$^{+/+}$ CD4$^+$ T cells was examined. Increased CD4$^+$CCR6$^+$ cells in spleens of Stat5$^{-/-}$ mice compared with Stat5$^{+/+}$ controls (FIG. 5A) was observed. CXCR3 and CD69 expression was also examined, which showed increased expression of both molecules in CD4$^+$ T cells in the absence of STAT5 (FIG. 5A). These results indicate that Stat5$^{-/-}$ CD4$^+$ T cells can infiltrate CNS. Furthermore, comparable number of CD4$^+$ T cells present in the CNS of Stat5$^{+/+}$ and Stat5$^{-/-}$ mice during EAE induction was observed (at day 7 and day 9) (FIG. 5B). However, CD4$^+$ T cells in CNS of Stat5$^{-/-}$ mice dropped dramatically during disease onset (Day 21) (FIGS. 5C and 5D). Together, these results demonstrate that Stat5$^{-/-}$ CD4$^+$ T cells can infiltrate CNS, but fail to induce effective inflammation in the CNS in EAE.

Figures 6A, 6B, 6C:
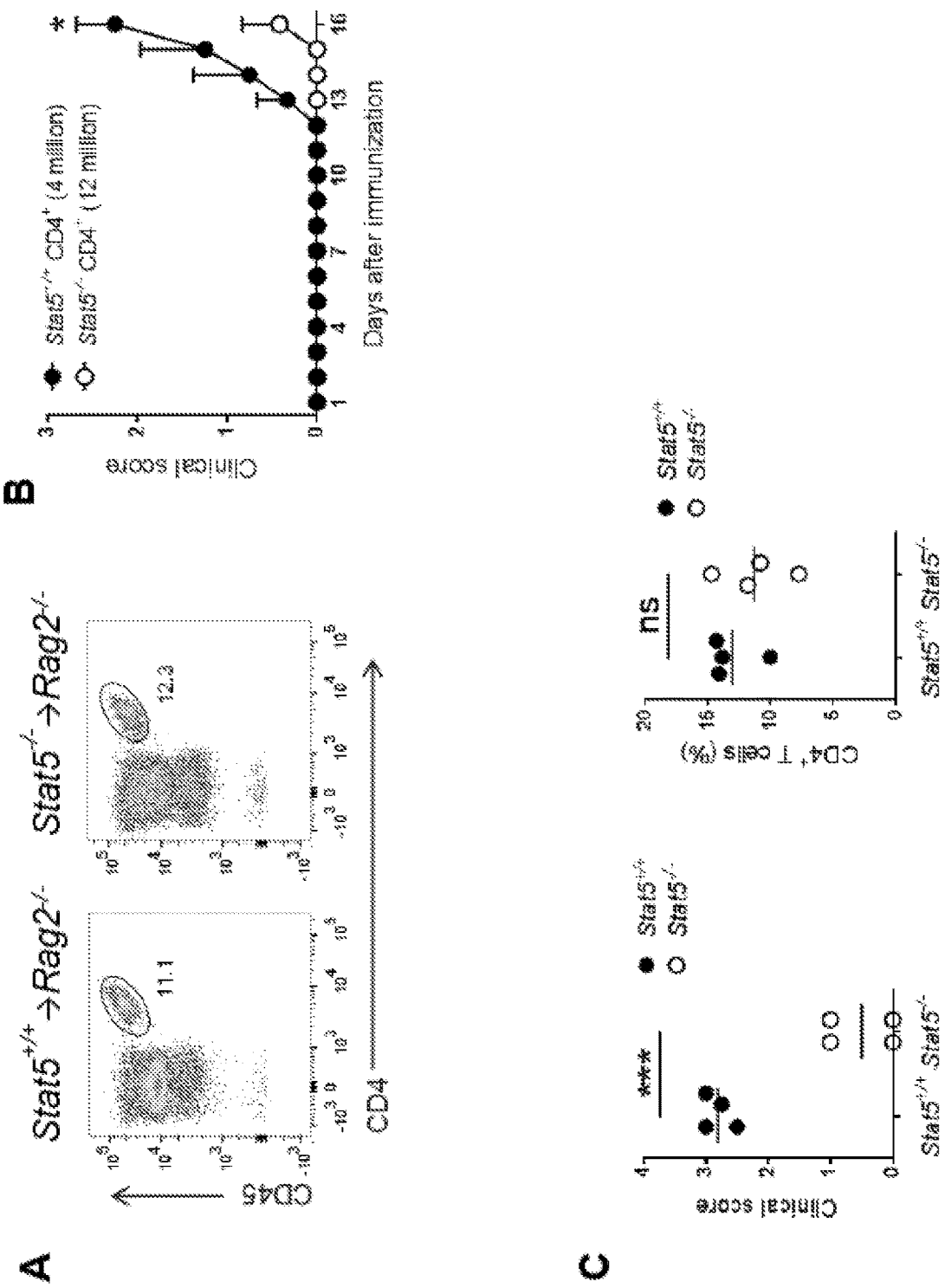
FIGS. 6A-6C show resistance to EAE in Stat5$^{-/-}$ mice is not caused by any defect in the survival of CD4$^+$ T cells in the absence of STAT5. CD4$^+$ T cell infiltration (FIG. 6A) and clinical scores (FIG. 6B) of Rag2$^{-/-}$ recipient mice transferred with different numbers of Stat5$^{+/+}$ and Stat5$^{-/-}$ CD4$^+$ T cells. Clinical scores and frequencies of CD4$^+$ T cells in the CNS at day 21 (disease peak) of EAE induction (FIG. 6C). *p<0.05, ***p<0.0005.

To further exclude the possibility that the resistance of Stat5-deficient mice to EAE was caused by any potential defect in the survival of autoreactive CD4$^+$ T in the CNS, increased numbers of Stat5$^{-/-}$ CD4$^+$ T cells than wild-type cells were transferred into Rag2$^{-/-}$ mice respectively to make sure comparable numbers of autoreactive CD4$^+$ T cells were present in the CNS during EAE development. As shown in FIGS. 6A and 6B, despite similar numbers of CD4$^+$ T cells in the CNS between two groups of mice, reduced disease severity was nevertheless observed in mice receiving Stat5-deficient CD4$^+$ T cells. Additionally, certain numbers of Stat5-deficient mice containing similar numbers of CD4$^+$ T cells in the CNS as wild-type mice at peak of EAE disease were observed, yet, they were relatively resistant to EAE compared with those wild-type mice (FIG. 6C), further suggesting that the resistance to EAE disease in Stat5-deficient mice was unlikely due to impaired CD4$^+$ T cell survival in the CNS.

Figures 7A, 7B, 7C:
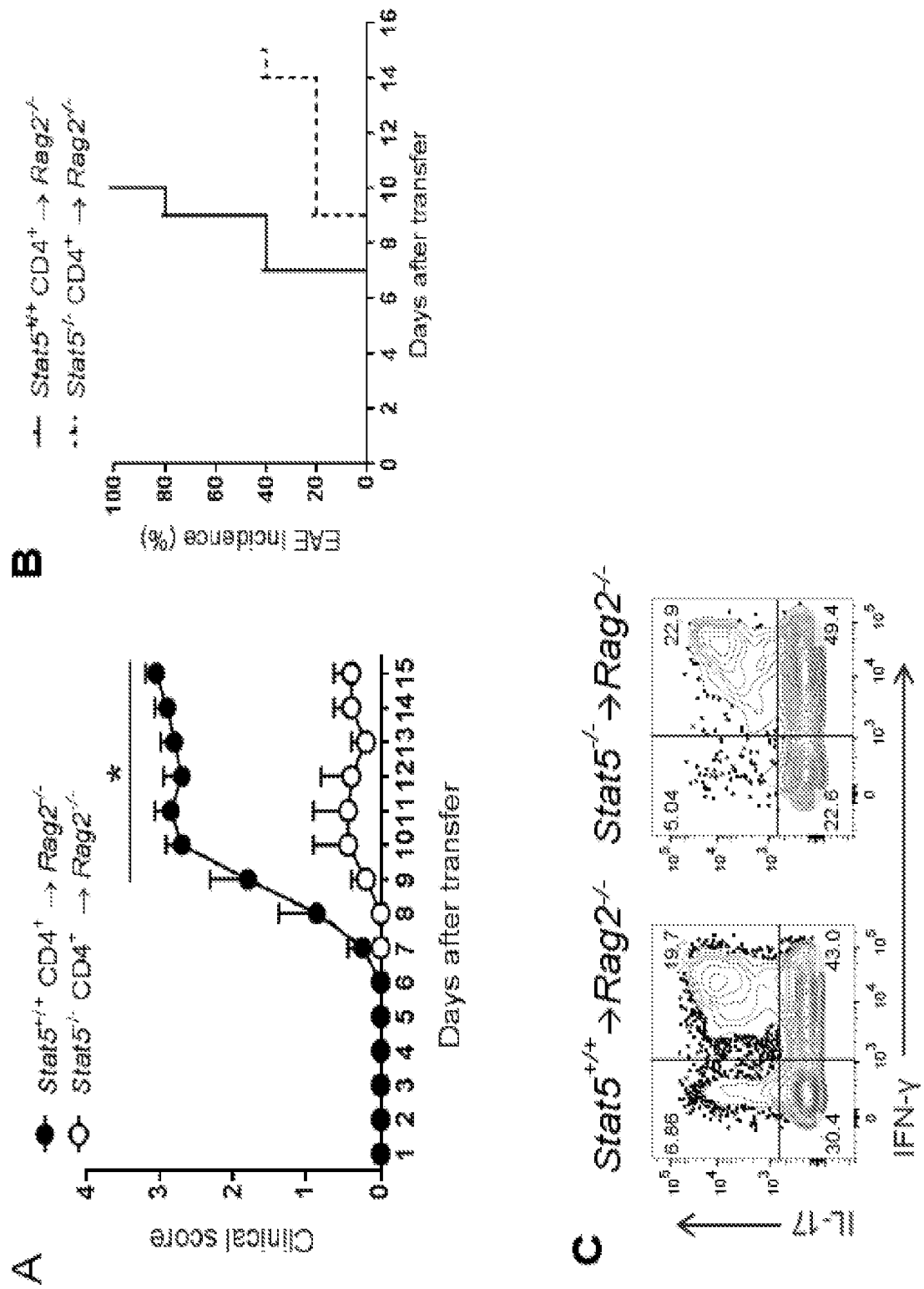
FIGS. 7A-7C depict the intrinsic defect of Stat5-deficient CD4$^+$ T cells in encephalitogenicity. Clinical EAE scores (FIG. 7A) and incidence (FIG. 7B) of Rag2$^{-/-}$ mice (n=5 per group) after adoptive transfer of 2 million MOG$_{35-55}$-specific Stat5$^{+/+}$ or Stat5$^{-/-}$ CD4$^+$ T cells respectively. IL-17 and IFN-γ expression by CNS-infiltrating CD4$^+$ T cells was measured at peak of disease (FIG. 7C). Data represent two independent experiments. *p<0.05.

To further develop a causal link between these observations and the intrinsic impairment of Stat5$^{-/-}$ CD4$^+$ T cells, MOG$_{35-55}$-specific Stat5$^{+/+}$ and Stat5$^{-/-}$ CD4$^+$ T cells were transferred into Rag2$^{-/-}$ mice separately without further immunization to test if these cells were able to mediate EAE development. As shown in FIGS. 7A and 7B, mice receiving Stat5$^{+/+}$ CD4$^+$ T cells spontaneously developed EAE disease 1 week after transfer. In contrast, mice receiving Stat5$^{-/-}$ CD4$^+$ T cells had significantly reduced disease severity and incidence. The frequencies of IL-17$^+$ and IFN-γ+ cells among CD4$^+$ T cells in the CNS of Rag2$^{-/-}$ mice were comparable between two groups (FIG. 7C), further suggesting that the intrinsic defect in encephalitogenicity of Stat5$^{-/-}$ CD4$^+$ T cells is independent of T$_H$1 and T$_H$17. To exclude the possible role of CD8$^+$ T cells in the resistance to EAE observed in Stat5$^{-/-}$ mice, Rag2$^{-/-}$ mice were reconstituted with MOG$_{35-55}$-specific Stat5$^{+/+}$ or Stat5$^{-/-}$ CD4$^+$ T cells together with equal numbers of Stat5$^{+/+}$ CD8$^+$ T cells. The transfer of Stat5$^{-/-}$ CD4$^+$ together with Stat5$^{+/+}$ CD8$^+$ T cells still failed to induce EAE (data not shown). Together, these data demonstrate that Stat5$^{-/-}$ CD4$^+$ T cells have intrinsic defect in encephalitogenicity. The relevant teachings of all patents, published applications and references cited herein are incorporated by reference in their entirety.

Example 3. Diminished Expression of GM-CSF in Stat5$^{-/-}$ CD4$^+$ T Cells

Figures 8A, 8B, 8C, 8D:
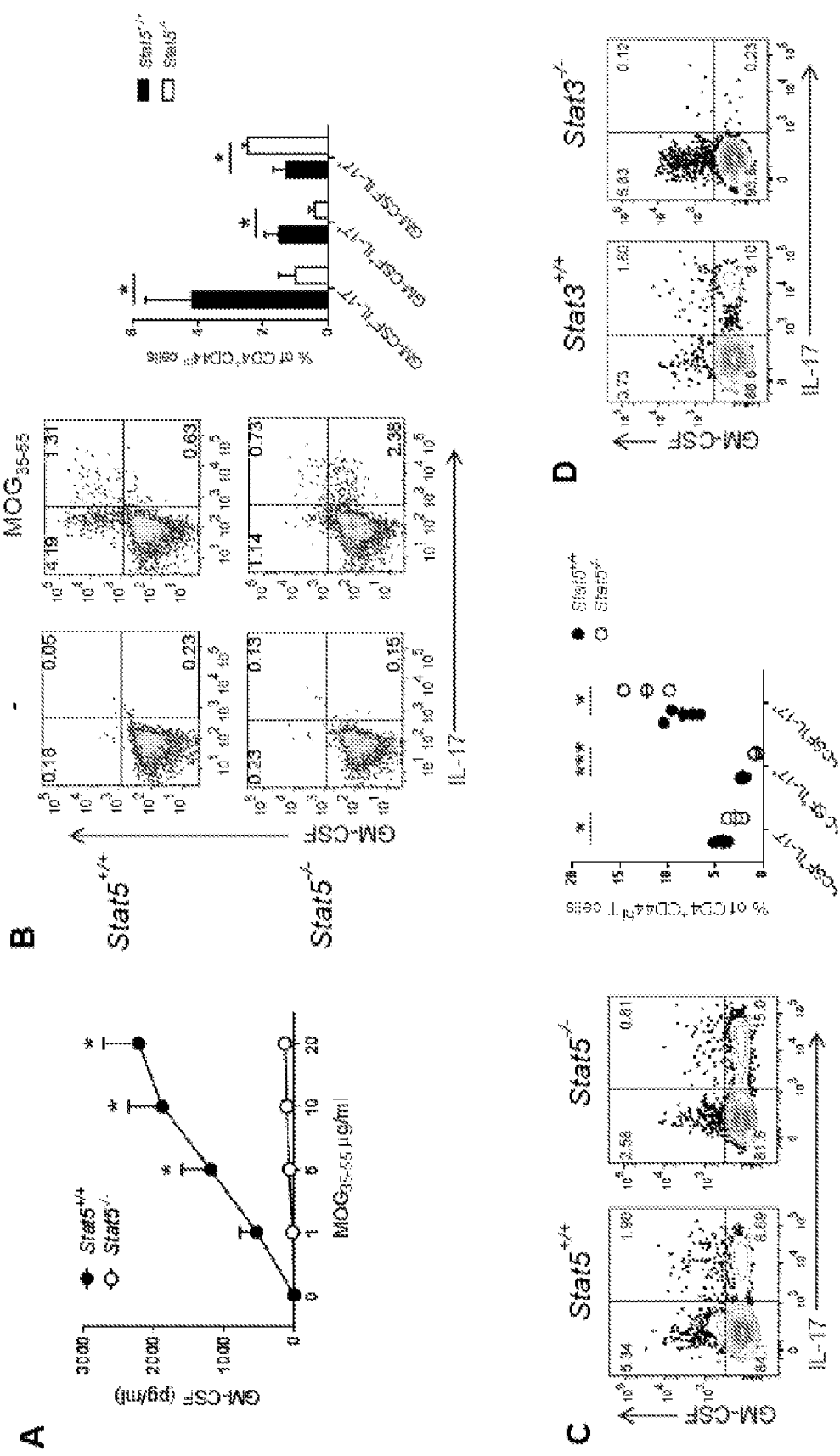
FIGS. 8A-8D depict the diminished induction of GM-CSF in splenic Stat5$^{-/-}$ CD4$^+$ T cells.

To test whether GM-CSF production was impaired by Stat5 deletion, its expression was examined in MOG$_{35-55}$-specific Stat5$^{+/+}$ and Stat5$^{-/-}$ CD4$^+$ T cells. Splenocytes derived from MOG$_{35-55}$/CFA-immunized Stat5$^{+/+}$ and Stat5$^{-/-}$ mice were challenged with various concentrations of MOG$_{35-55}$ for 24 h, to examine the secretion of GM-CSF. GM-CSF production was observed to increase in a MOG$_{35-55}$ dose-dependent manner in Stat5$^{+/+}$ cells (FIG. 8A). In contrast, GM-CSF production was severely diminished in Stat5$^{-/-}$ cells in all conditions. To further validate this, splenocytes derived from mice were stimulated during the development of EAE with PMA/Ionomycin in the presence of GolgiPlug for GM-CSF and IL-17 intracellular staining. Although IL-17 expression was enhanced in Stat5$^{-/-}$ cells, a significantly reduced proportion of GM-CSF$^+$IL-17$^-$ and GM-CSF$^+$ IL-17$^+$ cells was observed among CD4$^+$CD44$^{hi}$ cells in the absence of STAT5 (FIG. 8B). Moreover, the frequency of MOG$_{35-55}$-specific GM-CSF$^+$ T cells was also significantly reduced in spleens of Stat5$^{-/-}$ mice (FIG. 8C). Together, these results indicate that STAT5 is required for GM-CSF expression in autoreactive CD4$^+$ T cells. However, STAT3, an important transcription factor in T$_H$17 differentiation, was required for GM-CSF expression (FIG. 8D).

Figures 9A, 9B, 9C:
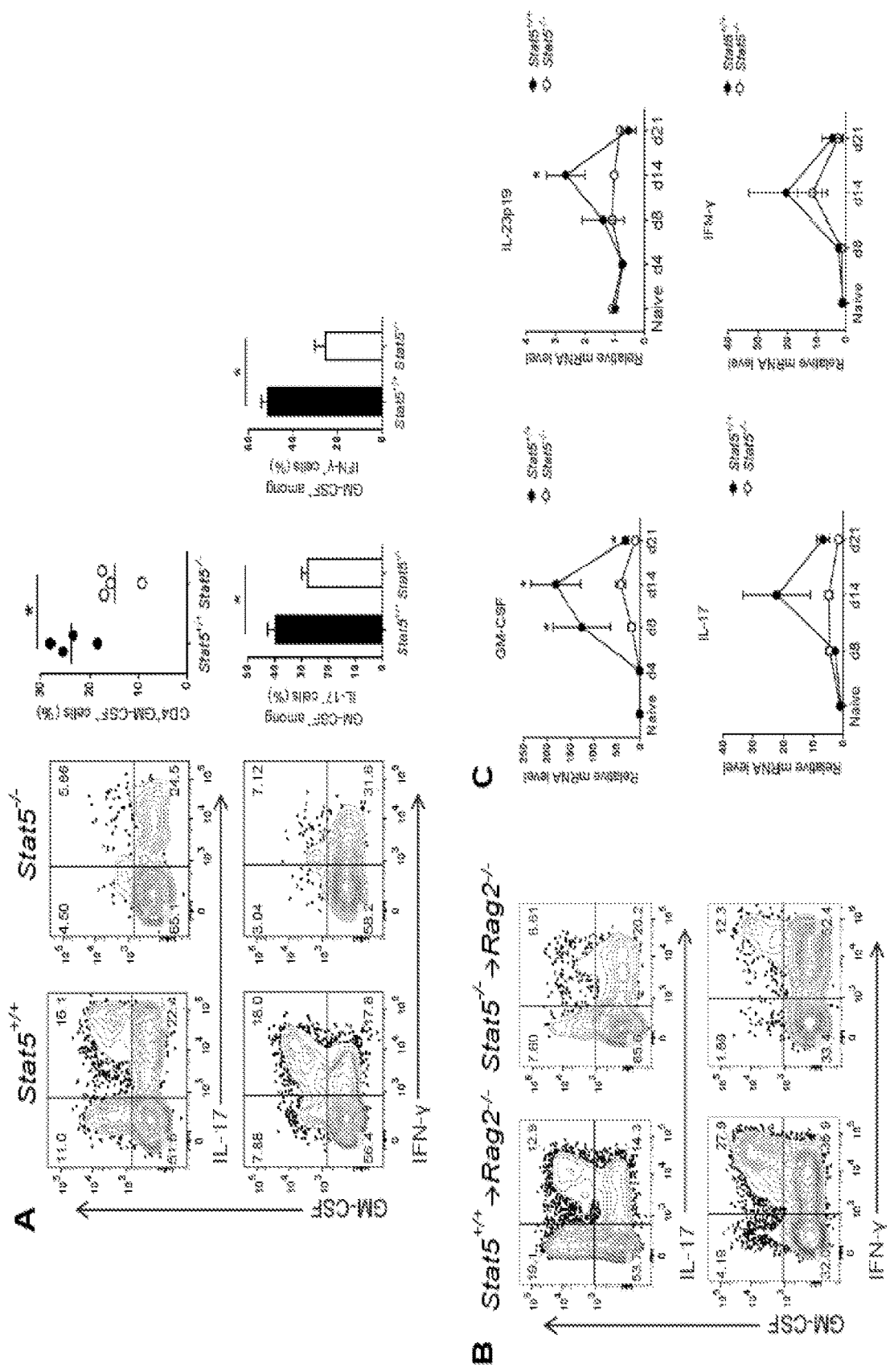
FIGS. 9A-9C depict the diminished induction of GM-CSF in CNS-infiltrating Stat5$^{-/-}$ CD4$^+$ T cells.

Next, GM-CSF induction in the CNS during EAE development was examined. Although IL-17 and IFN-γ production by CNS-infiltrating CD4$^+$ T cells was not impaired by Stat5 deficiency, a diminished frequency of CD4$^+$GM-CSF$^+$ cells in the CNS of Stat5$^{-/-}$ mice was detected compared with control mice (FIG. 9A). Further analysis showed a reduced GM-CSF$^+$ percentage among CD4$^+$IL-17$^+$ cells and among CD4$^+$IFN-γ$^+$ cells (FIG. 9A). Similarly, Rag2$^{-/-}$ mice transferred with MOG$_{35-55}$-specific Stat5$^{-/-}$ CD4$^+$ T cells also showed a reduced frequency of CD4$^+$GM-CSF$^+$ T cells in the CNS compared with control mice (FIG. 9B). GM-CSF mRNA expression in the CNS of Stat5$^{-/-}$ mice was markedly lower than that of Stat5$^{+/+}$ mice at day 8 after EAE induction (FIG. 9C), when comparable CD4$^+$ T cell infiltration was detected in Stat5$^{-/-}$ and Stat5$^{+/+}$ mice (FIGS. 5C and 5D). Meanwhile, no significant difference of IL-17 and IFN-γ expression was detected between Stat5$^{-/-}$ and Stat5$^{+/+}$ mice (FIG. 9C). The impaired cytokine induction (IL-17 and IFN-γ) in the CNS of Stat5$^{-/-}$ mice at later stage (day 14, FIG. 9C) could be explained by the inability of Stat5$^{-/-}$ CD4$^+$ T to sustain neuroinflammation (FIGS. 5C and 5D). Interestingly, GM-CSF induction in the CNS preceded IL-23 induction (FIG. 9C), suggesting IL-23 might not be required for GM-CSF expression in the induction phase of EAE. In summary, the results suggest that GM-CSF expression in autoreactive CD4$^+$ T cells is regulated by STAT5 and the impaired GM-CSF production in the absence of STAT5 caused the resistance of the mice to EAE.

Figures 11A, 11B, 11C:
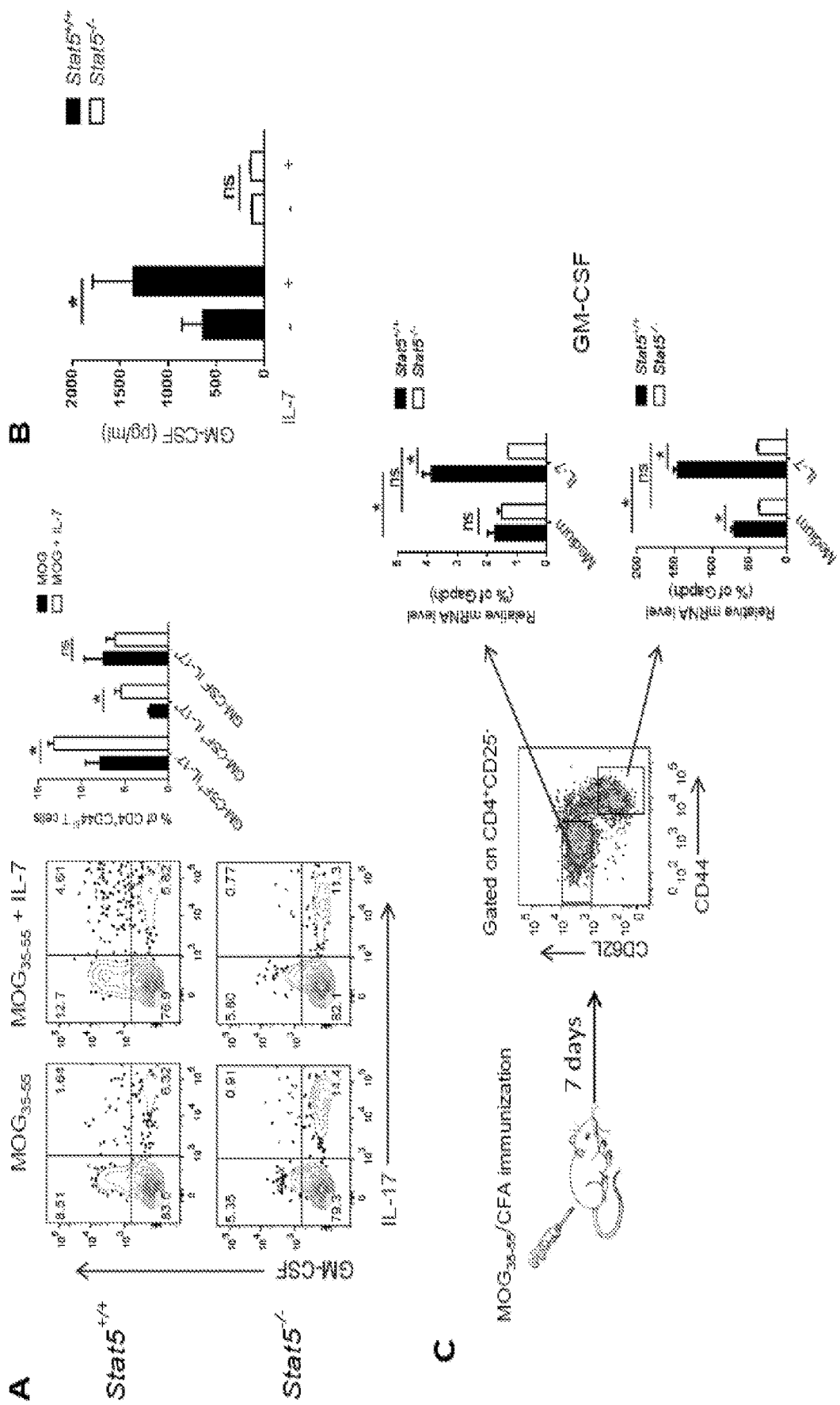
FIGS. 11A-11C depict IL-7-induced STAT5 activation promotes GM-CSF expression in autoreactive CD4$^+$ T cells. Splenocytes were obtained from MOG$_{35-55}$/CFA-immunized Stat5$^{+/+}$ and Stat5$^{-/-}$ mice before disease onset and challenged with MOG$_{35-55}$ (20 µg/ml) in the absence or presence of IL-7 for 48 h. Frequencies of GM-CSF$^+$ and IL-17$^+$ cells among CD4$^+$CD44$^{hi}$ T cells were measured by flow cytometry (FIG. 11A). GM-CSF secretion was measured by ELISA (FIG. 11B). Data represent two independent experiments with two to three mice per group. Splenic CD62L$^{hi}$CD44$^{lo}$ and CD62L$^{lo}$CD44$^{hi}$ T cells from MOG$_{35-55}$/CFA-immunized mice were sorted out. Cells were stimulated with anti-CD3 and anti-CD28 in the absence or presence of IL-7 for 4 h and then harvested for the analysis of GM-CSF expression by RT-PCR (FIG. 11C). *p<0.05

Example 4. IL-7-STAT5 Signaling Induces GM-CSF Expression in Autoreactive CD4$^+$ T Cells and Contributes to Neuroinflammation Next, the mechanism by which STAT5 regulates GM-CSF expression was investigated. As the present disclosure indicates, neither IL-23 nor IL-1β seemed to be potent STAT5 stimulators (FIG. 10A). Furthermore, IL-1R1 expression was not changed, whereas IL-23Rα expression was increased in Stat5$^{-/-}$ CD4$^+$ T cells (FIG. 10B). These data suggest that the ability of STAT5 to induce GM-CSF expression is likely independent of IL-23 and IL-1β signaling. In contrast, both IL-2 and IL-7 potently activated STAT5 by inducing tyrosine phosphorylation (FIG. 10A). Therefore, the effect of these two cytokines on GM-CSF induction in autoreactive T cells was further examined. Splenocytes derived from MOG$_{35-55}$-immunized wild-type mice were challenged with MOG$_{35-55}$ alone or plus IL-2. GM-CSF and IL-17 production by CD4$^+$ T cells were analyzed by intracellular cytokine staining. As shown in FIG. 10C, IL-2 showed modest effects on the frequency of GM-CSF$^+$ T cells. In contrast, IL-7 significantly promoted GM-CSF expression in both IL-17$^-$ and IL-17$^+$ CD4$^+$CD44$^{hi}$ T cells (FIG. 11A). Furthermore, IL-7 carried out this function in a STAT5-dependent manner, as Stat5 deletion abrogated its effect on GM-CSF expression as assessed by intracellular cytokine staining and ELISA (FIG. 11A, lower panels, and FIG. 11B).

IL-7Rα is expressed in both CD62L$^{hi}$CD44$^{lo}$T cells and CD62L$^{lo}$CD44$^{hi}$ T cells, suggesting IL-7 may directly act on CD4$^+$ T cells to regulate GM-CSF expression. Thus, CD62L$^{hi}$CD44$^{lo}$ and CD62L$^{lo}$CD44$^{hi}$ T cells were sorted from Stat5$^{-/-}$ mice and littermate controls during EAE development, and then activated cells in the presence or absence of IL-7. As shown in FIG. 11C, CD62L$^{lo}$CD44$^{hi}$ T cells potently expressed GM-CSF, while CD62L$^{hi}$CD44$^{lo}$ T cells expressed 30-fold lower GM-CSF amounts. STAT5 deletion resulted in reduced basal GM-CSF production in CD62L$^{lo}$CD44$^{hi}$ T cells. As expected, IL-7 promoted GM-CSF expression in both subsets of CD4$^+$ T cells in a STAT5-dependent manner (FIG. 11C).

Figures 12A, 12B, 12C, 12D:
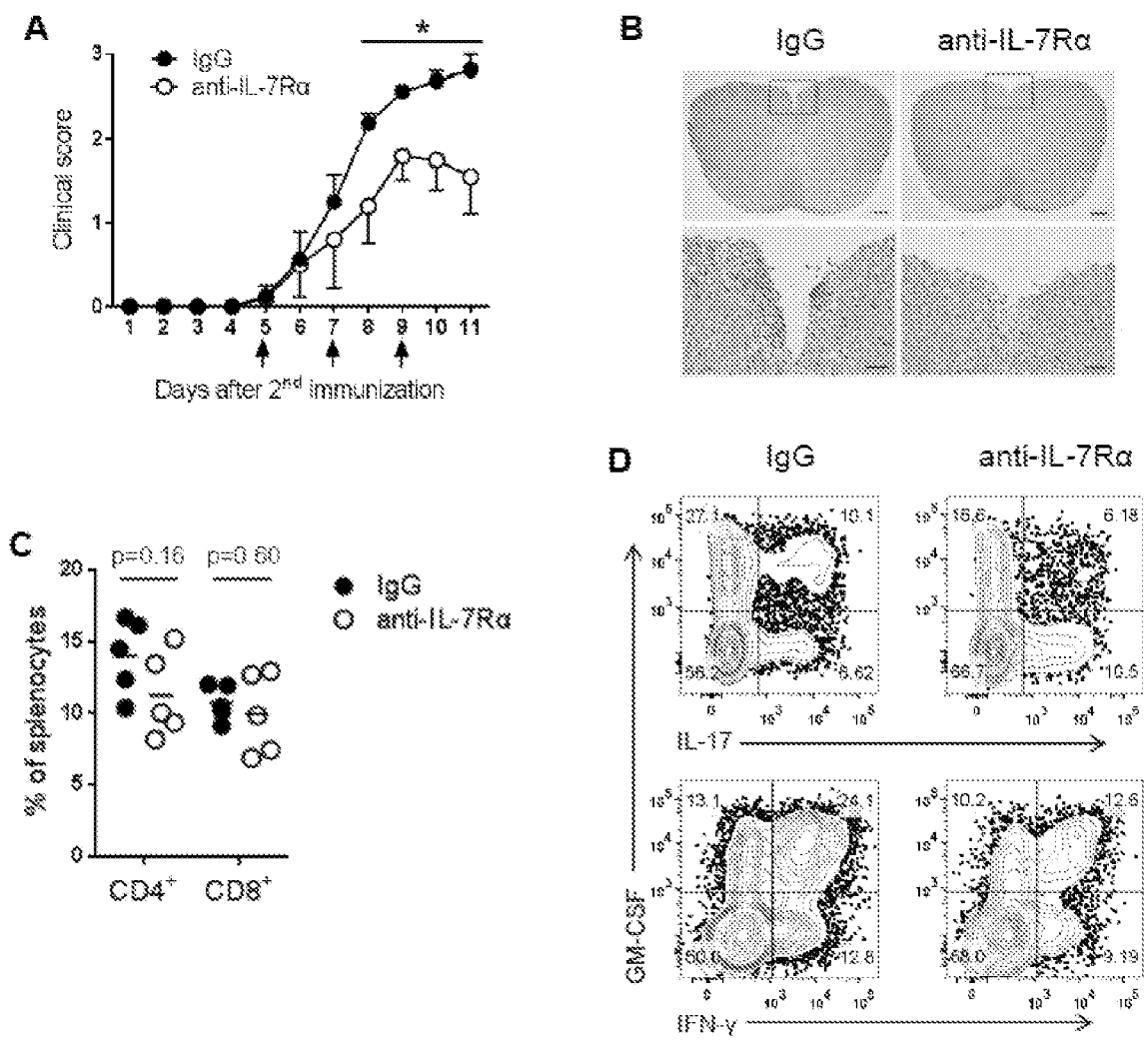
FIGS. 12A-12F depict IL-7Rα neutralization attenuates GM-CSF expression and ameliorates EAE. Clinical scores of EAE mice (n=5) treated with anti-IL-7Rα or normal IgG given every other day from day 5 after $2^{nd}$ immunization, as indicated by arrows. Data represent two independent experiments (FIG. 12A). Spinal cord sections were obtained from EAE mice at day 11 after $2^{nd}$ immunization. Immune cell infiltration was assessed histologically. Images shown are representative of three individuals per group. Scale bars, 200 µm (top), 50 µm (FIG. 12B, bottom). The percentages of CD4+ and CD8+ T cells in spleens of EAE mice. Data represent two independent experiments (FIG. 12C).
Figure 12E:
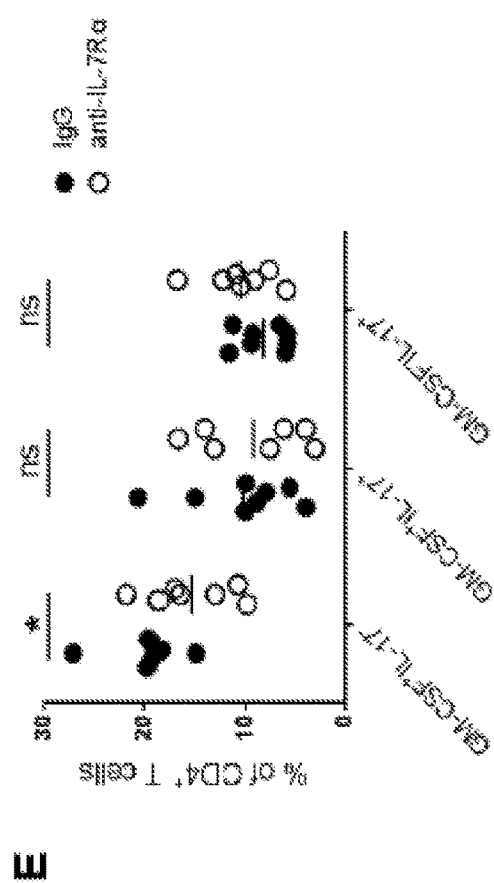
Figure 12F:
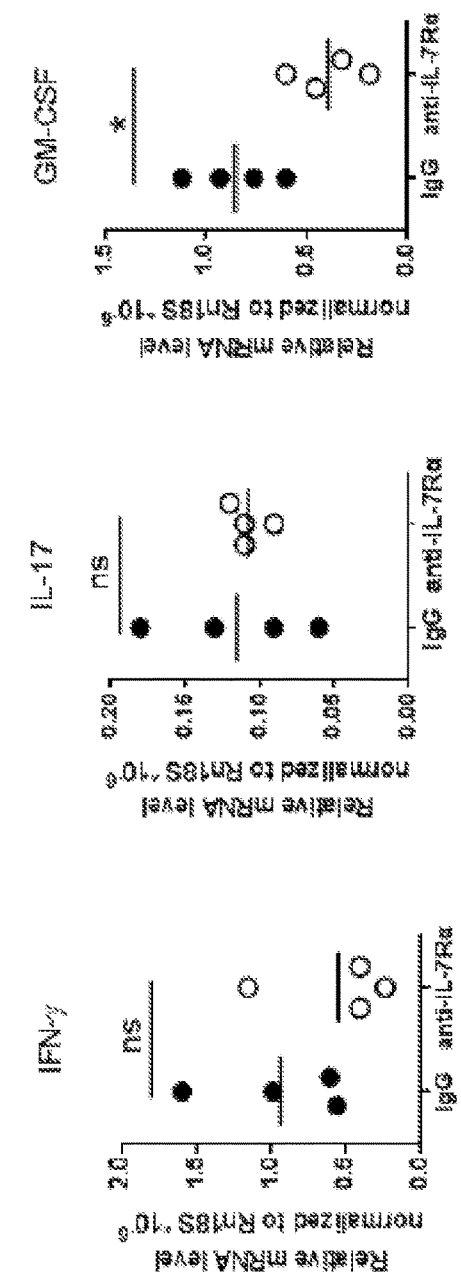

To examine the contribution of IL-7-induced GM-CSF expression in autoreactive CD4$^+$ T cells to EAE development, mice were treated with IL-7Rα-specific antibody (clone SB/14) during EAE development. The treatment resulted in a significant reduction of disease severity, which was accompanied with reduced CNS inflammation (FIGS. 12A and 12B). In agreement with previous report (Lee et al., 2012), this neutralizing antibody did not have T cell depleting activity (FIG. 12C). Notably, the blocking of IL-7 signaling resulted in decreased GM-CSF expression in CNS-infiltrating CD4$^+$ T cells (FIGS. 12D-12F). In summary, the present findings indicate that IL-7 induces STAT5-dependent GM-CSF expression in autoreactive CD4$^+$ T cells, which contributes to the development of neuroinflammation.

Example 5. GM-CSF-Expressing T$_H$ Cells are Distinct from T$_H$17 and T$_H$1

Figures 13A, 13B:
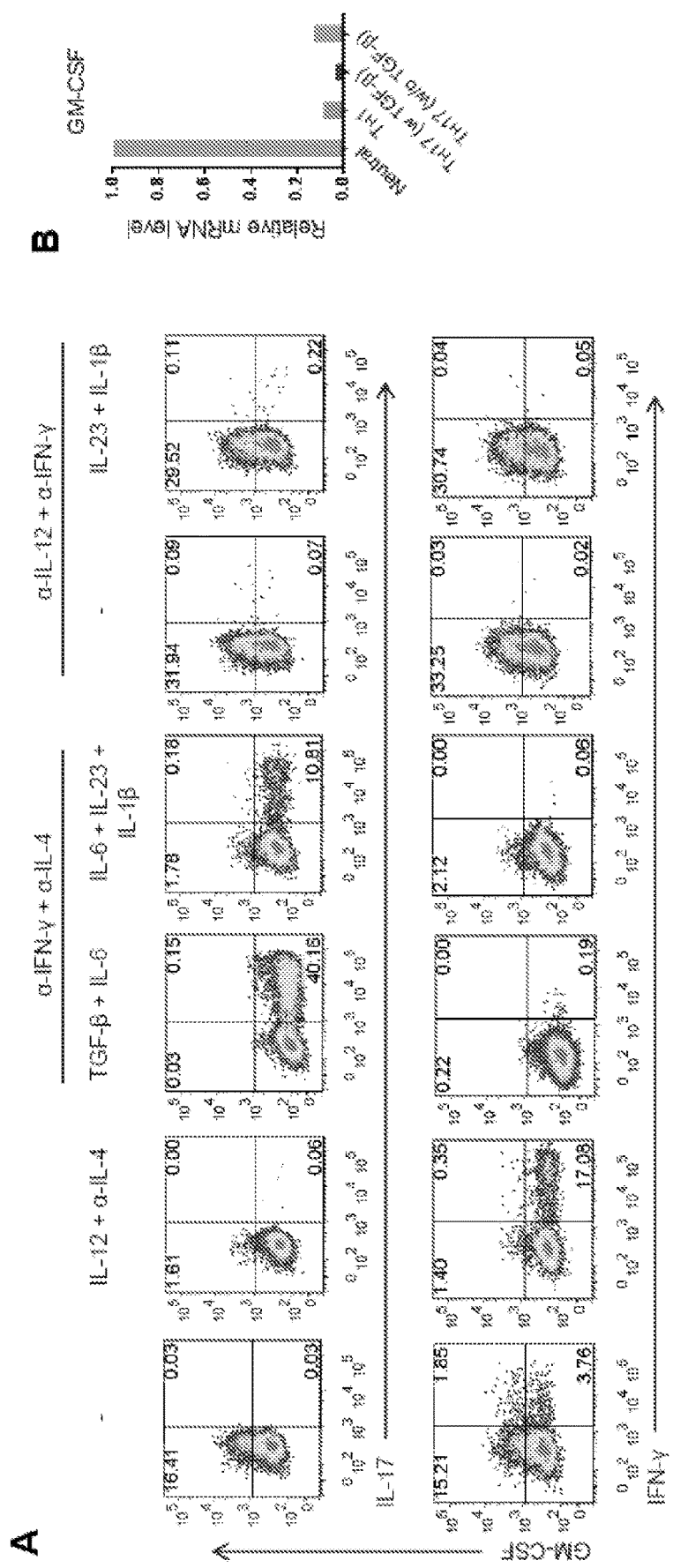
FIGS. 13A and 13B depict the differentiation of GM-CSF-expressing $T_H$ cells is distinct from $T_H17$ and $T_H1$. Naïve CD4+ T cells were primed with plate-bound anti-CD3 and soluble anti-CD28 in the presence of a combination of various cytokines and neutralizing antibodies as indicated. GM-CSF, IL-17 and IFN-γ expression was analyzed by intracellular staining (FIG. 13A) or RT-PCR (FIG. 13B)
Figures 14A, 14B, 14C, 14D:
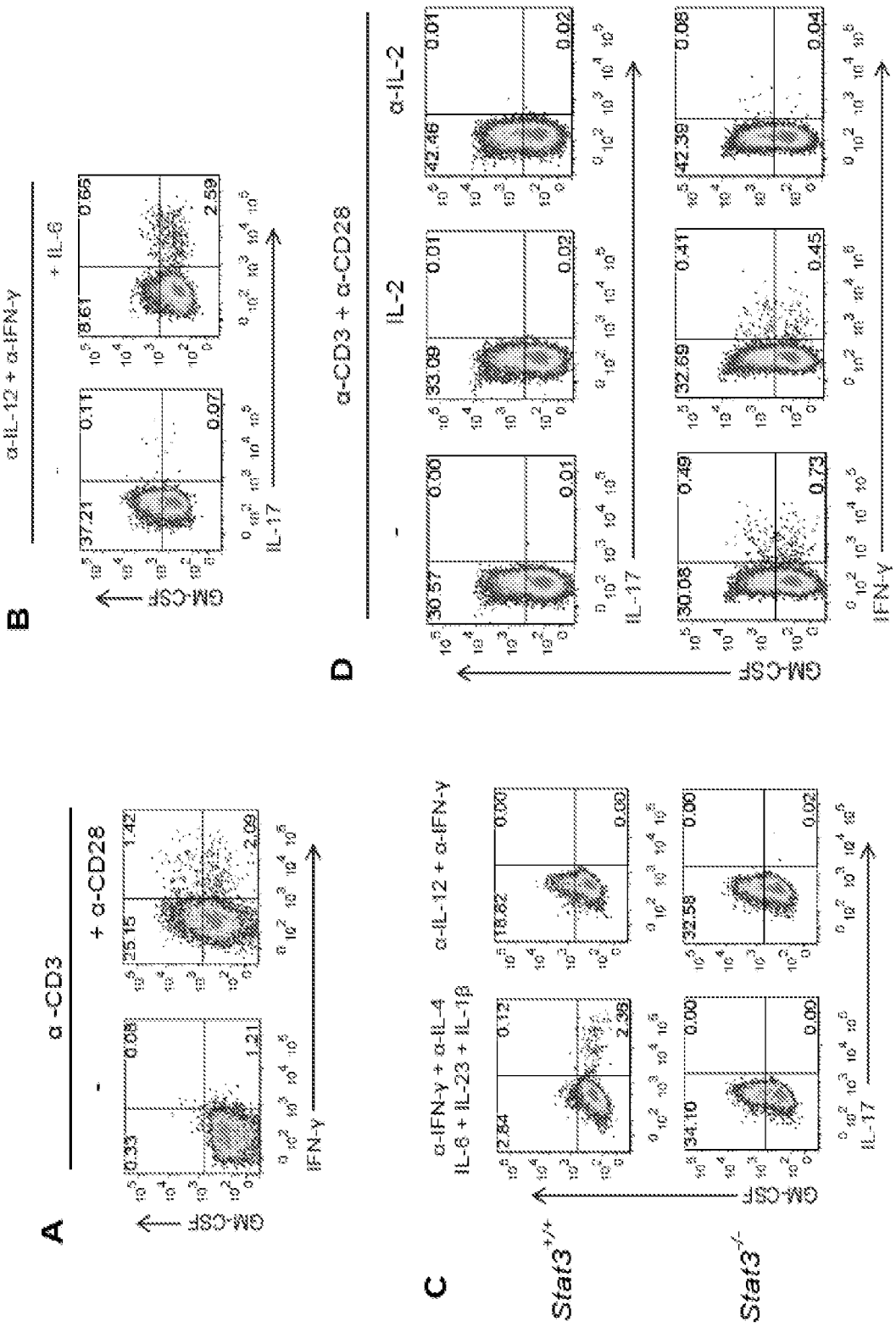
FIGS. 14A-14D show the effect of IL-2 and IL-6 on $T_H$-GM differentiation from naïve T cells. GM-CSF and IFN-γ expression in naïve CD4+ T cells activated for 72 h with anti-CD3 alone or plus anti-CD28 (FIG. 14A).

Since both T$_H$17 and T$_H$1 can produce GM-CSF, it was determined if the IL-7-stimulated phenotype was related to either of these subsets. To further understand the characteristics of GM-CSF-expressing CD4$^+$ cells, naïve CD4$^+$ T cells were stimulated with plate-bound anti-CD3 and soluble anti-CD28 under T$_H$1- or T$_H$17-polarizing conditions. It was observed that anti-CD3 together with anti-CD28 induced the expression of GM-CSF (FIG. 14A). However, while T$_H$1 differentiation conditions promoted IFN-γ expression and T$_H$17 conditions promoted IL-17 expression as expected, both T$_H$1 and T$_H$17 differentiation conditions greatly suppressed the production of GM-CSF (FIGS. 13A and 13B). Conversely, IL-12 and IFN-γ neutralization promoted GM-CSF-expressing cell generation (FIG. 13A), consistent with a previous report (Codarri et al., 2011). IL-23 and IL-1β did not increase GM-CSF-expressing cell differentiation from naïve CD4$^+$ T cells (FIG. 13A), which was consistent with the finding that naïve CD4$^+$ T cells did not express their receptors. TGF-β inhibits GM-CSF expression (El-Behi et al., 2011). IL-6, an essential cytokine for T$_H$17 differentiation, had a profound inhibitory effect on GM-CSF expression (FIG. 14B), indicating STAT3 could be a negative regulator. To address this, naïve CD4$^+$ T cells were purified from Stat3$^{-/-}$ mice for cell differentiation. Strikingly, in the absence of STAT3, cells polarized under T$_H$17 condition expressed GM-CSF (FIG. 14C). Interestingly, even without exogenous IL-6, STAT3 still had a moderate suppressive effect on GM-CSF-expressing cell differentiation (FIG. 14C). In addition, RORγt and T-bet have been reported unnecessary for GM-CSF expression in CD4$^+$ T cells (El-Behi et al., 2011). Thus, the present datasupport a model wherein GM-CSF-expressing CD4$^+$ T cells develop via a lineage distinct from T$_H$17 and T$_H$1.

Example 6. IL-7-STAT5 Programs GM-CSF-Expressing T$_H$ Cell Differentiation

Figures 15A, 15B:
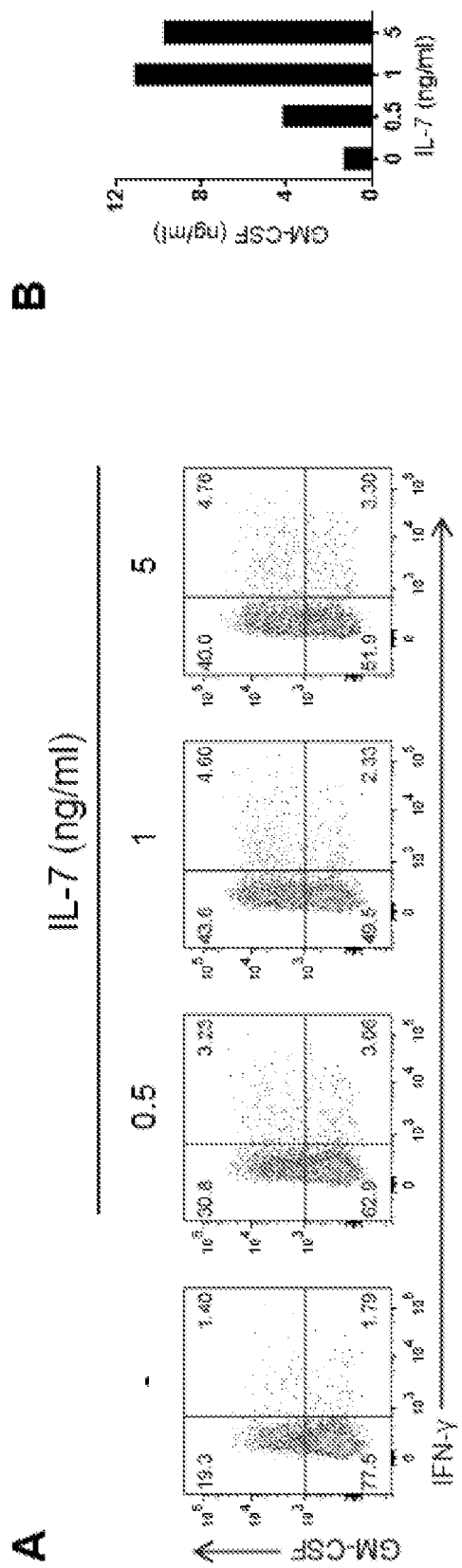
FIGS. 15A-15F depict IL-7-STAT5 signaling programs $T_H$-GM differentiation from naïve precursor cells. Naïve CD4+ T cells were primed with plate-bound anti-CD3 and soluble anti-CD28 in the presence of various concentration of IL-7 as indicated. GM-CSF and IFN-γ expression was analyzed by intracellular staining (FIG. 15A) or ELISA (FIG. 15B).
Figures 15C, 15D, 15E, 15F:
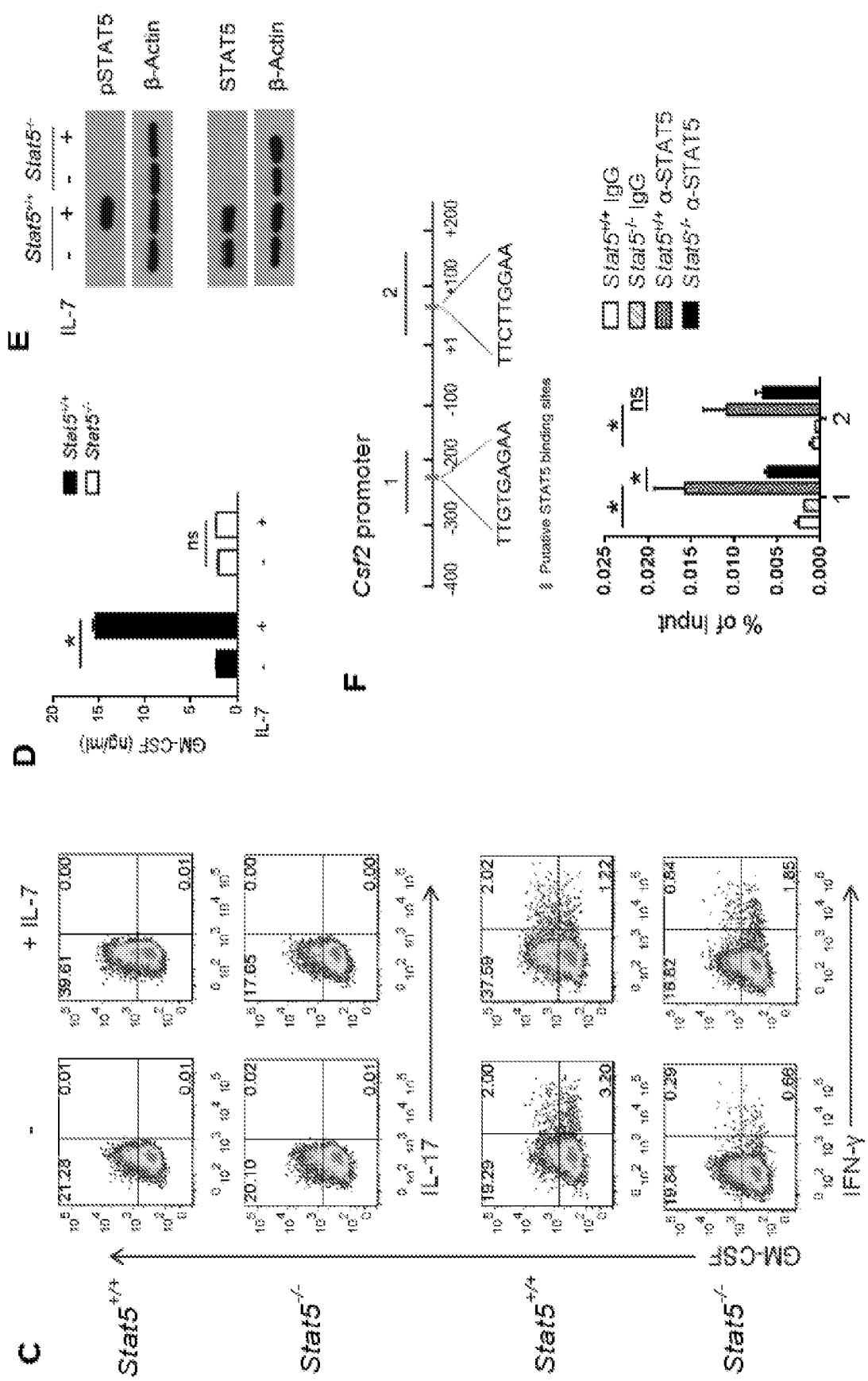

The present findings disclosed herein (including. g., diminished GM-CSF expression in Stat5$^{-/-}$ CD4$^+$ T cells in vivo, IL-7/STAT5-mediated induction of GM-CSF expression in naïve CD4$^+$ T cells, and the distinct features of GM-CSF-expressing T$_H$ cells versus T$_H$1 and T$_H$17 cells) indicates a distinct T$_H$ cell subset that is regulated by IL-7-STAT5 signaling. This finding was further explored by examining GM-CSF-expressing T$_H$ cell differentiation in vitro by activating naïve CD4$^+$ T cells with anti-CD3 and anti-CD28 in the presence of different concentrations of IL-7. As shown in FIGS. 15A and 15B, IL-7 strongly promoted the generation of GM-CSF-expressing cells and GM-CSF secretion. Moreover, the generation of GM-CSF-expressing T$_H$ by IL-7 was mediated by STAT5. Without STAT5, IL-7 was unable to promote the generation of GM-CSF-expressing cells (FIGS. 15C and 15D). Further investigation showed that IL-7-induced STAT5 activation directly bound promoter regions of the Csf2 gene (FIGS. 15E and 15F).

Figure 16A:
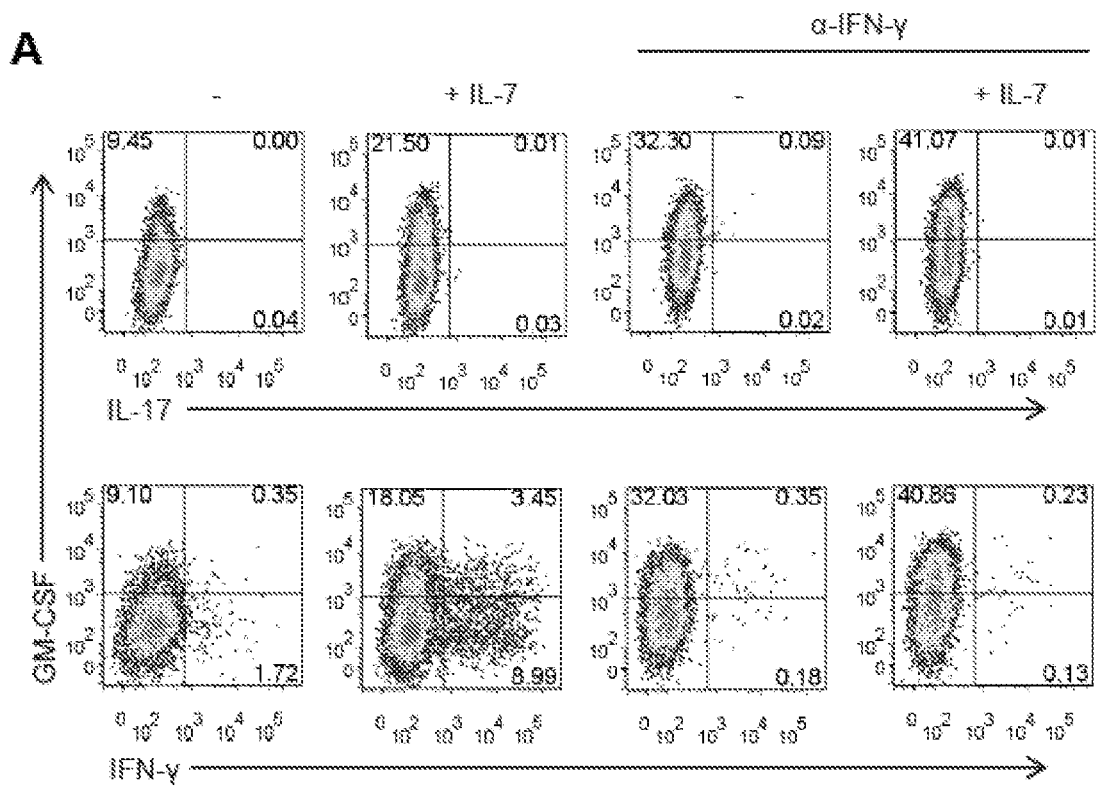
FIGS. 16A and 16B depict the differentiation conditions for $T_H$-GM subset. Naïve CD4+ T cells were activated with anti-CD3 and anti-CD28 in the presence of IL-7 or/and anti-IFN-γ as indicated. GM-CSF, IL-17 and IFN-γ expression was analyzed (FIG. 16A). The mRNA expression of T-bet and RORγt in naïve, $T_H1$ (IL-12+anti-IL-4), $T_H17$ (TGF-β+IL-6+anti-IFN-γ+anti-IL-4) and $T_H$-GM cells (IL-7+anti-IFN-γ) (FIG. 16B). The RT-PCR data were normalized to Gapdh, and expression in naïve T cells was set to 1.
Figure 16B:
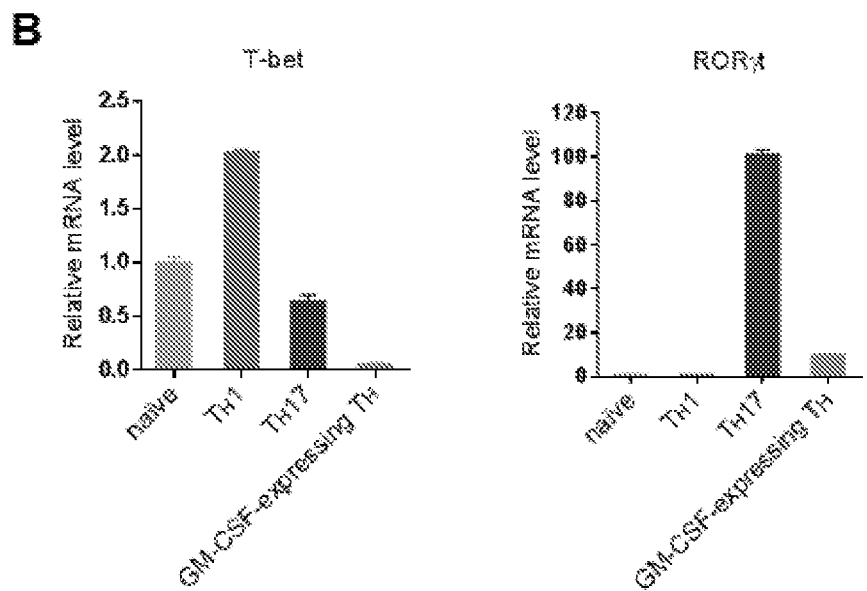

Small proportions of IFN-γ-expressing cells were generated during GM-CSF-expressing T$_H$ differentiation (FIG. 15A). Thus, the effect of blocking IFN-γ on GM-CSF-expressing cell generation was tested, which showed that the combination of IL-7 and IFN-γ neutralization induced the highest frequency of GM-CSF$^+$ cells, where few IL-17$^+$ or IFN-γ$^+$ cells were detected (FIG. 16A). Moreover, the expression of subset defining transcriptional factors in GM-CSF-expressing T$_H$ was examined and observed that the expression of RORγt or T-bet in GM-CSF-expressing T$_H$ was significantly lower than those in T$_H$17 or T$_H$1 cells, respectively (FIG. 16B), confirming that the GM-CSF-expressing T$_H$ cells are distinct from T$_H$1 and T$_H$17 cells. Together, these data suggest that IL-7-STAT5 signaling direct the differentiation of a novel GM-CSF-expressing helper T cell subset, termed T$_H$-GM.

Figures 17A, 17B, 17C, 17D, 17E:
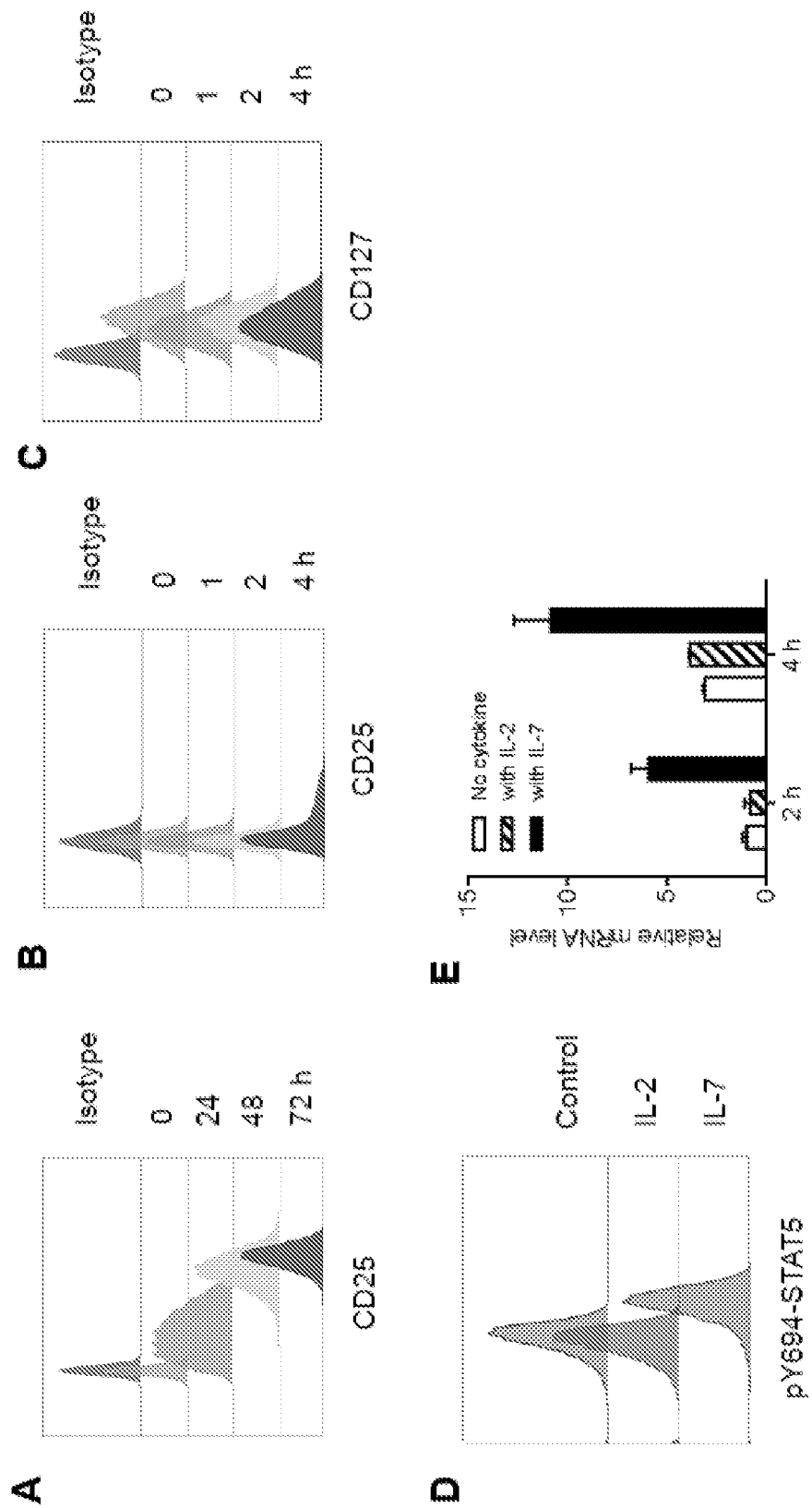
FIGS. 17A-17E illustrate that IL-7 but not IL-2 induces STAT5 activation and GM-CSF expression in naïve CD4+ T cells.
Figures 18A, 18B, 18C:
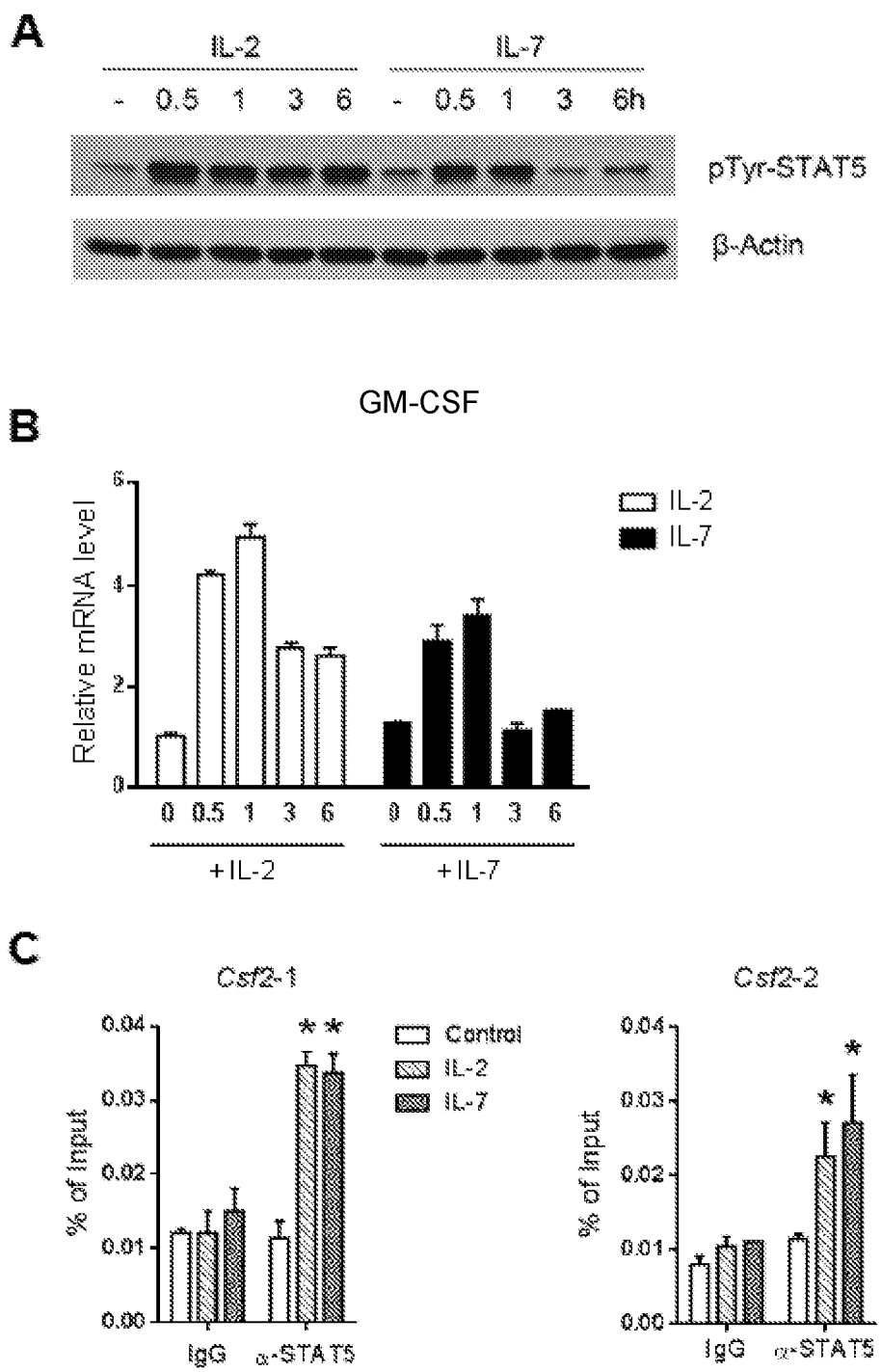
FIGS. 18A-18C show that both IL-2 and IL-7 can induce STAT5 activation and GM-CSF expression in activated CD4+ T cells.

Next, it was determined whether IL-2 signaling could influence T$_H$-GM differentiation from naïve CD4$^+$ T cells. The addition of IL-2 or antibody against IL-2 only had modest effect on the frequency of GM-CSF$^+$ cells (FIG. 14D), indicating a minimal effect of IL-2 on T$_H$-GM differentiation. Unlike IL-7Rα, IL-2 high-affinity receptor IL-2Rα was not expressed in naïve CD4$^+$ T cells, but its expression was gradually induced by TCR activation (FIGS. 17A-17C). Thus, the minimal effect of IL-2 at least in part is due to the unresponsiveness of naïve CD4$^+$ T cells to IL-2 stimulation. In support of this view, IL-7, but not IL-2, induced STAT5 activation and upregulated GM-CSF mRNA expression in naïve CD4$^+$ T cells (FIGS. 17D and 17E). To further confirm this idea, activated CD4$^+$ T cells were stimulated with IL-2 or IL-7, which showed that both cytokines induced STAT5 activation, Csf2 promoter binding and GM-CSF mRNA upregulation (FIGS. 18A-18C). Notably, IL-2 induced a prolonged STAT5 activation compared with IL-7 (FIG. 18A).

Example 7. Distinct Gene Expression Profile of T$_H$-GM

Figure 19:
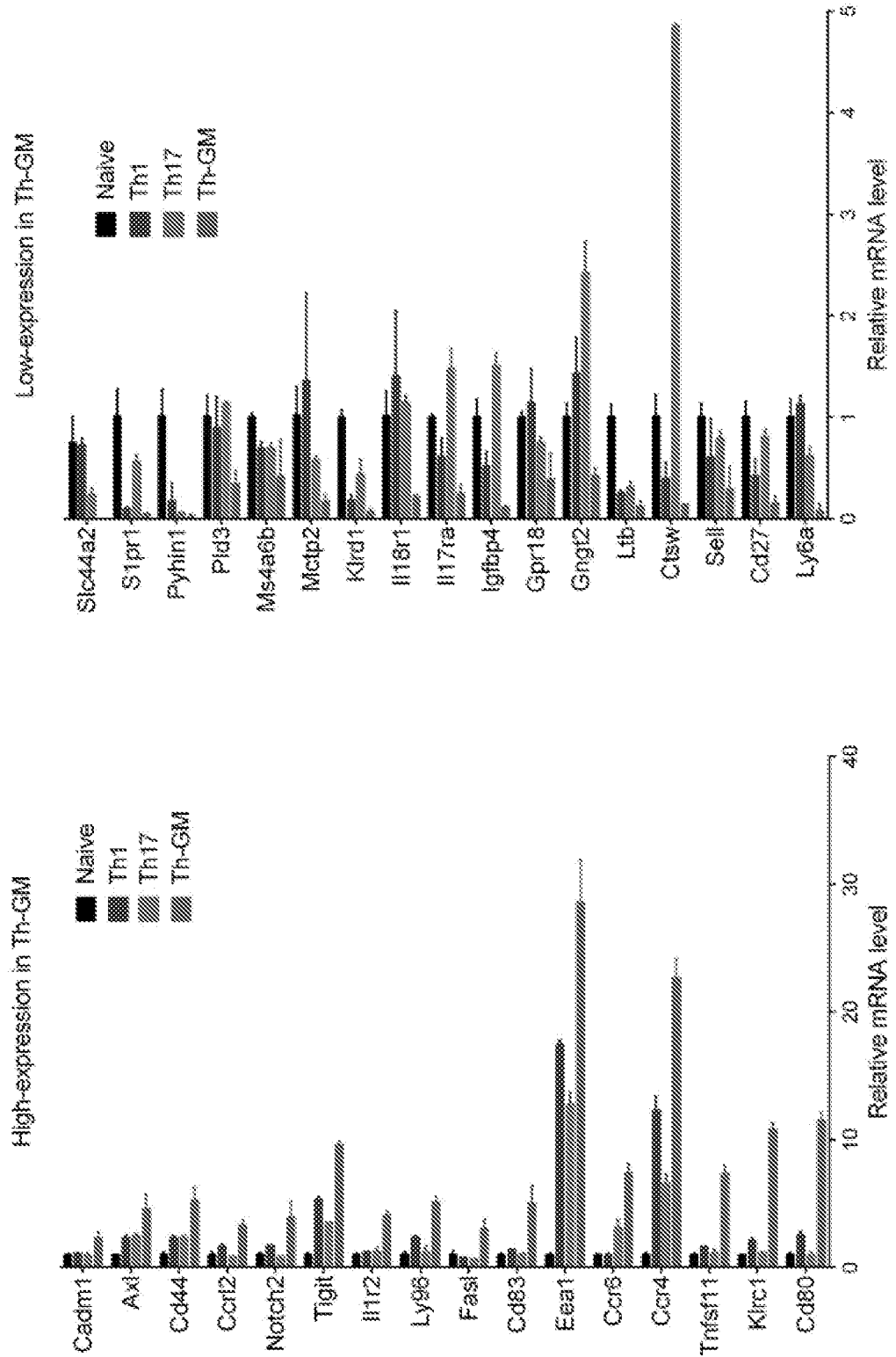
FIG. 19 depicts surface molecules selectively expressed at high level or low level in $T_H$-GM subset as characterized by microarray analysis. These surface molecules specific for each lineage serves as markers, signatures and potential targets for novel diagnosis, treatment and prevention of autoimmune inflammation including, but not limited to multiple sclerosis and rheumatoid arthritis. These cell surface molecules are listed in detail in Table 1. The order of naïve, Th1, Th17, and Th-GM as indicated in the figure insert is the same as that appears for the bars in each graph.
Figures 20A, 20B, 20C, 20D:
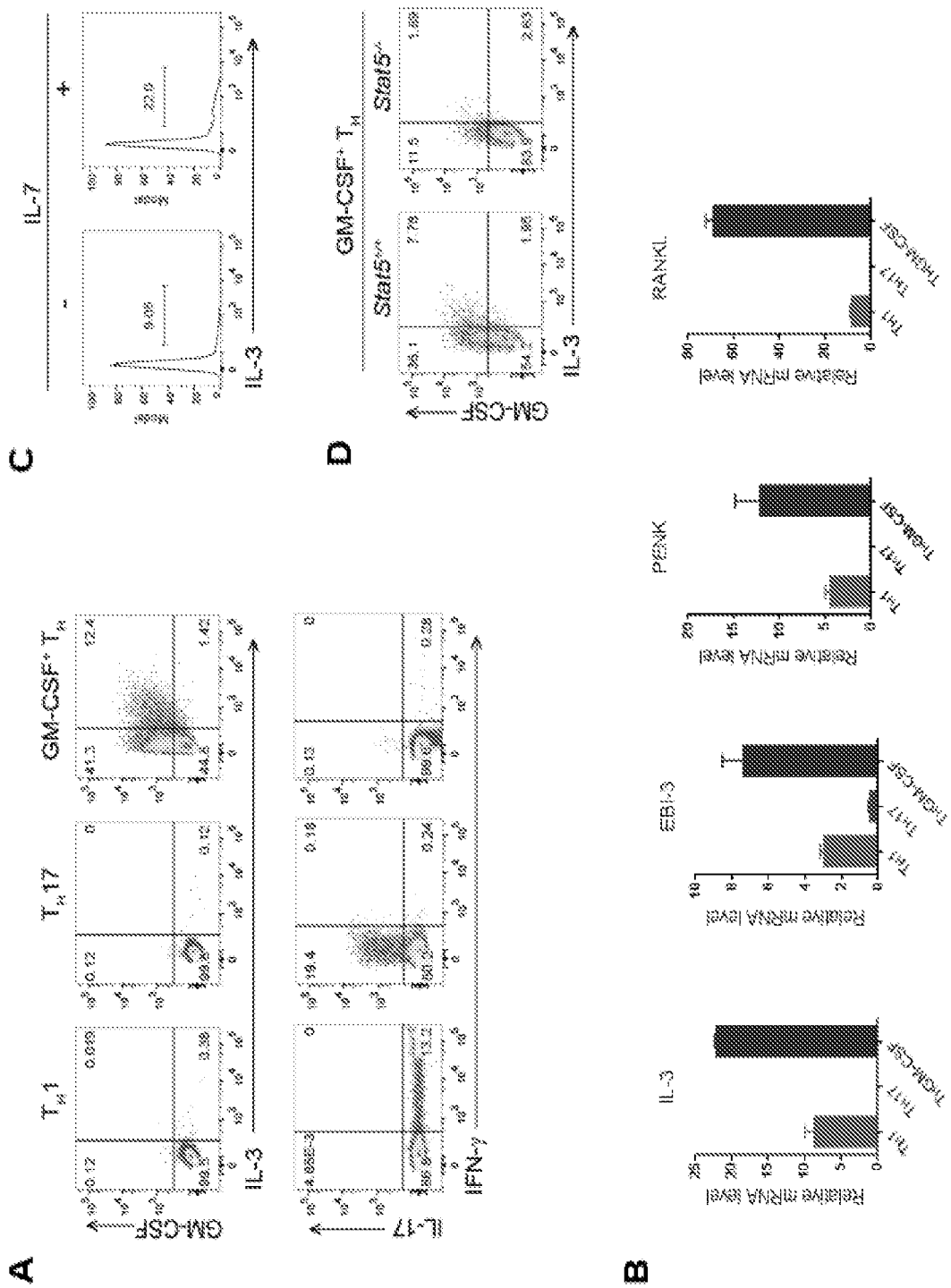
FIGS. 20A-20D show that IL-3 is preferentially expressed in $T_H$-GM cells.

To demonstrate T$_H$-GM as distinct from known T cell subsets (e.g., T$_H$1 and T$_H$17), a whole transcriptome analysis was performed by microarray to validate its specificity compared with known T cell subsets, in particular T$_H$17 cells. Naïve CD4$^+$ T cells were differentiated into T$_H$1, T$_H$17 and T$_H$-GM. Microarray analysis was performed to examine their gene expression profiles. Whole transcriptome clustering indicates T$_H$-GM cells as representing a novel subset distinct from T$_H$1 or T$_H$17 cells. T cell lineage-specific gene expression is shown in Table 1. A list of 202 genes preferentially expressed in T$_H$1 cells were identified, compared with naïve, T$_H$17 or T$_H$-GM cells (fold change >1.7), among which IFN-γ and T-bet are on the top of the list (Table 1). Similarly, T$_H$17-feature genes, such as IL-17, IL-17F, RORγt and RORα, were identified in the list including 411 genes specific to T$_H$17 cells (Table 1). The T$_H$-GM cell-specific gene list ("Genes preferentially upregulated in T$_H$-GM"—the T$_H$-GM signature genes) contains 210 genes including the gene encoding GM-CSF as the top gene in the list (Table 1). A set of surface molecules which were selectively expressed at high level in T$_H$-GM subset, and another set of surface molecules which were selectively expressed at low level in T$_H$-GM subset compared with other subsets were identified (FIG. 19 and Table 1). These molecules (also T$_H$-GM signature genes) can be used for further characterization by surface markers to identify the T$_H$-GM subset of T cells. Several other genes of interest were also identified, including genes encoding cytokines and transcriptional factors, in particular IL-3. Various helper T cells were differentiated in vitro and confirmed that T$_H$-GM cells are potent IL-3 producers as compared with T$_H$1 and T$_H$17 cells (FIGS. 20A, 20C and 20D). In addition, several other cytokines, including EBI-3, PENL and RANKL were found preferentially expressed in T$_H$-GM cells (FIG. 20B), indicating diverse biological functions of T$_H$-GM cells.

Example 8. T$_H$-GM Cells are the Primary Pathogenic Population

Figure 21:
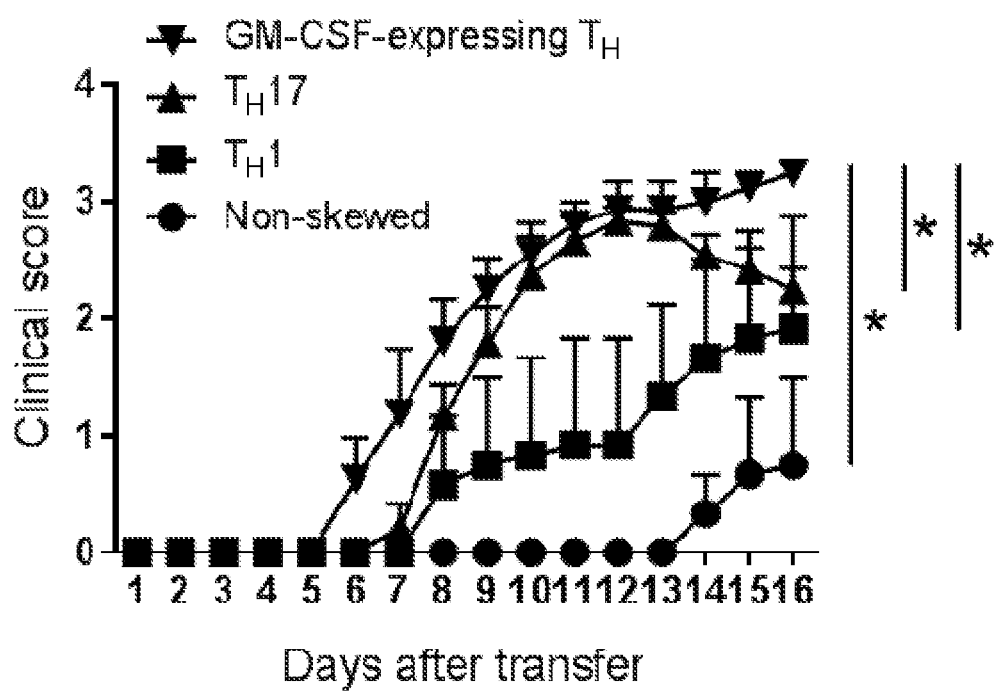
FIG. 21 depicts clinical EAE scores of $Rag2^{-/-}$ mice (n=3~6 mice per group) after adoptive transfer of 6×10⁵ various $MOG_{35-55}$-specific $T_H$ subsets.

To test the hypothesis that GM-CSF-expressing T$_H$ subset (T$_H$-GM) was the primary encephalitogenic effector cells, adoptive transfer of different subsets of MOG$_{35-55}$-specific CD4$^+$ T cells was performed into Rag2$^{-/-}$ mice for EAE induction. As shown in FIG. 21, GM-CSF-expressing T$_H$ cells were preferentially able to induce EAE compared with T$_H$17 and T$_H$1 subsets.

Figures 22A, 22B, 22C, 22D, 22E:
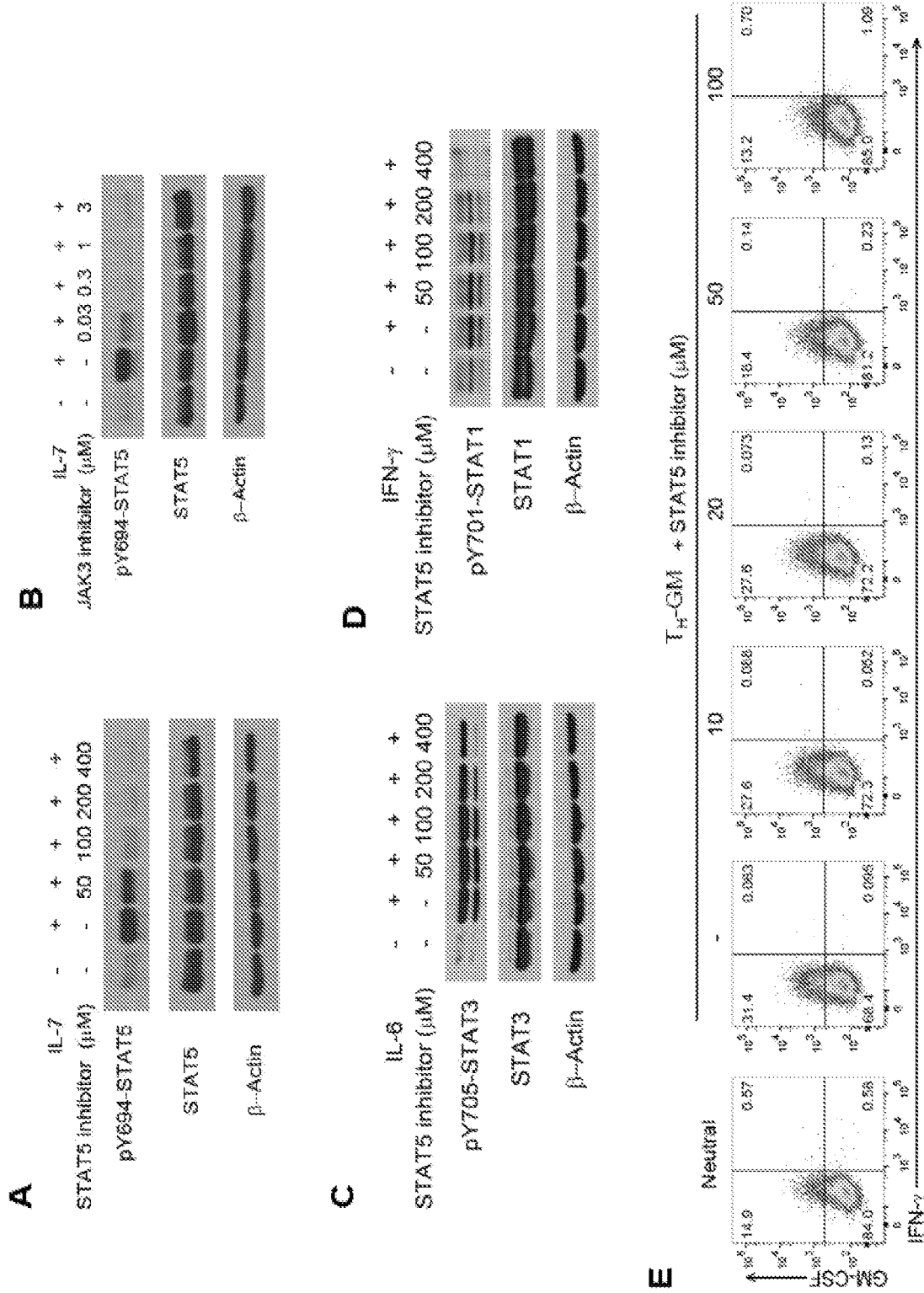

Example 9. The Suppression of STAT5 Activity by Chemical Inhibitor Attenuates GM-CSF Expression by T$_H$-GM and Ameliorates EAE The effect of disrupting STAT5 activation by chemical inhibitor was examined to explore possible methods of treating autoimmune neuroinflammation. The phosphorylation on the key tyrosine residue in SH2 domain is crucial for STAT5 activation and function. A commercial STAT5 inhibitor (CAS 285986-31-4, Calbiochem) has been reported to selectively disrupt tyrosine phosphorylation and DNA binding of STAT5 (Muller et al., 2008). First, the inhibitory effect of this inhibitor on STAT5 activation upon IL-7 stimulation in CD4$^+$ T cells was tested. At a concentration of 50 μM, the inhibitor had about 50% inhibitory effect, which was further enhanced with the increase of concentration (FIG. 22A). STAT5 inhibitor had low affinity and thus required a high concentration to fully block STAT5 activation, whereas JAK3 inhibitor showed potent inhibitory effect even at low concentration (FIG. 22B). The specificity of STAT5 inhibitor was next tested by examining its effect on the activation of STAT3 and STAT1. As shown in FIGS. 22C and 22D, this STAT5 inhibitor at relatively lower concentration (50 or 100 μM) showed minimal inhibitory effect on both STAT3 and STAT1 activation.

The effect of STAT5 inhibition on T$_H$-GM differentiation was examined. As shown, STAT5 inhibitor suppressed T$_H$-GM differentiation in a dosage-dependent manner (FIG. 22E). Reduced T$_H$1 differentiation upon STAT5 inhibitor treatment was observed (data not shown), but T$_H$17 differentiation was not suppressed by STAT5 inhibitor (data not shown).

Figures 23A, 23B, 23C, 23D:
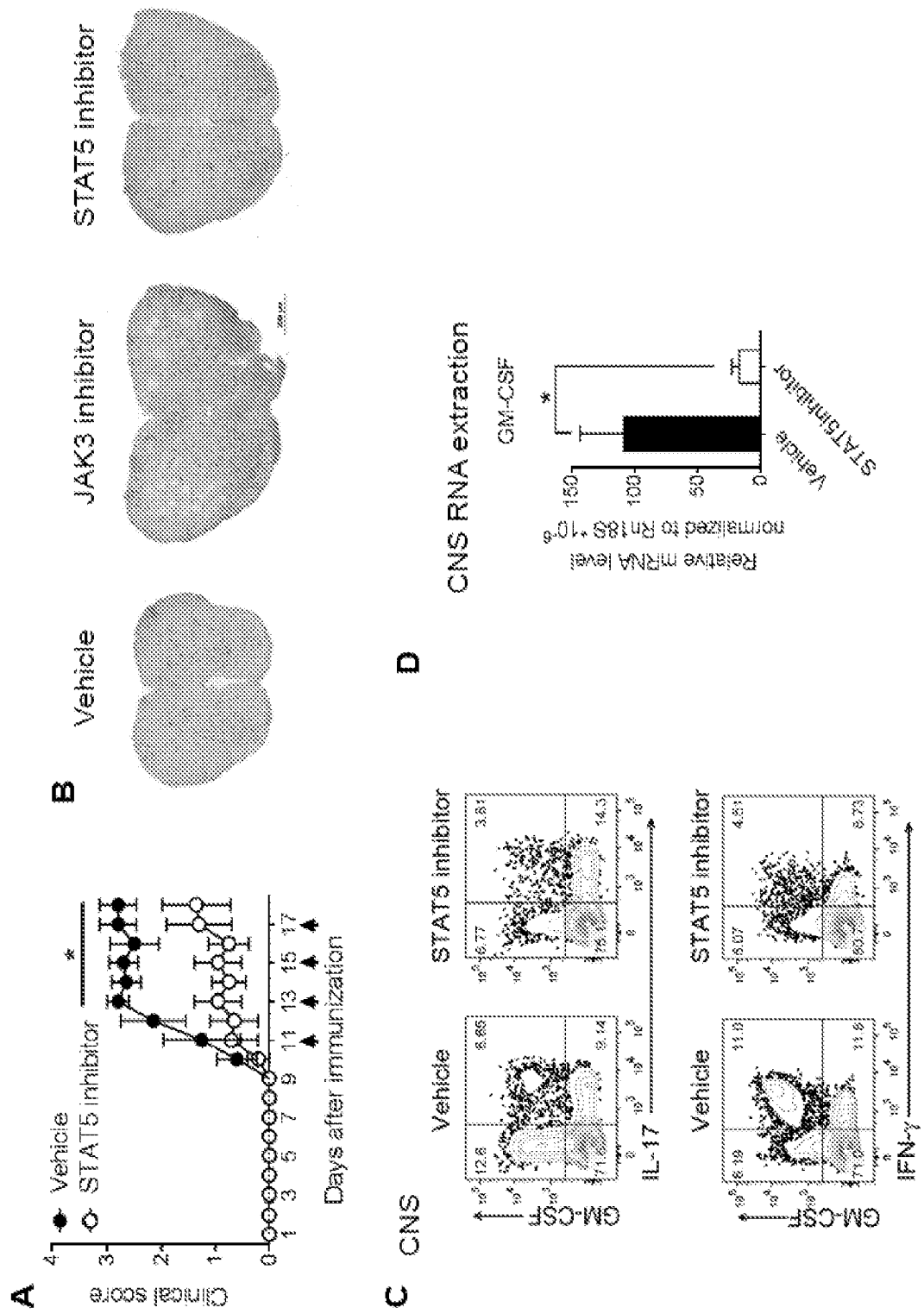
FIGS. 23A-23D depict targeting STAT5 activation by chemical inhibitor ameliorates EAE.

To explore the therapeutic effect of targeting STAT5 activation in EAE disease, the commercial STAT5 inhibitor was administered to wild-type mice intraperitoneally every other day after disease onset. Development of paralysis was assessed by daily assignment of clinical scores. STAT5 inhibition ameliorated EAE severity, associated with reduced immune cell infiltration in the CNS (FIGS. 23A and 23B). In contrast, although JAK3 inhibitor can potently block STAT5 activation (FIG. 22B), it showed detrimental effect on EAE (FIG. 23B). Of note, STAT5 inhibitor resulted in reduced GM-CSF production in CNS-infiltrating CD4$^+$ T cells (FIGS. 23C and 23D). This study indicates that targeting STAT5 by chemical inhibitor is useful in therapeutic intervention in MS.

Example 10. GM-CSF-Producing T$_H$ Cells are Associated with Human RA

Figures 24A, 24B, 24C, 24D, 24E:
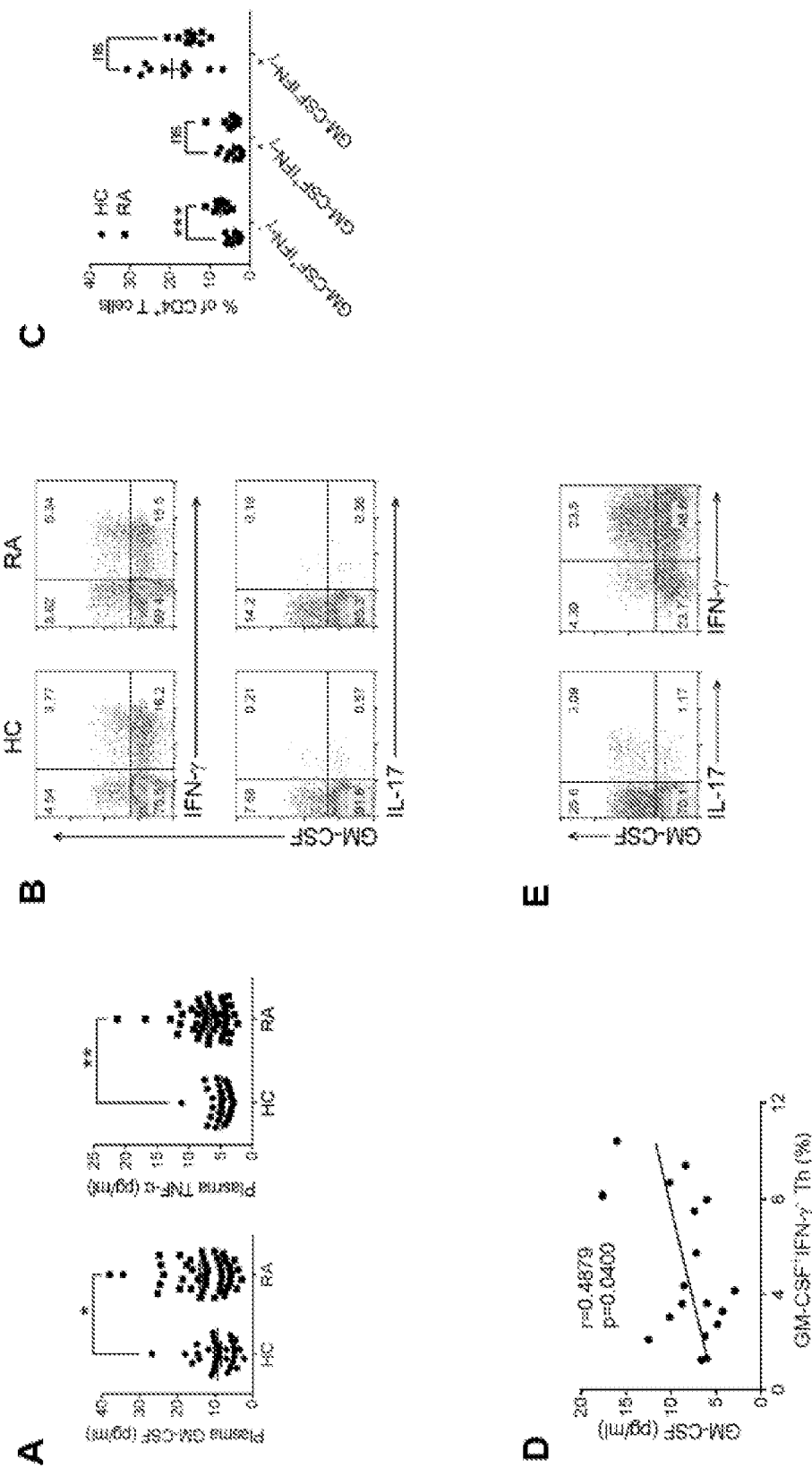
FIGS. 24A-24E depict GM-CSF-producing $T_H$ cells are in association with human RA. Plasma concentrations of GM-CSF and TNF-α in healthy control HC (n=32) and RA (n=47) were quantified by ELISA (FIG. 24A).

Plasma concentrations of GM-CSF and TNF-α in peripheral blood of RA patients were examined in comparison with gender/age-matched healthy control (HC), and found that both cytokines were elevated in RA (FIG. 24A). Ex vivo frequencies of IFN-γ-, IL-17- or GM-CSF-producing T$_H$ cells were quantified in RA and HC. High frequencies of IFN-γ- and/or GM-CSF-producing T$_H$ cells were detected in all samples, but observed low frequency (<1%) of IL-17-producing T$_H$ cells (FIG. 24B). GM-CSF-single-producing (GM-CSF$^+$IFN-γ$^-$) T$_H$ cells represented a substantial population in both RA and HC (FIG. 24B). More importantly, the frequency of this population in peripheral blood of RA was significantly higher than that of HC (FIG. 24C). In contrast, neither GM-CSF/IFN-γ-double-producing nor IFN-γ-single-producing T$_H$ cells showed any significant difference in their frequencies between RA and HC (FIG. 24C). Therefore, the frequency of GM-CSF-single-producing T$_H$ cells in peripheral blood is selectively elevated in RA, suggesting a functional association of T$_H$-cell-secreted GM-CSF with RA. Moreover, a significant correlation between plasma GM-CSF concentration and GM-CSF-single-producing T$_H$ cell frequency was observed in RA (FIG. 24D).

To further evaluate the association of GM-CSF-producing T$_H$ cells with RA, mononuclear cells were isolated from synovial fluid of RA patients and analyzed the abundance of these cells. A marked elevation of GM-CSF-producing T$_H$ cell frequency was observed in synovial fluid compared with peripheral blood, but most of these cells co-expressed IFN-γ (FIG. 24E). Similarly, both T$_H$1 and T$_H$17 frequencies were also increased in synovial fluid, with T$_H$17 remaining to be a minor population compared with T$_H$1 (FIG. 24E).

Figures 25A, 25B, 25C, 25D, 25E:
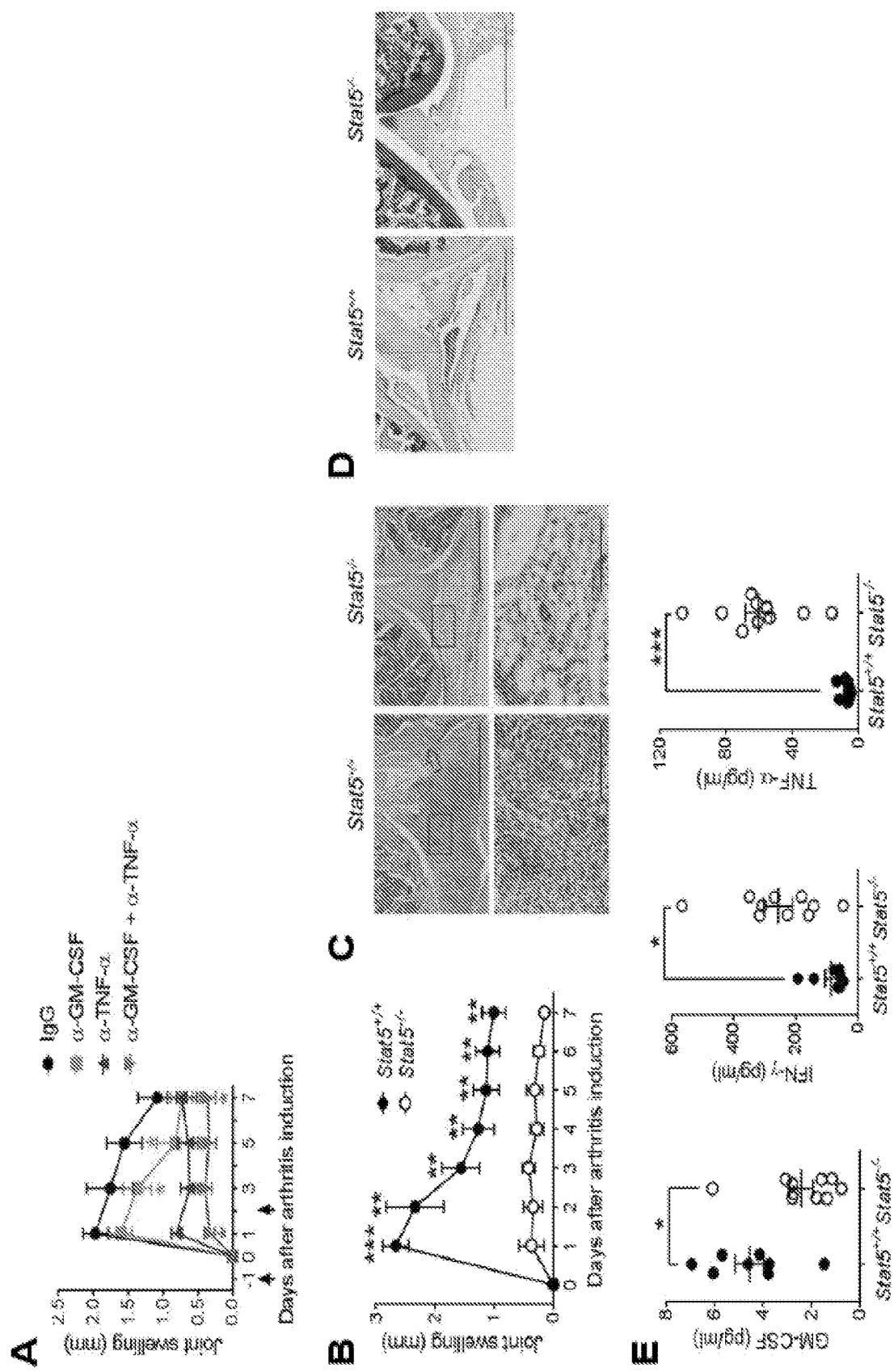
FIGS. 25A-25E depict distinguishable effects of GM-CSF and TNF-α in mouse AIA.
Figures 26A, 26B, 26C, 26D:
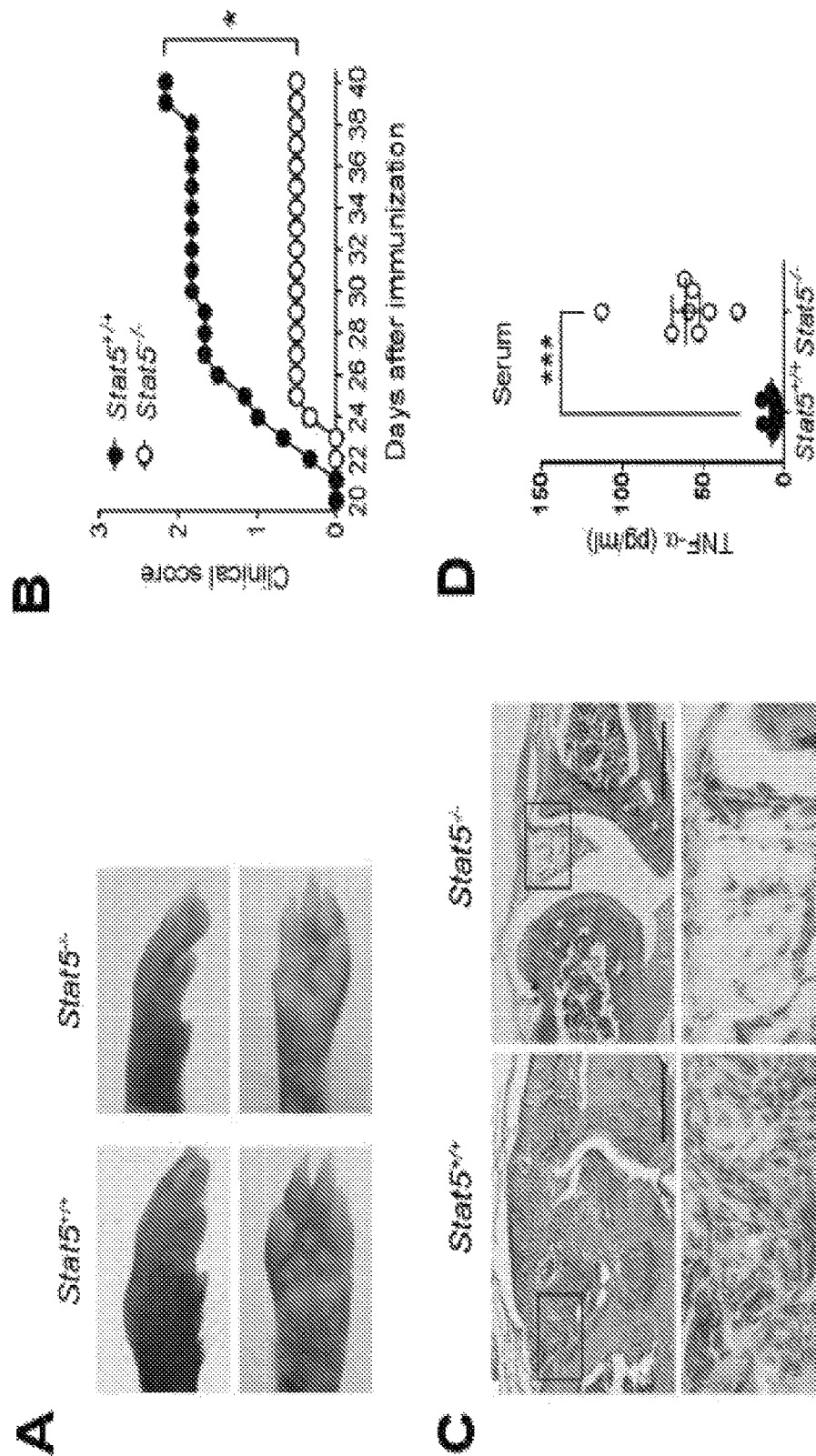
FIGS. 26A-26D depicts mice with Stat5 deletion in T cells are resistant to CIA.

Example 11. GM-CSF Mediates Experimental Arthritis in a TNF-α-Independent Manner The elevation of GM-CSF and TNF-α level in plasma of RA in comparison to HC may suggest a therapeutic approach by targeting these two cytokines. The efficacy of blocking both GM-CSF and TNF-α was tested in treating arthritic mice in antigen-induced arthritis (AIA) model, which is a T-cell driven RA model and is easily inducible in C57BL/6 strain with a rapid and synchronized disease onset, facilitating the exploration of RA pathogenesis. Either GM-CSF or TNF-α individual blockade attenuated AIA development (FIG. 25A). Interestingly, the combination of GM-CSF- and TNF-α-specific neutralizing antibodies showed better efficacy in controlling arthritis development than individual treatments (FIG. 25A). That is, targeting GM-CSF may have beneficial efficacy in treating arthritis in a way independent of TNF-α activity. To further study the distinguishable effects of GM-CSF and TNF-α in mediating arthritis development, a mouse strain (Cd4-Cre; Stat5$^{f/f}$, or Stat5$^{-/-}$ in short) with conditional Stat5 deletion was used in T cells for AIA induction. These conditional Stat5-knockout mice resisted arthritis development, as exemplified by milder joint selling, fewer immune cell infiltration in synovia, and reduced joint destruction (FIGS. 25B-25D), even though they had markedly increased level of serum TNF-α as well as IFN-γ (FIG. 25E). In contrast, serum level of GM-CSF was significantly reduced in knockout mice (FIG. 25E), which was likely the causal factor of the resistance to arthritis development as further supported by results described below. Consistent results were also observed in collagen-induced arthritis (CIA) model (FIGS. 26A-26D). Together, these findings suggest that GM-CSF is an important pathogenic mediator in RA and also indicate the promise of developing anti-GM-CSF drugs to treat RA patients who are anti-TNFα drugs unresponsive, marking GM-CSF-producing $T_H$ cells as a new biomarker for RA diagnosis.

Figures 28A, 28B:
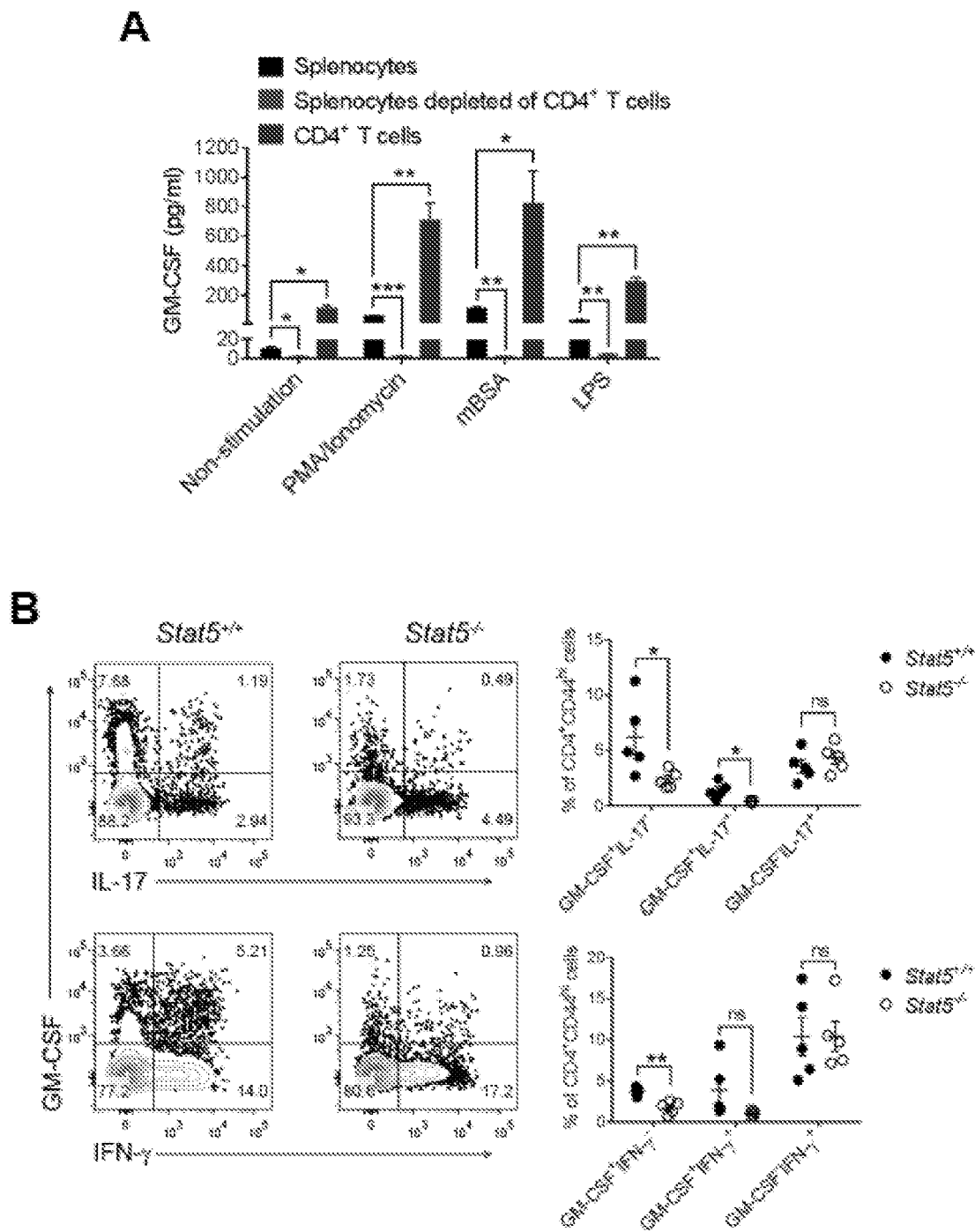
FIGS. 28A-28G depicts STAT5-regulated GM-CSF-producing $T_H$ cells are crucial for AIA. Spleens and synovial tissues were collected from Stat5$^{+/+}$ and Stat5$^{-/-}$ mice at day 7 after arthritis induction.

Example 12. STAT5-Regulated GM-CSF Secretion by Autoreactive $T_H$ Cells Mediates Synovial Inflammation On the basis of association of GM-CSF with RA, the cellular producers of GM-CSF and the regulatory mechanism underlying GM-CSF expression in arthritic mice were examined. Splenocytes were collected from wild-type AIA mice and separated cells into three fractions: splenocytes, splenocytes depleted of CD4$^+$ T cells and CD4$^+$ T cells; and stimulated each fraction at same cell numbers under various conditions. Splenocytes produced low but detectable level of GM-CSF without stimulation, which was markedly increased by PMA/Ionomycin or mBSA antigen stimulation (FIG. 28A). Under all conditions, splenocytes depleted of CD4$^+$ T cells almost completely abrogated GM-CSF production (FIG. 28A). In contrast, CD4$^+$ T cells produced dramatically elevated GM-CSF in comparison to splenocytes under all conditions (FIG. 28A). These results strongly support that CD4$^+$ T cells are predominant producers of GM-CSF at least in spleens of arthritic mice, which is somehow consistent the observed correlation of plasma GM-CSF concentration with GM-CSF-single-producing $T_H$ cell frequency in RA (FIG. 24D). Thus, the functional significance of $T_H$-cell-secreted GM-CSF was examined in arthritis development. Given T-cell-specific Csf2-knockout mice is not available and STAT5 is a key regulator of GM-CSF expression in $T_H$ cells, conditional Stat5-knockout mice was used, which showed decreased GM-CSF level and resistance to arthritis development as described above.

Figures 27A, 27B, 27C, 27D, 27E:
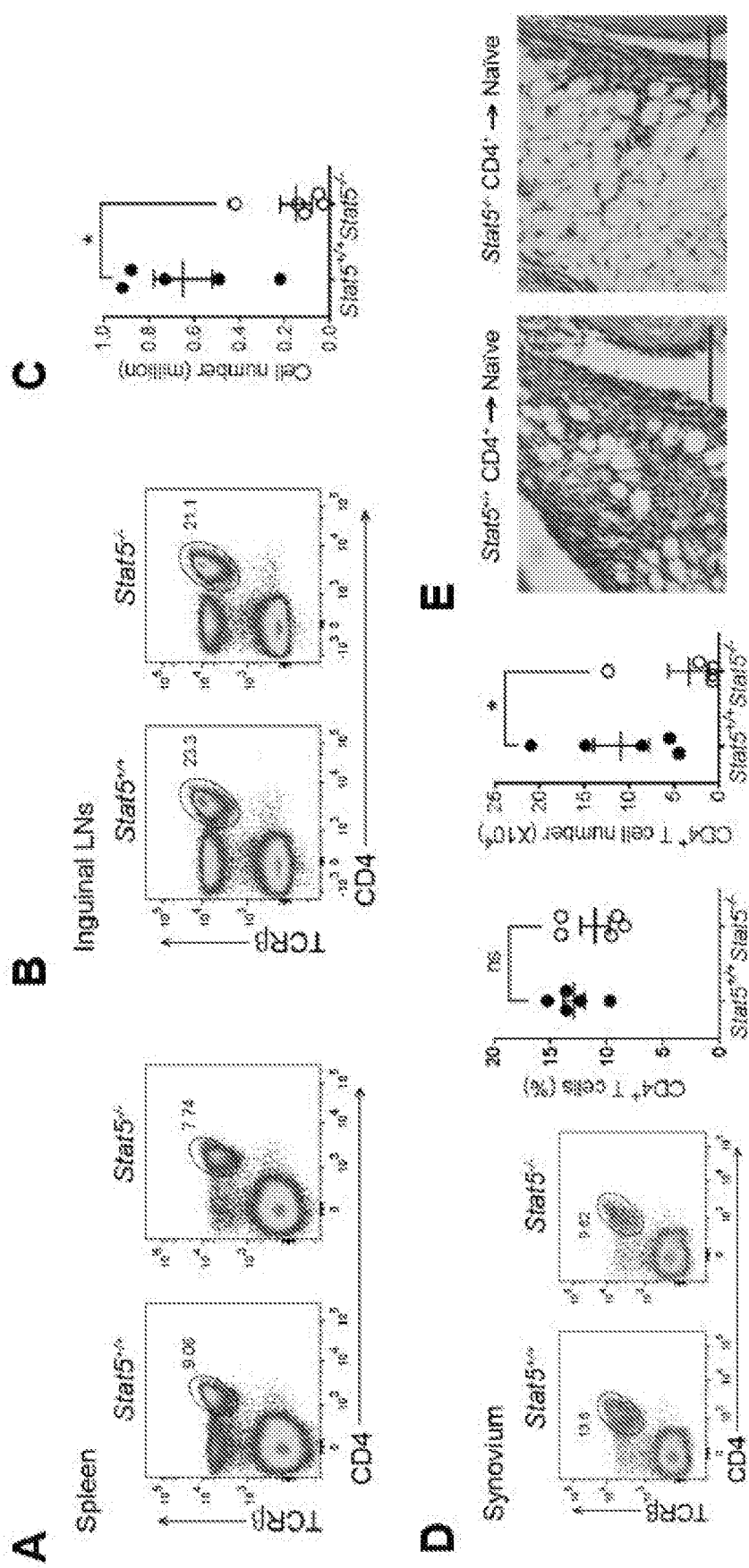

Consistent with a previous study (Burchill et al., 2007), similar frequencies of CD4$^+$ T cells were observed in peripheral lymphoid tissues as well as in inflamed synovial tissues of STAT5-deficient mice compared with wild-type mice at day 7 after AIA induction (FIGS. 27A-27D), suggesting loss of STAT5 seems to not impair CD4$^+$ T-cell generation in periphery and infiltration in synovial tissues. To determine the requirement of STAT5 for arthritogenic potential of CD4$^+$ T cells, ex vivo-expanded antigen-reactive CD4$^+$ T cells, derived from Stat5$^{+/+}$ and Stat5$^{-/-}$ AIA mice, were transferred into wild-type naïve mice separately, followed by intra-articular injection of mBSA. Mice receiving Stat5$^{+/+}$ CD4$^+$ T cells displayed an abundant immune cell infiltration in synovial tissues at day 7 after AIA induction (FIG. 27E). In contrast, mice receiving Stat5$^{-/-}$ CD4$^+$ T cells had marked reduction of synovial infiltrates (FIG. 27E). Therefore, STAT5-deficient CD4$^+$ T cells are defective in arthritogenic potential.

Multiple lines of evidence support a central role of T cells in RA. However, the pathogenic mechanism of T cells remains insufficiently understood. Although $T_H1$ is a predominant population among synovial infiltrating CD4$^+$ T cells in human RA (Berner et al., 2000; Yamada et al., 2008), defective IFN-γ signaling results in increased disease susceptibility in animal models of arthritis (Guedez et al., 2001; Irmler et al., 2007; Manoury-Schwartz et al., 1997; Vermeire et al., 1997). In contrast, $T_H17$ cells are proven crucial in animal models of arthritis (Pernis, 2009), but predominance of $T_H17$ cells is limited in both peripheral blood and synovial compartment of human RA (Yamada et al., 2008) and (FIGS. 1B and 1E). As demonstrated herein, STAT5-regulated GM-CSF-producing $T_H$ cells potentiate arthritis pathogenesis.

Figures 28C, 28D, 28E:
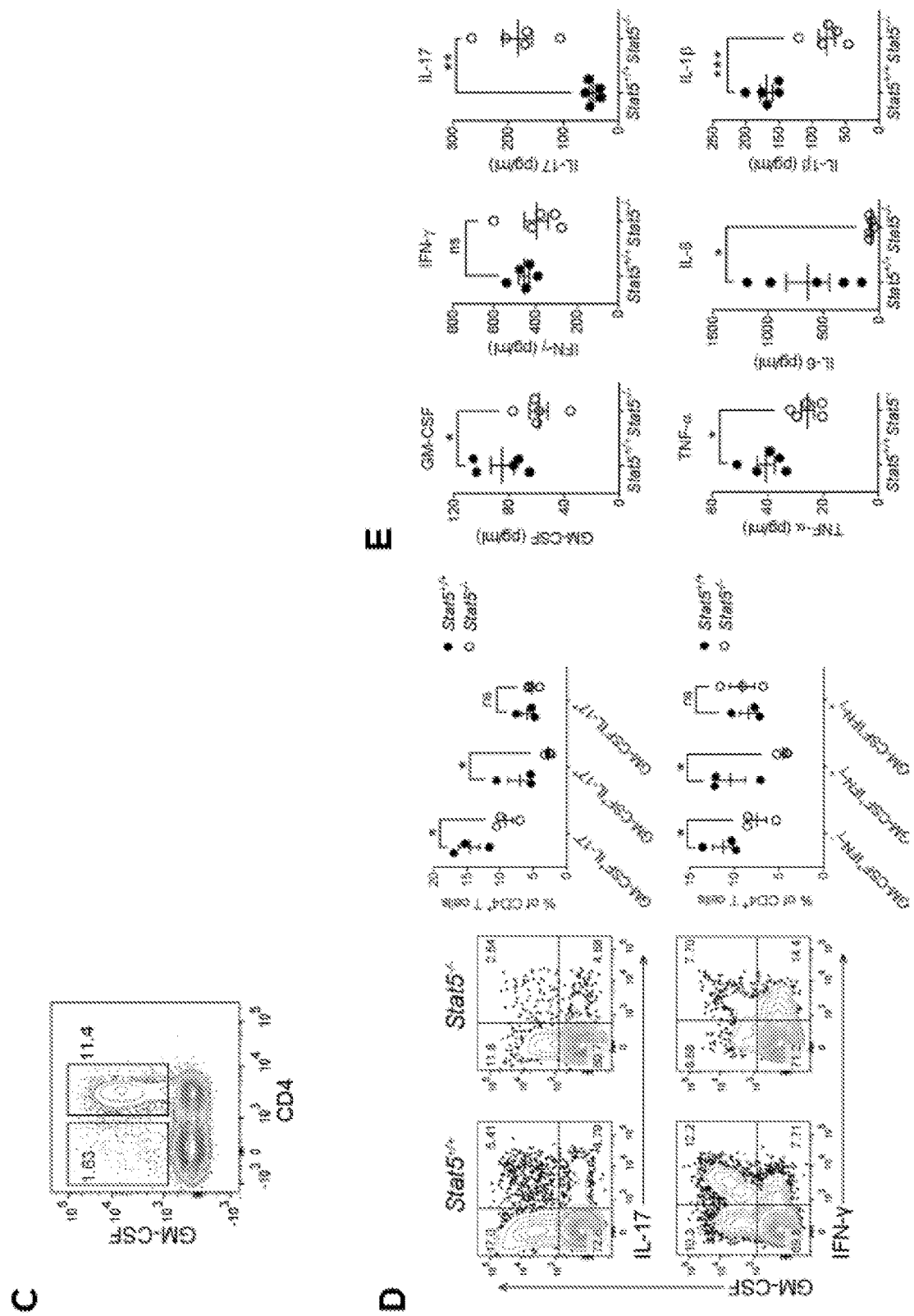
Figures 28F, 28G:
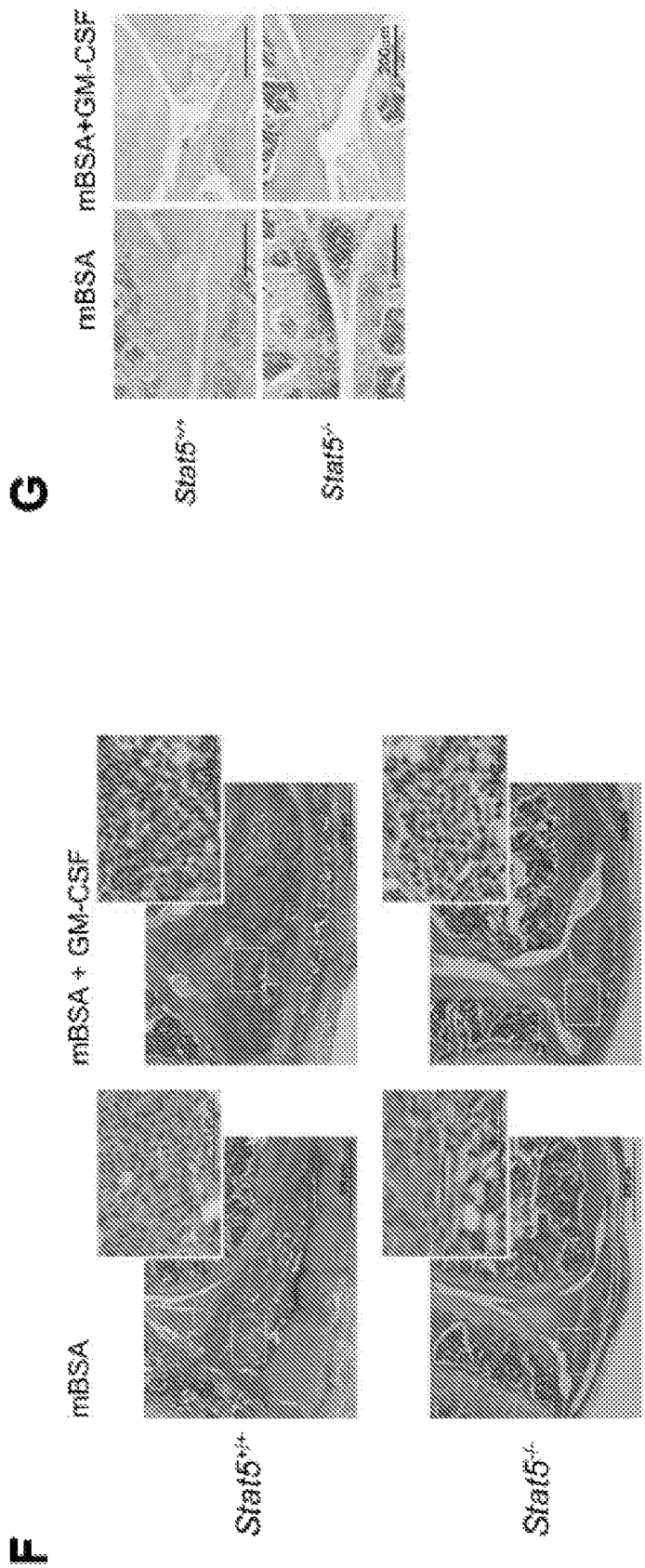
Figures 29A, 29B, 29C:
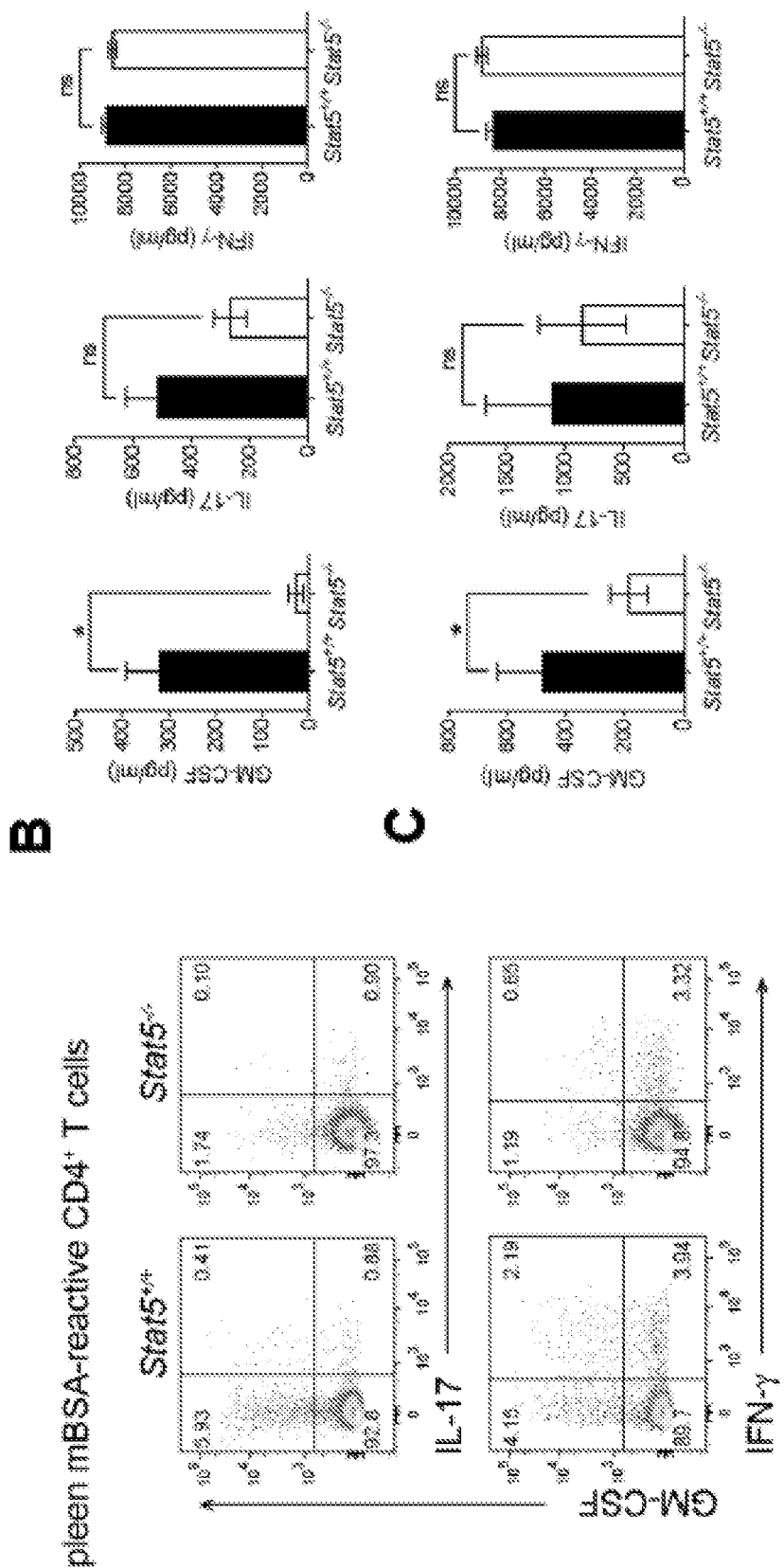
FIGS. 29A-29C depicts loss of STAT5 results in impaired GM-CSF production by antigen-specific CD4$^+$ T cells. Spleens and inguinal LNs were collected from Stat5$^{+/+}$ and Stat5$^{-/-}$ mice at day 7 after arthritis induction, and dissociated into single cell suspensions. Then, cells were stimulated with mBSA (20 μg/ml) for 24 h.
Figures 30A, 30B, 30C:
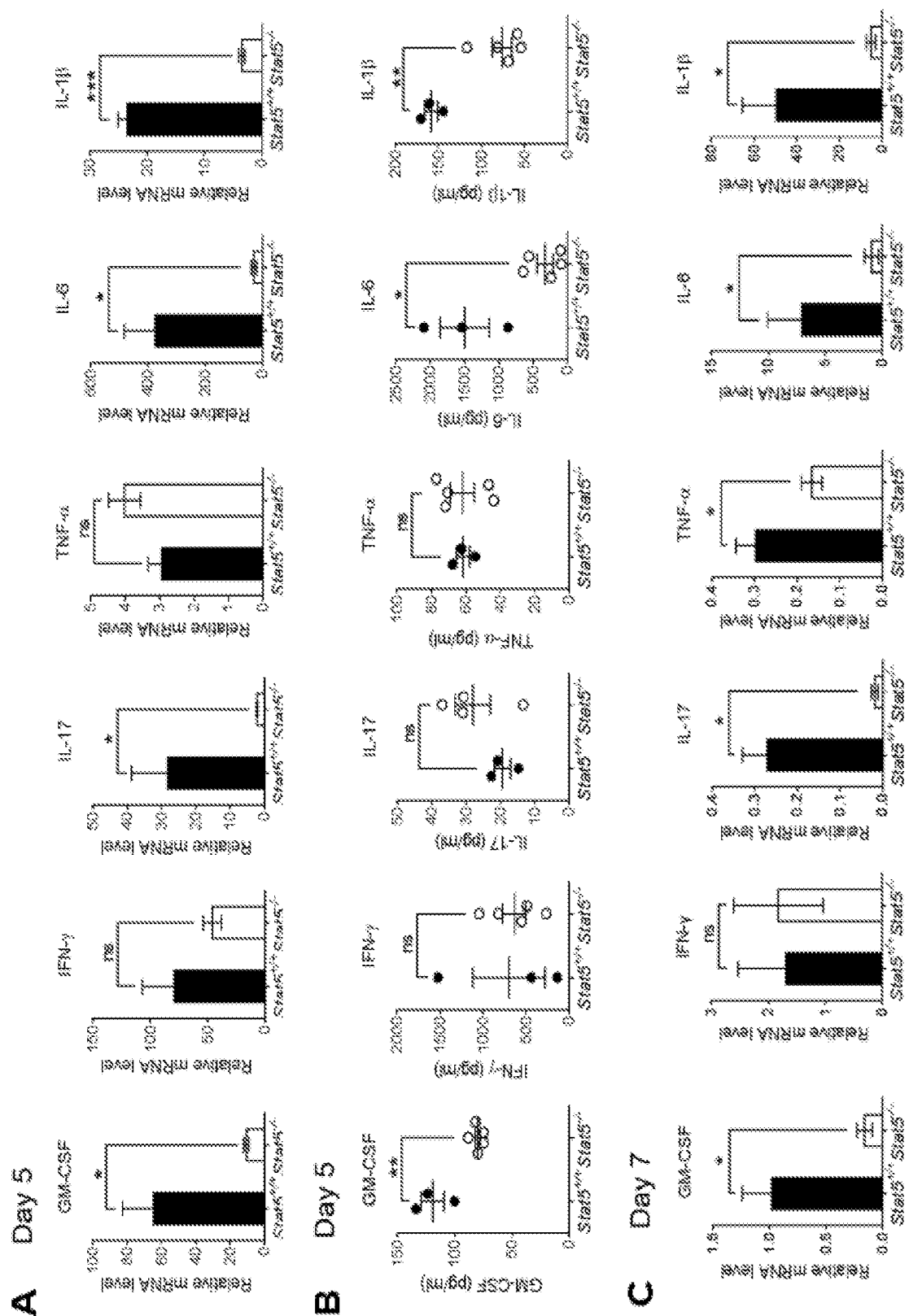
FIGS. 30A-30C depicts loss of STAT5 impairs IL-6 and IL-1β expression in synovial tissues of arthritic mice.
Figures 34A, 34B, 34C, 34D, 34E, 34F, 34G, 34H, 34I:
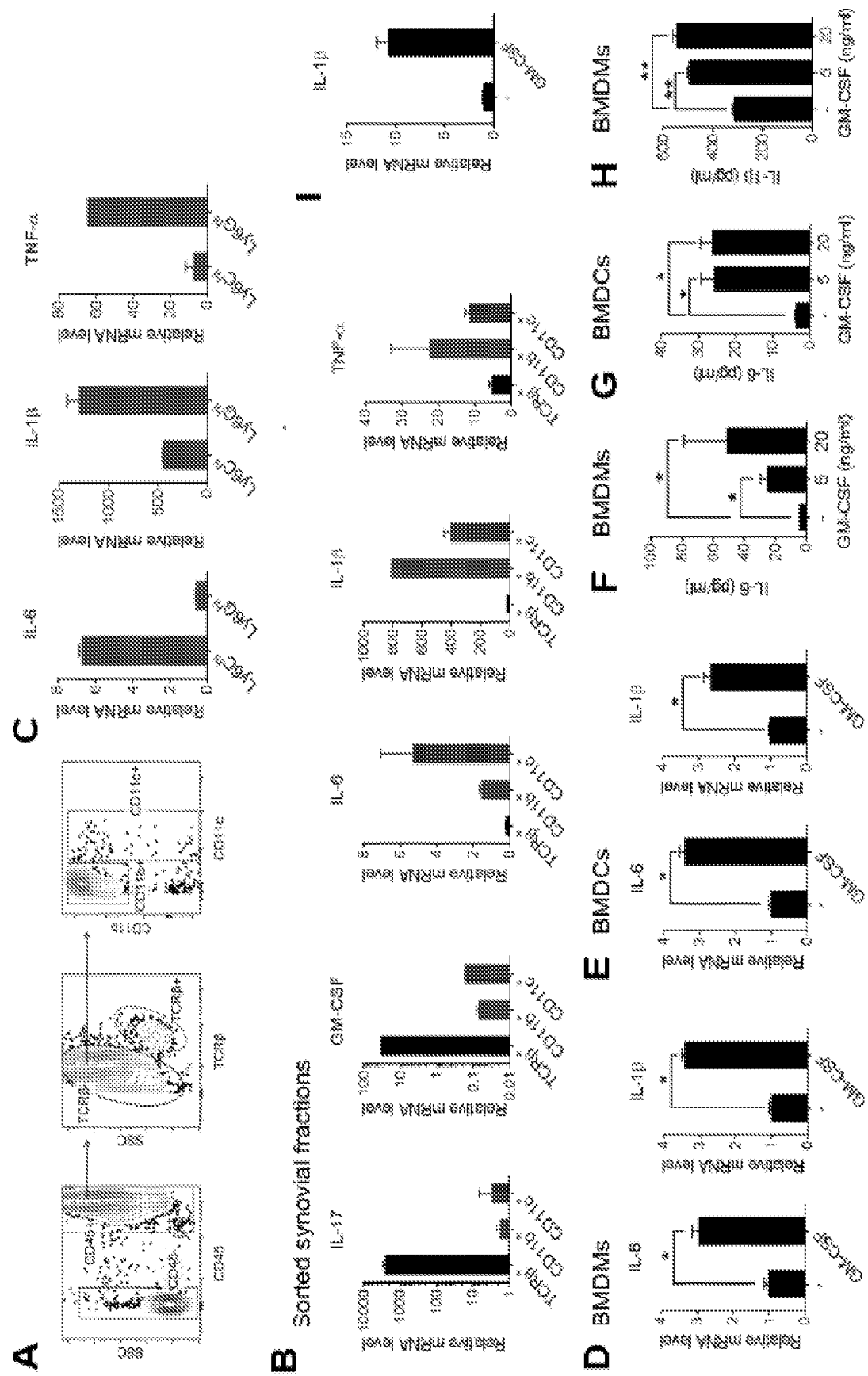
FIGS. 34A-34I depicts GM-CSF mediates proinflammatory cytokine expression by myeloid cells and synovial fibroblasts in arthritic mice. Synovial tissues were dissected from wild-type AIA mice and dissociated into single cell suspensions.

To validate the regulatory role of STAT5 in GM-CSF production, splenocytes derived from AIA mice were stimulated with PMA/Ionomycin plus Golgiplug ex vivo, followed by intracellular cytokine staining and flow cytometry. As expected, the frequency of GM-CSF-single-producing cells among CD4$^+$CD44$^{hi}$ population was significantly decreased in Stat5$^{-/-}$ mice (FIG. 28 34B). Notably, no significant differences were observed in frequencies of IL-17-single-producing ($T_H17$) or IFN-γ-single-producing ($T_H1$) cells between two groups (FIG. 28B). Further study by combining mBSA restimulation and intracellular cytokine staining showed that the frequency of mBSA-specific GM-CSF-producing effector T cells was much lower in spleens of Stat5$^{-/-}$ mice than those in controls (FIG. 29A). In addition, AIA mice-derived splenocytes and inguinal lymph nodes (LNs) were restimulated with mBSA ex vivo to measure cytokine concentrations in culture supernatants and found a significant reduction of GM-CSF with deletion of STAT5, but comparable levels of both IL-17 and IFN-γ between two groups (FIGS. 29B and 29C). Together, the results indicate that loss of STAT5 may specifically suppress GM-CSF-producing effector Th cells but not $T_H17$ or $T_H1$ cells in experimental arthritis.

To investigate the involvement of GM-CSF-producing $T_H$ cells and their regulation by STAT5 in synovial inflammation, synovial tissues were dissected from AIA mice and examined cytokine production by $T_H$ cells. In spite of multiple cellular sources of GM-CSF (Cornish et al., 2009), CD4$^+$ $T_H$ cells were prominent producers of GM-CSF in synovial tissues of AIA mice (FIG. 28C), consistent with the observation in spleens (FIG. 28A). Moreover, a significantly lower percentage of synovial GM-CSF-producing $T_H$ cells was detected in Stat5$^{-/-}$ mice than Stat5$^{+/+}$ mice (FIG. 28D). On the other hand, both $T_H1$ and $T_H17$ cells exhibited similar percentages between two groups (FIG. 28C). A decrease in GM-CSF level in synovial compartments of Stat5$^{-/-}$ mice in comparison to controls was expected. To address this, inflamed synovial tissues were harvested from AIA mice for RNA and protein extraction to examine cytokine level by qPCR and ELISA. Indeed, lower synovial GM-CSF but not IFN-γ or IL-17 was detected in Stat5$^{-/-}$ mice than Stat5$^{+/+}$ mice at day 5 or 7 after arthritis induction (FIGS. 28E and 30A-30C). In addition, two important proinflammatory cytokines IL-6 and IL-1β were also found persistently and significantly reduced in STAT5-deficient mice (FIGS. 28E and 30A-30C), indicating the attenuated synovial inflammation. Notably, TNF-α production was reduced at day 7 but not at day 5 in STAT5-deficient mice (FIGS. 28E and 30A-C). Together, these results indicate that STAT5-regulated GM-CSF expression by arthritogenic $T_H$ cells is crucial for evoking synovial inflammation.

To determine the critical role of STAT5-regulated GM-CSF production by $T_H$ cells in mediating synovitis and arthritis development, GM-CSF was administered via intra-articular injection in mixture with mBSA to the left knee joints of mBSA/CFA-immunized mice, whereas mBSA was injected alone to the right knee joints. Injection with mBSA alone was sufficient to induce abundant immune cell infiltration in the synovial compartments of Stat5$^{+/+}$ mice but failed to do so in Stat5$^{-/-}$ mice (FIG. 28F). Administration of GM-CSF together with mBSA efficiently restored synovial inflammation in Stat5$^{-/-}$ mice (FIG. 34F). Consistently, the Safranin-O/Fast Green staining revealed severe cartilage depletion upon GM-CSF/mBSA injection, but not mBSA alone, in Stat5$^{-/-}$ mice (FIG. 28G). These results therefore provide support for the notion that STAT5-regulated GM-CSF production by arthritogenic $T_H$ cells is essential for mediating arthritis pathogenesis.

Figures 31A, 31B, 31C, 31D:
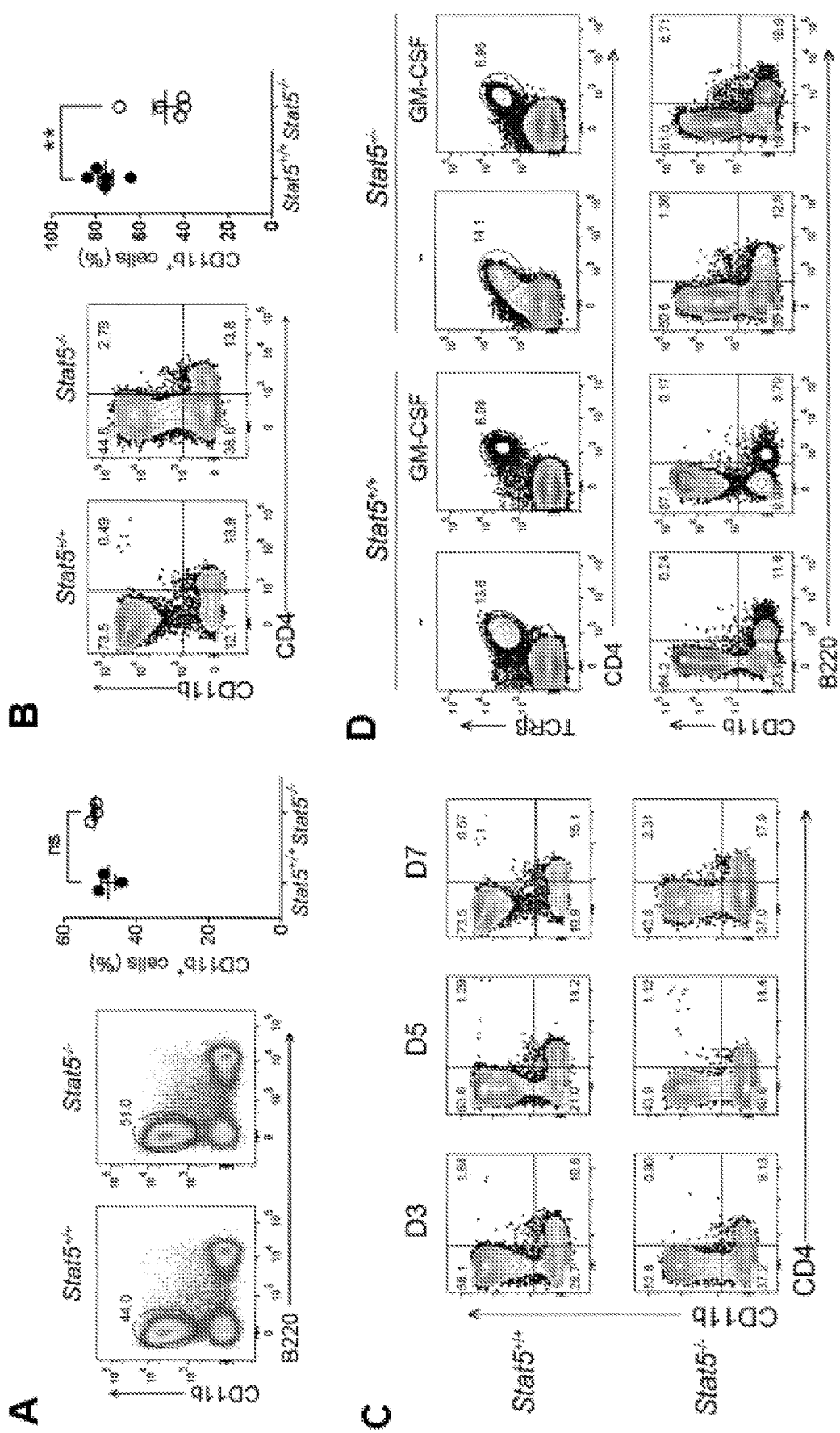
FIGS. 31A-31D depicts SAT5-induced GM-CSF expression mediates CD11b$^+$ cell accumulation in inflamed synovial tissues.

Example 13. Th-Cell-Derived GM-CSF Mediates Neutrophil Accumulation in Synovial Tissues The mechanism by which GM-CSF-producing Th cells evoke synovial inflammation and drive arthritis development was examined. Myeloid lineage-derived cells, including neutrophils, DCs and macrophages, express GM-CSF receptor and are common targets of GM-CSF (Hamilton, 2008). Importantly, those cells invade synovial compartments in RA patients and mouse arthritis models, and contribute to synovitis (McInnes and Schett, 2011). The infiltration of myeloid lineage-derived cells in synovial compartments of AIA mice was examined. CD11b$^+$ myeloid cells represented a predominant population (~70%) among synovial infiltrating leukocytes (FIG. 31B). Although CD4$^+$ $T_H$ cell infiltration was not altered by STAT5 deletion, synovial CD11b$^+$ cell infiltration was significantly reduced in Stat5$^{-/-}$ mice compared with Stat5$^{+/+}$ mice when examined at day 7 after arthritis induction (FIG. 31B). This reduction is unlikely due to defective hematopoiesis, as similar frequencies of CD11b$^+$ cells were detected in spleens of two group (FIG. 31A). Further, CD11b$^+$ cells continuously increased in synovial tissues of wild-type mice, but not STAT5-deficient mice, over a 7-day time course (FIG. 31C). Notably, the selective ablation of synovial CD11b$^+$ cell accumulation in STAT5-deficient mice can be partially restored by local administration of GM-CSF during arthritis induction (FIG. 31D). Together, these results indicate that myeloid cell accumulation in synovial compartments may be specifically dampened by T-cell-specific STAT5 deletion and resultant GM-CSF insufficiency.

Next, different populations of CD11b$^+$ cells, including DCs, macrophages and neutrophils were analyzed. Monocyte-derived dendritic cells (MoDCs), characterized as CD11c$^{int}$CD11b$^{hi}$Ly6C$^{+/hi}$MHCII$^{hi}$, were recently reported to be involved in the mBSA/IL-1β arthritis model (Campbell et al., 2011). In the AIA model of the present study, MoDCs were identified at low abundance in spleens and synovial tissues (data not shown). Furthermore, comparable frequencies of MoDCs were detected in both peripheral lymphoid tissues and synovial tissues between Stat5$^{+/+}$ and Stat5$^{-/-}$ mice (data not shown). These results are in agreement with a previous study showing a dispensable role of GM-CSF in MoDC differentiation (Greter et al., 2012).

Figures 32A, 32B, 32C, 32D:
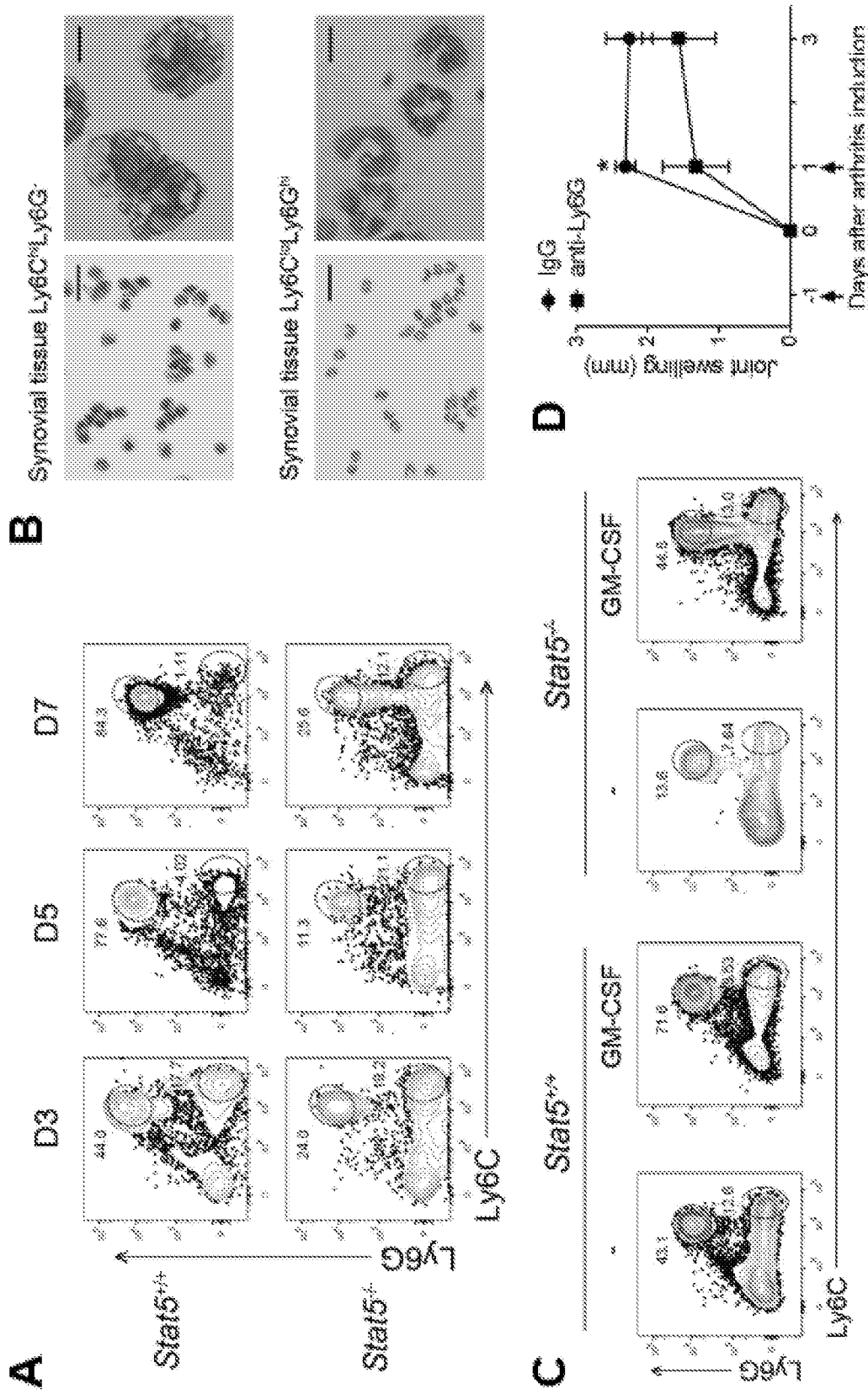
FIGS. 32A-32D depicts GM-CSF mediates neutrophil accumulation in arthritic mice.

Neutrophils have great cytotoxic potential and contribute to the RA initiation and progression in multiple ways (Wright et al., 2014). It has been suggested that RA disease activity and joint destruction directly correlates with neutrophil influx to joints (Wright et al., 2014). Based on the differential expression of Ly6C and Ly6G, CD11b$^+$ myeloid cells can be classified into Ly6C$^{lo}$Ly6G$^{hi}$ population (neutrophils) and Ly6C$^{hi}$Ly6G$^-$ population (monocytes/macrophages). The present study shows that Ly6C$^{lo}$Ly6G$^{hi}$ population continued to accumulate in synovial tissues over a 7-day time course, and represented a predominant population among synovial CD11b$^+$ cells in wild-type mice at day 7 after AIA induction, whereas this population was persistently and dramatically diminished in STAT5-deficient mice (FIG. 32A). Using Giemsa stain, it was validated that synovial-infiltrating Ly6C$^{lo}$Ly6G$^{hi}$ population were neutrophils, which displayed typical polymorphonuclear characteristics with ring-shaped nuclei (FIG. 32B). In contrast, synovial-infiltrating Ly6C$^{hi}$Ly6G$^-$ population had mononuclear morphology and were likely monocytes/macrophages (FIG. 32B). Importantly, intraarticular administration of GM-CSF during arthritis induction efficiently restored neutrophil accumulation in synovial compartments of STAT5-deficient mice (FIG. 32C), suggesting a critical role of $T_H$-cell-derived GM-CSF in mediating neutrophil accumulation to inflamed joints.

Neutrophils are recruited during inflammation, in which complex interactions between neutrophils and vascular endothelial cells direct neutrophil adhesion and transmigration from circulation to inflamed tissues (Kolaczkowska and Kubes, 2013). In an in vitro transmigration assay, neutrophil adhesion and migration across monolayers of endothelial cells was significantly enhanced by GM-CSF as chemoattractant (FIGS. 33A and 33B), suggesting GM-CSF may mediate neutrophil recruitment to inflamed joints in AIA. Effective neutrophil apoptosis is crucial for the resolution of inflammation. However, in synovitis, neutrophil apoptosis is delayed with a result of extended survival and persistent inflammation (Wright et al., 2014). Thus, the effect of GM-CSF on neutrophil survival was tested and found that GM-CSF had profound efficacy in delaying neutrophil apoptosis (FIG. 33C). Together, these results indicate that GM-CSF may mediate neutrophil recruitment and sustain neutrophil survival in synovial compartments and contribute to persistent synovitis. To determine the critical role of neutrophils in AIA, \ neutralizing antibody (1A8) specific for Ly6G was used to deplete neutrophils in vivo. The administration of neutralizing antibody resulted in significant improvement of joint swelling in AIA (FIG. 32D). Thus, neutrophils accumulation mediated by $T_H$-cell-derived GM-CSF are important for AIA development.

Example 14. GM-CSF Enhances Proinflammatory Cytokine Production by Myeloid Cells and Synovial Fibroblasts Cytokines are important mediators in the cross-talk between innate and adaptive immunity. As shown herein, several proinflammatory cytokines (IL-6, IL-1β and TNF- α), which are in association with RA pathogenesis (Choy and Panayi, 2001), were significantly reduced in synovial tissues of STAT5-deficient AIA mice (FIGS. 28E and 30A-30C). To gain insights into the mechanism underlying the observed cytokine reduction, the cellular sources of these proinflammatory cytokines were examined by fractionating synovial cells into different populations based the differential expression of surface markers (FIG. 34A). Cytokine mRNA expression level in CD45$^+$ TCRβ$^+$ population (T cells), CD45$^+$ TCRβ$^-$CD11c$^-$ CD11b$^+$ population (mostly monocytes/macrophages and neutrophils) and CD45$^+$ TCRβ$^-$ CD11c$^+$ population (dendritic cells) was assessed by RT-PCR. GM-CSF, as similar to IL-17 (as a control), was predominantly produced by synovial T cells (FIG. 34B), further reinforcing the importance of GM-CSF-producing $T_H$ cells. In contrast, IL-6 and IL-1β were mainly produced by myeloid cells, e.g. CD11b$^+$ population and CD11c$^+$ population (FIG. 34B). TNF-α was expressed by all three populations, with relatively lower abundance in T cells (FIG. 34B). Based on the differential expression of Ly6C and Ly6G in CD11b$^+$ population as discussed above, Ly6C$^{lo}$Ly6G$^{hi}$ population (neutrophils) and Ly6C$^{hi}$Ly6G$^-$ population (monocytes/macrophages) were further analyzed, which showed that monocytes/macrophages were likely the major IL-6 producers whereas neutrophils seemed to be better producers of IL-1β and TNF-α (FIG. 34C). These results, together with the findings above (FIGS. 28E and 30A-30C), indicate a link that $T_H$-cell-secreted GM-CSF elicits proinflammatory cytokine expression from myeloid cells in synovitis.

To test the regulatory role of GM-CSF in the expression of IL-6 and IL-1β, bone marrow-derived macrophages (BMDMs) and bone marrow-derived dendritic cells (BMDCs) were cultured, and stimulated with GM-CSF. Indeed, GM-CSF stimulation quickly upregulated mRNA expression of both IL-6 and IL-1β within 1 hour (FIGS. 34D and 34E). In addition, GM-CSF markedly increased the secretion of IL-6 from BMDMs in a dosage-dependent manner (FIG. 34F), and from BMDCs even at low dosage (FIG. 34G). To induce mature IL-1β secretion, BMDMs were primed with LPS for 6 h during which different concentrations of GM-CSF was added, followed by ATP stimulation. The addition of GM-CSF significantly enhanced the secretion of IL-1β into culture supernatant as measured by ELISA (FIG. 34H). Synovial fibroblasts, the active players in synovial inflammation (Muller-Ladner et al., 2007), also showed increased IL-1β mRNA expression upon GM-CSF stimulation (FIG. 34I). An inducible effect of GM-CSF on TNF-α expression was not observed in BMDMs, BMDCs or synovial fibroblasts (data not shown). Given the functional importance of IL-6 and IL-1β in arthritis development (Choy and Panayi, 2001), $T_H$-cell-secreted GM-CSF may mediate synovial inflammation also via eliciting the expression of IL-6 and IL-1β from myeloid cells and synovial fibroblasts.

TABLE 1

Summary of genes differentially expressed in $T_H1$, $T_H17$, and $T_H$-GM cells

| Genes differentially expressed in $T_H1$ | | Genes differentially expressed in $T_H17$ | | Genes differentially upregulated in $T_H$-GM cells | | Genes upregulated on $T_H$-GM surface | | Genes downregulated on $T_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| 10366586 | interferon gamma | 10353415 | interleukin 17F | 10385918 | interleukin 3 | 10435704 | CD80 antigen | Ly6a | lymphocyte antigen 6 complex, locus A |
| 10598013 | chemokine (C-C motif) receptor 5 /// chemokine (C-C motif) receptor 2 | 10511779 | ATPase, H+ transporting, lysosomal V0 subunit D2 | 10511363 | preproenkephalin | 10548409 | killer cell lectin-like receptor subfamily C, member 1 | Cd27 | CD27 antigen |
| 10523717 | secreted phosphoprotein 1 | 10345762 | interleukin 1 receptor, type I | 10497878 | interleukin 2 | 10421737 | tumor necrosis factor (ligand) superfamily, member 11 | Sell | selectin, lymphocyte |
| 10420308 | granzyme B | 10359697 | chemokine (C motif) ligand 1 | 10385912 | colony stimulating factor 2 (granulocyte-macrophage) | 10597420 | chemokine (C-C motif) receptor 4 | Ctsw | cathepsin W |
| 10545135 | interleukin 12 receptor, beta 2 | 10587639 | 5' nucleotidase, ecto | 10404422 | serine (or cysteine) peptidase inhibitor, clade B, member 6b | 10441633 | chemokine (C-C motif) receptor 6 | Ltb | lymphotoxin B |
| 10531724 | placenta-specific 8 | 10501860 | formin binding protein 1-like | 10408689 | neuritin 1 | 10365933 | early endosome antigen 1 | Gngt2 | guanine nucleotide binding protein (G protein), gamma transducing activity polypeptide 2 /// ABI gene family, member 3 |
| 10363070 | glycoprotein 49 A /// leukocyte immunoglobulin-like receptor, subfamily B, member 4 | 10345032 | interleukin 17A | 10467979 | stearoyl-Coenzyme A desaturase 1 | 10404840 | CD83 antigen | Gpr18 | G protein-coupled receptor 18 |
| 10363082 | leukocyte immunoglobulin-like receptor, subfamily B, member 4 | 10446965 | RAS, guanyl releasing protein 3 | 10469312 | phosphotriesterase related /// C1q-like 3 | 10359434 | Fas ligand (TNF superfamily, member 6) | Igfbp4 | insulin-like growth factor binding protein 4 |
| 10424683 | lymphocyte antigen 6 complex, locus G | 10565990 | ADP-ribosyltransferase 2a | 10435704 | CD80 antigen | 10344966 | lymphocyte antigen 96 | Il17ra | interleukin 17 receptor A |
| 10552406 | natural killer cell group 7 sequence | 10465059 | cathepsin W | 10502655 | cysteine rich protein 61 | 10345752 | interleukin 1 receptor, type II | Il18r1 | interleukin 18 receptor 1 |

TABLE 1-continued

Summary of genes differentially expressed in T_H1, T_H17, and T_H-GM cells

| Genes differentially expressed in T_H1 | | Genes differentially expressed in T_H17 | | Genes differentially upregulated in T_H-GM cells | | Genes upregulated on T_H-GM surface | | Genes downregulated on T_H-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| 10603151 | glycoprotein m6b | 10358476 | proteoglycan 4 (megakaryocyte stimulating factor, articular superficial zone protein) | 10350159 | ladinin | 10439527 | T cell immunoreceptor with Ig and ITIM domains | Klrd1 | killer cell lectin-like receptor, subfamily D, member 1 |
| 10360173 | SLAM family member 7 | 10471953 | activin receptor IIA | 10548409 | killer cell lectin-like receptor subfamily C, member 1 | 10494595 | Notch gene homolog 2 (Drosophila) | Mctp2 | multiple C2 domains, transmembrane 2 |
| 10455961 | interferon inducible GTPase 1 | 10400006 | aryl-hydrocarbon receptor | 10571399 | zinc finger, DHHC domain containing 2 | 10597279 | chemokine (C-C motif) receptor-like 2 | Ms4a6b | membrane-spanning 4-domains, subfamily A, member 6B |
| 10400304 | EGL nine homolog 3 (C. elegans) | 10409876 | cytotoxic T lymphocyte-associated protein 2 alpha | 10538791 | TNFAIP3 interacting protein 3 | 10485405 | CD44 antigen | Pld3 | phospholipase D family, member 3 |
| 10574023 | metallothionein 2 | 10388591 | carboxypeptidase D | 10407126 | polo-like kinase 2 (Drosophila) | 10561104 | AXL receptor tyrosine kinase | Pyhin1 | pyrin and HIN domain family, member 1 |
| 10493108 | cellular retinoic acid binding protein II | 10390640 | IKAROS family zinc finger 3 | 10355984 | serine (or cysteine) peptidase inhibitor, clade E, member 2 | 10585048 | cell adhesion molecule 1 | S1pr1 | sphingosine-1-phosphate receptor 1 |
| 10375436 | family with sequence similarity 71, member B | 10590623 | chemokine (C-X-C motif) receptor 6 | 10421737 | tumor necrosis factor (ligand) superfamily, member 11 | | | Slc44a2 | solute carrier family 44, member 2 |
| 10398039 | serine (or cysteine) peptidase inhibitor, clade A, member 3F /// serine (or cysteine) peptidase inhibitor, clade A, member 3G | 10367734 | uronyl-2-sulfotransferase | 10503023 | cystathionase (cystathionine gamma-lyase) | | | | |
| 10349108 | serine (or cysteine) peptidase inhibitor, clade B, member 5 | 10500656 | CD101 antigen | 10389207 | chemokine (C-C motif) ligand 5 | | | | |
| 10607738 | carbonic anhydrase 5b, mitochondrial | 10347895 | WD repeat domain 69 | 10361887 | PERP, TP53 apoptosis effector | | | | |
| 10496539 | guanylate binding protein 5 | 10495854 | protease, serine, 12 neurotrypsin (motopsin) | 10530841 | insulin-like growth factor binding protein 7 | | | | |

TABLE 1-continued

Summary of genes differentially expressed in $T_H1$, $T_H17$, and $T_H$-GM cells

| Genes differentially expressed in $T_H1$ | | Genes differentially expressed in $T_H17$ | | Genes differentially upregulated in $T_H$-GM cells | | Genes upregulated on $T_H$-GM surface | | Genes downregulated on $T_H$-GM cells surface | |
| --- | --- | --- | --- | --- | --- | --- | --- | --- | --- |
| Gene ID | Gene Title | Gene ID | Gene Title | Gene ID | Gene Title | Gene ID | Gene Title | Gene Symbol | Gene Title |
| 10373918 | leukemia inhibitory factor | 10425049 | apolipoprotein L9b /// apolipoprotein L9a | 10504838 | nuclear receptor subfamily 4, group A, member 3 | | | | |
| 10455954 | predicted gene 4951 | 10378286 | integrin alpha E, epithelial-associated | 10482762 | isopentenyl-diphosphate delta isomerase | | | | |
| 10598976 | tissue inhibitor of metalloproteinase 1 | 10362896 | CD24a antigen | 10597420 | chemokine (C-C motif) receptor 4 | | | | |
| 10492136 | doublecortin-like kinase 1 | 10409866 | cytotoxic T lymphocyte-associated protein 2 beta | 10441633 | chemokine (C-C motif) receptor 6 | | | | |
| 10405211 | growth arrest and DNA-damage-inducible 45 gamma | 10400989 | potassium voltage-gated channel, subfamily H (eag-related), member 5 | 10595402 | family with sequence similarity 46, member A | | | | |
| 10503202 | chromodomain helicase DNA binding protein 7 | 10590242 | chemokine (C-C motif) receptor 8 | 10480139 | C1q-like 3 /// phosphotriesterase related | | | | |
| 10542275 | ets variant gene 6 (TEL oncogene) | 10407435 | aldo-keto reductase family 1, member C18 | 10540472 | basic helix-loop-helix family, member e40 | | | | |
| 10556820 | transmembrane protein 159 | 10592023 | amyloid beta (A4) precursor-like protein 2 | 10404429 | serine (or cysteine) peptidase inhibitor, clade B, member 9 | | | | |
| 10444291 | histocompatibility 2, class II antigen A, beta 1 | 10359480 | dynamin 3 | 10595404 | family with sequence similarity 46, member A | | | | |
| 10439299 | stefin A3 | 10475544 | sema domain, transmembrane domain (TM), and cytoplasmic domain, (semaphorin) 6D | 10365933 | early endosome antigen 1 | | | | |
| 10547641 | solute carrier family 2 (facilitated glucose transporter), member 3 | 10409767 | golgi membrane protein 1 | 10384373 | fidgetin-like 1 | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
| --- | --- | --- | --- | --- | --- | --- | --- | --- | --- |
| Gene ID | Gene Title | Gene ID | Gene Title | Gene ID | Gene Title | Gene ID | Gene Title | Gene Symbol | Gene Title |
| 10503200 | chromodomain helicase DNA binding protein 7 | 10392464 | family with sequence similarity 20, member A | 10400072 | scinderin | | | | |
| 10544320 | RIKEN cDNA 1810009J06 gene /// predicted gene 2663 | 10504891 | transmembrane protein with EGF-like and two follistatin-like domains 1 | 10377938 | enolase 3, beta muscle | | | | |
| 10503218 | chromodomain helicase DNA binding protein 7 | 10504817 | transforming growth factor, beta receptor I | 10589994 | eomesodermin homolog (Xenopus laevis) | | | | |
| 10503198 | chromodomain helicase DNA binding protein 7 | 10393559 | tissue inhibitor of metalloproteinase 2 | 10404840 | CD83 antigen | | | | |
| 10507594 | solute carrier family 2 (facilitated glucose transporter), member 1 | 10474419 | leucine-rich repeat-containing G protein-coupled receptor 4 | 10485624 | proline rich Gla (G-carboxyglutamic acid) 4 (transmembrane) | | | | |
| 10438626 | ets variant gene 5 | 10456492 | DNA segment, Chr 18, ERATO Doi 653, expressed | 10369102 | predicted gene 9766 | | | | |
| 10390328 | T-box 21 | 10345241 | dystonin | 10505030 | fibronectin type III and SPRY domain containing 1-like | | | | |
| 10574027 | metallothionein 1 | 10471555 | angiopoietin-like 2 | 10606868 | brain expressed gene 1 | | | | |
| 10493820 | S100 calcium binding protein A6 (calcyclin) | 10494821 | tetraspanin 2 | 10501832 | ATP-binding cassette, sub-family D (ALD), member 3 | | | | |
| 10376324 | predicted gene 12250 | 10542355 | epithelial membrane protein 1 | 10457225 | mitogen-activated protein kinase kinase 8 | | | | |
| 10406852 | calponin 3, acidic | 10500295 | pleckstrin homology domain containing, family O member 1 | 10554521 | phosphodiesterase 8A | | | | |
| 10412076 | gem (nuclear organelle) associated protein 8 | 10375402 | a disintegrin and metallopeptidase domain 19 (meltrin beta) | 10446229 | tumor necrosis factor (ligand) superfamily, member 9 | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| 10496555 | guanylate binding protein 1 /// guanylate binding protein 5 | 10484227 | SEC14 and spectrin domains 1 | 10593842 | tetraspanin 3 | | | | |
| 10345074 | centrin 4 | 10472097 | formin-like 2 | 10407211 | phosphatidic acid phosphatase type 2A | | | | |
| 10503194 | chromodomain helicase DNA binding protein 7 | 10587829 | procollagen lysine, 2-oxoglutarate 5-dioxygenase 2 | 10488655 | BCL2-like 1 | | | | |
| 10537561 | RIKEN cDNA 1810009J06 gene /// predicted gene 2663 | 10530536 | tec protein tyrosine kinase | 10470182 | brain expressed myelocytomatosis oncogene | | | | |
| 10439895 | activated leukocyte cell adhesion molecule | 10586700 | RAR-related orphan receptor alpha | 10445977 | Epstein-Barr virus induced gene 3 | | | | |
| 10459772 | lipase, endothelial | 10354191 | ring finger protein 149 | 10587495 | interleukin-1 receptor-associated kinase 1 binding protein 1 | | | | |
| 10439762 | S-adenosylhomocysteine hydrolase | 10438738 | B-cell leukemia/lymphoma 6 | 10419082 | RIKEN cDNA 5730469M10 gene | | | | |
| 10482030 | stomatin | 10347888 | chemokine (C-C motif) ligand 20 | 10472212 | plakophilin 4 | | | | |
| 10459905 | SET binding protein 1 | 10440131 | G protein-coupled receptor 15 | 10487588 | interleukin 1 alpha | | | | |
| 10357833 | ATPase, Ca++ transporting, plasma membrane 4 | 10453057 | cytochrome P450, family 1, subfamily b, polypeptide 1 /// RIKEN cDNA 1700038P13 gene | 10359434 | Fas ligand (TNF superfamily, member 6) | | | | |
| 10475517 | expressed sequence AA467197 /// microRNA 147 | 10542140 | killer cell lectin-like receptor subfamily B member 1F | 10351015 | serine (or cysteine) peptidase inhibitor, clade C (antithrombin), member 1 | | | | |
| 10585778 | sema domain, immunoglobulin domain (Ig), and GPI membrane | 10471880 | microRNA 181b-2 | 10344966 | lymphocyte antigen 96 | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| 10354529 | anchor, (semaphorin) 7A | 10542791 | PTPRF interacting protein, binding protein 1 (liprin beta 1) | 10488415 | cystatin C | | | | |
| 10582275 | solute carrier family 7 (cationic amino acid transporter, y+ system), member 5 | 10583242 | sestrin 3 | 10598771 | monoamine oxidase A | | | | |
| 10576034 | interferon regulatory factor 8 | 10489569 | phospholipid transfer protein /// cathepsin A | 10345752 | interleukin 1 receptor, type II | | | | |
| 10503222 | chromodomain helicase DNA binding protein 7 | 10523297 | cyclin G2 | 10588577 | cytokine inducible SH2-containing protein | | | | |
| 10503220 | chromodomain helicase DNA binding protein 7 | 10381187 | ATPase, H+ transporting, lysosomal V0 subunit A1 | 10439527 | T cell immunoreceptor with Ig and ITIM domains | | | | |
| 10503210 | chromodomain helicase DNA binding protein 7 | 10346651 | bone morphogenic protein receptor, type II (serine/threonine kinase) | 10511258 | family with sequence similarity 132, member A | | | | |
| 10476945 | cystatin F (leukocystatin) | 10490159 | prostate transmembrane protein, androgen induced 1 | 10403584 | nidogen 1 | | | | |
| 10503216 | chromodomain helicase DNA binding protein 7 | 10389581 | yippee-like 2 (Drosophila) | 10399973 | histone deacetylase 9 | | | | |
| 10366983 | transmembrane protein 194 | 10581992 | avian musculoaponeurotic fibrosarcoma (v-maf) AS42 oncogene homolog | 10494595 | Notch gene homolog 2 (Drosophila) | | | | |
| 10495675 | coagulation factor III | 10413250 | cytoplasmic polyadenylated homeobox | 10346168 | signal transducer and activator of transcription 4 | | | | |
| 10421697 | RIKEN cDNA 9030625A04 gene | 10555063 | integrator complex subunit 4 | 10350630 | family with sequence | | | | |

TABLE 1-continued

Summary of genes differentially expressed in T<sub>H</sub>1, T<sub>H</sub>17, and T<sub>H</sub>-GM cells

| Genes differentially expressed in T<sub>H</sub>1 | | Genes differentially expressed in T<sub>H</sub>17 | | Genes differentially upregulated in T<sub>H</sub>-GM cells | | Genes upregulated on T<sub>H</sub>-GM surface | | Genes downregulated on T<sub>H</sub>-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| 10445112 | ubiquitin D | 10406982 | a disintegrin-like and metallopeptidase (reprolysin type) with thrombospondin type 1 motif, 6 | 10564667 | similarity 129, member A neurotrophic tyrosine kinase, receptor, type 3 | | | | |
| 10530627 | leucine rich repeat containing 66 | 10596303 | acid phosphatase, prostate | 10419288 | GTP cyclohydrolase 1 | | | | |
| 10440019 | transmembrane protein 45a | 10357472 | chemokine (C-X-C motif) receptor 4 | 10407535 | ribosomal protein L10A /// ribosomal protein L10A, pseudogene 2 | | | | |
| 10378783 | ribosomal protein L36 | 10545130 | growth arrest and DNA-damage-inducible 45 alpha | 10468945 | acyl-Coenzyme A binding domain containing 7 | | | | |
| 10447341 | ras homolog gene family, member Q | 10436402 | claudin domain containing 1 | 10435271 | HEG homolog 1 (zebrafish) | | | | |
| 10373452 | phosphatidylinositol glycan anchor biosynthesis, class F predicted gene 129 | 10539135 | capping protein (actin filament), gelsolin-like | 10576639 | neuropilin 1 | | | | |
| 10454286 | microtubule-associated protein, RP/EB family, member 2 | 10428534 | trichorhinophalan-geal syndrome I (human) | 10505059 | T-cell acute lymphocytic leukemia 2 | | | | |
| 10572497 | interleukin 12 receptor, beta 1 | 10368675 | myristoylated alanine rich protein kinase C substrate | 10457091 | neuropilin (NRP) and tolloid (TLL)-like 1 | | | | |
| 10368060 | epithelial cell transforming sequence 2 oncogene-like | 10531910 | hydroxysteroid (17-beta) dehydrogenase 13 | 10428081 | heat-responsive protein 12 | | | | |
| 10471457 | ST6 (alpha-N-acetyl-neuraminyl-2,3-beta-galactosyl-1,3)-N-acetylgalactosaminide | 10370303 | adenosine deaminase, RNA-specific, B1 | 10435712 | CD80 antigen | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| 10374366 | alpha-2,6-sialyltransferase 4 | 10592888 | epidermal growth factor receptor | 10597279 | chemokine (C-C motif) receptor-like 2 | | | | |
| 10450501 | tumor necrosis factor | 10503259 | transformation related protein 53 inducible nuclear protein 1 | 10485405 | CD44 antigen | | | | |
| 10347291 | chemokine (C-X-C motif) receptor 2 | 10466771 | lysocardiolipin acyltransferase 1 | 10436662 | microRNA 155 | | | | |
| 10553501 | solute carrier family 17 (sodium-dependent inorganic phosphate cotransporter), member 6 | 10428579 | exostoses (multiple) 1 | 10562044 | zinc finger and BTB domain containing 32 | | | | |
| 10345824 | interleukin 18 receptor accessory protein | 10476314 | prion protein | 10463599 | nuclear factor of kappa light polypeptide gene enhancer in B-cells 2, p49/p100 | | | | |
| 10458314 | transmembrane protein 173 | 10406598 | serine incorporator 5 | 10456005 | CD74 antigen (invariant polypeptide of major histocompatibility complex, class II antigen-associated) | | | | |
| 10388430 | serine (or cysteine) peptidase inhibitor, clade F, member 1 | 10461765 | leupaxin | 10490903 | carbonic anhydrase 13 | | | | |
| 10496015 | phospholipase A2, group XIIA | 10428536 | trichorhinophalangeal syndrome I (human) | 10468762 | RIKEN cDNA 4930506M07 gene | | | | |
| 10510391 | spermidine synthase | 10362245 | erythrocyte protein band 4.1-like 2 | 10470316 | na | | | | |
| 10486396 | EH-domain containing 4 | 10604008 | predicted gene 10058 /// predicted gene 10230 /// predicted gene 10486 /// | 10363195 | heat shock factor 2 | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
|  |  |  | predicted gene 14632 /// predicted gene 14819 /// predicted gene 4836 /// predicted gene 2012 /// predicted gene 5169 /// predicted gene 6121 /// Sycp3 like X-linked /// predicted gene 5168 /// predicted gene 10488 /// predicted gene 14525 /// predicted gene 5935 |  |  |  |  |  |  |
| 10368054 | epithelial cell transforming sequence 2 oncogene-like | 10409857 | RIKEN cDNA 4930486L24 gene | 10596652 | HemK methyltransferase family member 1 |  |  |  |  |
| 10608637 | na | 10522368 | NIPA-like domain containing 1 | 10435693 | cytochrome c oxidase, subunit XVII assembly protein homolog (yeast) |  |  |  |  |
| 10595718 | carbohydrate sulfotransferase 2 | 10368720 | solute carrier family 16 (monocarboxylic acid transporters), member 10 | 10544660 | oxysterol binding protein-like 3 |  |  |  |  |
| 10496580 | guanylate binding protein 3 | 10438639 | diacylglycerol kinase, gamma | 10384725 | reticuloendotheliosis oncogene |  |  |  |  |
| 10594053 | promyelocytic leukemia | 10499431 | synaptotagmin XI | 10408600 | serine (or cysteine) peptidase inhibitor, clade B, member 6a |  |  |  |  |
| 10544829 | JAZF zinc finger 1 | 10565840 | neuraminidase 3 | 10391444 | RUN domain containing 1 /// RIKEN cDNA 1700113I22 gene |  |  |  |  |

TABLE 1-continued

Summary of genes differentially expressed in $T_H1$, $T_H17$, and $T_H$-GM cells

| Genes differentially expressed in $T_H1$ | | Genes differentially expressed in $T_H17$ | | Genes differentially upregulated in $T_H$-GM cells | | Genes upregulated on $T_H$-GM surface | | Genes downregulated on $T_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| 10601778 | armadillo repeat containing, X-linked 3 | 10494023 | RAR-related orphan receptor gamma | 10561516 | nuclear factor of kappa light polypeptide gene enhancer in B-cells inhibitor, beta | | | | |
| 10355967 | adaptor-related protein complex AP-1, sigma 3 | 10391103 | junction plakoglobin | 10566846 | DENN/MADD domain containing 5A | | | | |
| 10592503 | cytotoxic and regulatory T cell molecule | 10417053 | muscleblind-like 2 | 10435048 | Tctex1 domain containing 2 | | | | |
| 10496023 | caspase 6 | 10350341 | microRNA 181b-1 | 10470175 | lipocalin 13 | | | | |
| 10599192 | LON peptidase N-terminal domain and ring finger 3 | 10459071 | RIKEN cDNA 2010002N04 gene | 10586250 | DENN/MADD domain containing 4A | | | | |
| 10467578 | phosphoinositide-3-kinase adaptor protein 1 | 10463476 | Kazal-type serine peptidase inhibitor domain 1 | 10512774 | coronin, actin binding protein 2A | | | | |
| 10585703 | ribonuclease P 25 subunit (human) | 10348537 | receptor (calcitonin) activity modifying protein 1 | 10366546 | carboxypeptidase M | | | | |
| 10365482 | tissue inhibitor of metalloproteinase 3 | 10348432 | ArfGAP with GTPase domain, ankyrin repeat and PH domain 1 | 10354286 | KDEL (Lys-Asp-Glu-Leu) containing 1 | | | | |
| 10469151 | inter-alpha (globulin) inhibitor H5 | 10576332 | tubulin, beta 3 /// melanocortin 1 receptor | 10547621 | apolipoprotein B mRNA editing enzyme, catalytic polypeptide 1 | | | | |
| 10503192 | chromodomain helicase DNA binding protein 7 | 10554094 | insulin-like growth factor I receptor | 10440419 | B-cell translocation gene 3 /// B-cell translocation gene 3 pseudogene | | | | |
| 10593050 | interleukin 10 receptor, alpha | 10495794 | phosphodiesterase 5A, cGMP-specific | 10407467 | aldo-keto reductase family 1, member E1 | | | | |
| 10597648 | myeloid differentiation primary response gene 88 | 10569504 | tumor necrosis factor receptor superfamily, member 23 | 10558580 | undifferentiated embryonic cell transcription factor 1 | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| 10538290 | sorting nexin 10 | 10452516 | ankyrin repeat domain 12 | 10544644 | na | | | | |
| 10503204 | chromodomain helicase DNA binding protein 7 | 10534596 | cut-like homeobox 1 | 10424543 | WNT1 inducible signaling pathway protein 1 | | | | |
| 10353707 | protein tyrosine phosphatase 4a1 /// protein tyrosine phosphatase 4a1-like | 10362073 | serum/glucocorticoid regulated kinase 1 | 10507137 | PDZK1 interacting protein 1 | | | | |
| 10377010 | SCO cytochrome oxidase deficient homolog 1 (yeast) | 10408331 | acyl-CoA thioesterase 13 | 10384691 | RIKEN cDNA 0610010F05 gene | | | | |
| 10440903 | RIKEN cDNA 493243BH23 gene | 10415413 | NYN domain and retroviral integrase containing | 10565315 | fumarylacetoacetate hydrolase | | | | |
| 10521205 | SH3-domain binding protein 2 | 10598359 | synaptophysin | 10586248 | DENN/MADD domain containing 4A | | | | |
| 10604587 | microRNA 363 | 10544114 | homeodomain interacting protein kinase 2 | 10561104 | AXL receptor tyrosine kinase | | | | |
| 10571958 | SH3 domain containing ring finger 1 | 10436128 | myosin, heavy chain 15 | 10385837 | interleukin 13 | | | | |
| 10357553 | interleukin 24 | 10408450 | SRY-box containing gene 4 | 10440393 | SAM domain, SH3 domain and nuclear localization signals, 1 | | | | |
| 10606730 | armadillo repeat containing, X-linked 6 | 10487011 | glycine amidinotransferase (L-arginine:glycine amidinotransferase) | 10401987 | potassium channel, subfamily K, member 10 | | | | |
| 10564960 | furin (paired basic amino acid cleaving enzyme) | 10378833 | slingshot homolog 2 (Drosophila) | 10453715 | RAB18, member RAS oncogene family | | | | |
| 10402585 | tryptophanyl-tRNA synthetase | 10521498 | collapsin response mediator protein 1 | 10496466 | alcohol dehydrogenase 4 (class II), pi polypeptide | | | | |
| 10417095 | FERM, RhoGEF (Arhgef) and | 10538939 | eukaryotic translation | 10396712 | fucosyltransferase 8 | | | | |

TABLE 1-continued

Summary of genes differentially expressed in T_H1, T_H17, and T_H-GM cells

| Genes differentially expressed in T_H1 | | Genes differentially expressed in T_H17 | | Genes differentially upregulated in T_H-GM cells | | Genes upregulated on T_H-GM surface | | Genes downregulated on T_H-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| | | | initiation factor 2 alpha kinase 3 | | | | | | |
| 10442435 | pleckstrin domain protein 1 (chondrocyte-derived) | 10585276 | ribonucleic acid binding protein S1 | 10603708 | calcium/calmodulin-dependent serine protein kinase (MAGUK family) | | | | |
| 10394990 | membrane bound O-acyltransferase domain containing 2 | 10512156 | POU domain, class 2, associating factor 1 | 10352178 | saccharopine dehydrogenase (putative) /// similar to Saccharopine dehydrogenase (putative) | | | | |
| 10538753 | atonal homolog 1 (Drosophila) | 10469110 | aquaporin 3 | 10349081 | PH domain and leucine rich repeat protein phosphatase 1 | | | | |
| 10351667 | signaling lymphocytic activation molecule family member 1 | 10568392 | USP6 N-terminal like | 10364950 | growth arrest and DNA-damage-inducible 45 beta | | | | |
| 10461844 | guanine nucleotide binding protein, alpha q polypeptide | 10603346 | regulator of G-protein signalling 10 | 10566877 | SET binding factor 2 | | | | |
| 10422057 | ribosomal protein L7A | 10353947 | proteolipid protein 2 | 10575160 | nuclear factor of activated T-cells 5 | | | | |
| 10572897 | heme oxygenase (decycling) 1 | 10452633 | transmembrane protein 131 | 10458090 | receptor accessory protein 5 | | | | |
| 10507784 | palmitoyl-protein thioesterase 1 | 10380289 | TGFB-induced factor homeobox 1 | 10439845 | predicted gene 5486 | | | | |
| 10445702 | ubiquitin specific peptidase 49 | 10521969 | monocyte to macrophage differentiation-associated | 10461558 | solute carrier family 15, member 3 | | | | |
| 10569057 | ribonuclease/ angiogenin inhibitor 1 | 10521678 | IMP1 inner mitochondrial membrane peptidase-like (S. cerevisiae) | 10586254 | DENN/MADD domain containing 4A | | | | |
| | | | CD38 antigen | | | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| 10370471 | 1-acylglycerol-3-phosphate O-acyltransferase 3 | 10592515 | ubiquitin associated and SH3 domain containing, B | 10574166 | copine II | | | | |
| 10586591 | carbonic anyhydrase 12 | 10512470 | CD72 antigen | 10598467 | proviral integration site 2 | | | | |
| 10512701 | translocase of outer mitochondrial membrane 5 homolog (yeast) | 10587085 | cDNA sequence BC031353 | 10447084 | galactose mutarotase | | | | |
| 10462702 | HECT domain containing 2 | 10492689 | platelet-derived growth factor, C polypeptide | 10366346 | pleckstrin homology-like domain, family A, member 1 | | | | |
| 10552740 | nucleoporin 62 /// Nup62-Il4i1 protein | 10514221 | perilipin 2 | 10355567 | transmembrane BAX inhibitor motif containing 1 | | | | |
| 10581996 | chromodomain protein, Y chromosome-like 2 | 10458247 | leucine rich repeat transmembrane neuronal 2 | 10407420 | neuroepithelial cell transforming gene 1 | | | | |
| 10363901 | ets variant gene 5 | 10468898 | lymphocyte transmembrane adaptor 1 | 10411882 | neurolysin (metallopeptidase M3 family) | | | | |
| 10520862 | fos-like antigen 2 | 10555059 | potassium channel tetramerisation domain containing 14 | 10585048 | cell adhesion molecule 1 | | | | |
| 10526520 | procollagen-lysine, 2-oxoglutarate 5-dioxygenase 3 | 10408629 | RIKEN cDNA 1300014I06 gene | 10538890 | hypothetical protein LOC641050 | | | | |
| 10571274 | glutathione reductase | 10546510 | leucine-rich repeats and immunoglobulin-like domains 1 | 10406681 | adaptor-related protein complex 3, beta 1 subunit | | | | |
| 10351206 | selectin, platelet | 10544596 | transmembrane protein 176B | 10455647 | tumor necrosis factor, alpha-induced protein 8 | | | | |
| 10493474 | mucin 1, transmembrane | 10361748 | F-box protein 30 | 10447521 | transcription factor B1, mitochondrial /// T-cell lymphoma invasion and metastasis 2 | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| 10370000 | glutathione S-transferase, theta 1 | 10356291 | RIKEN cDNA A530040E14 gene | 10523772 | leucine rich repeat containing 8D | | | | |
| 10500272 | predicted gene 129 | 10581450 | DEAD (Asp-Glu-Ala-Asp) box polypeptide 28 | 10417759 | ubiquitin-conjugating enzyme E2E 2 (UBC4/5 homolog, yeast) | | | | |
| 10452815 | xanthine dehydrogenase | 10414417 | pellino 2 | 10586244 | DENN/MADD domain containing 4A | | | | |
| 10393823 | prolyl 4-hydroxylase, beta polypeptide | 10372528 | potassium large conductance calcium-activated channel, subfamily M, beta member 4 /// RIKEN cDNA 1700058G18 gene | 10436500 | glucan (1,4-alpha-), branching enzyme 1 | | | | |
| 10408280 | leucine rich repeat containing 16A | 10408613 | tubulin, beta 2B | 10556297 | adrenomedullin | | | | |
| 10575685 | nudix (nucleoside diphosphate linked moiety X)-type motif 7 | 10411274 | synaptic vesicle glycoprotein 2c | 10593492 | zinc finger CCCH type containing 12C | | | | |
| 10599174 | interleukin 13 receptor, alpha 1 | 10456357 | phorbol-12-myristate-13-acetate-induced protein 1 | 10373358 | interleukin 23, alpha subunit p19 | | | | |
| 10458940 | zinc finger protein 608 | 10511498 | pleckstrin homology domain containing, family F (with FYVE domain) member 2 | 10358583 | hemicentin 1 | | | | |
| 10476197 | inosine triphosphatase (nucleoside triphosphate pyrophosphatase) | 10402136 | G protein-coupled receptor 68 | 10567995 | nuclear protein 1 | | | | |
| 10419790 | ajuba | 10549990 | vomeronasal 1 receptor, G10 /// vomeronasal 1 receptor Vmn1r-ps4 /// vomeronasal 1 | 10512030 | RIKEN cDNA 3110043O21 gene | | | | |

TABLE 1-continued

Summary of genes differentially expressed in T_H1, T_H17, and T_H-GM cells

| Genes differentially expressed in T_H1 | | Genes differentially expressed in T_H17 | | Genes differentially upregulated in T_H-GM cells | | Genes upregulated on T_H-GM surface | | Genes downregulated on T_H-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| 10364909 | ornithine decarboxylase antizyme 1 /// ornithine decarboxylase antizyme 1 pseudogene | 10554789 | receptor 3 /// vomeronasal 1 receptor Vmn1r238 /// vomeronasal 1 receptor 2 cathepsin C | 10594652 | lactamase, beta | | | | |
| 10503190 | chromodomain helicase DNA binding protein 7 | 10427928 | triple functional domain (PTPRF interacting) | 10344960 | transmembrane protein 70 | | | | |
| 10516932 | sestrin 2 | 10549162 | ST8 alpha-N-acetyl-neuraminide alpha-2,8-sialyltransferase 1 | 10399908 | protein kinase, cAMP dependent regulatory, type II beta | | | | |
| 10585338 | KDEL (Lys-Asp-Glu-Leu) containing 2 | 10482109 | mitochondrial ribosome recycling factor /// RNA binding motif protein 18 | 10605766 | melanoma antigen, family D, 1 | | | | |
| 10464425 | G protein-coupled receptor kinase 5 | 10425092 | cytohesin 4 | 10474141 | solute carrier family 1 (glial high affinity glutamate transporter), member 2 | | | | |
| 10441601 | T-cell activation Rho GTPase-activating protein | 10356866 | programmed cell death 1 | 10461909 | cDNA sequence BC016495 | | | | |
| 10482059 | galactosyltransferase alpha 1,3 | 10554204 | ATP/GTP binding protein-like 1 | 10548030 | CD9 antigen | | | | |
| 10522411 | cell wall biogenesis 43 C-terminal homolog (S. cerevisiae) | 10403229 | integrin beta 8 | 10525473 | transmembrane protein 120B | | | | |
| 10369276 | coiled-coil domain containing 109A | 10374529 | expressed sequence AV249152 | 10435266 | HEG homolog 1 (zebrafish) | | | | |

TABLE 1-continued

Summary of genes differentially expressed in $T_H1$, $T_H17$, and $T_H$-GM cells

| Genes differentially expressed in $T_H1$ | | Genes differentially expressed in $T_H17$ | | Genes differentially upregulated in $T_H$-GM cells | | Genes upregulated on $T_H$-GM surface | | Genes downregulated on $T_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| 10368970 | PR domain containing 1, with ZNF domain | 10565434 | ribosomal protein S13 | 10593483 | ferredoxin 1 | | | | |
| 10369541 | hexokinase 1 | 10431266 | ceramide kinase | 10476569 | RIKEN cDNA 2310003L22 gene | | | | |
| 10374236 | uridine phosphorylase 1 | 10410124 | cathepsin L | 10526718 | sperm motility kinase 3A /// sperm motility kinase 3B /// sperm motility kinase 3C | | | | |
| 10489660 | engulfment and cell motility 2, ced-12 homolog (C. elegans) | 10441003 | runt related transcription factor 1 | 10547613 | ribosomal modification protein rimK-like family member B | | | | |
| 10488797 | peroxisomal membrane protein 4 | 10555303 | phosphoglucomutase 2-like 1 | 10511446 | aspartate-beta-hydroxylase | | | | |
| 10558090 | transforming, acidic coiled-coil containing protein 2 | 10530215 | RIKEN cDNA 1110003E01 gene | 10375137 | potassium large conductance calcium-activated channel, subfamily M, beta member 1 | | | | |
| 10409265 | AU RNA binding protein/enoyl-coenzyme A hydratase | 10480275 | nebulette | 10528154 | predicted gene 6455 /// RIKEN cDNA 4933402N22 gene | | | | |
| 10374364 | thymoma viral proto-oncogene 2 | 10434302 | kelch-like 24 (Drosophila) | 10514173 | ribosomal protein L34 /// predicted gene 10154 /// predicted pseudogene 10086 /// predicted gene 6404 | | | | |
| 10598575 | LanC lantibiotic synthetase component C-like 3 (bacterial) | 10565002 | CREB regulated transcription coactivator 3 | 10586227 | DENN/MADD domain containing 4A | | | | |
| 10439514 | growth associated protein 43 | 10413338 | na | 10402648 | brain protein 44-like | | | | |
| 10497842 | Bardet-Biedl syndrome 7 (human) | 10523670 | AF4/FMR2 family, member 1 | 10575745 | ATM interactor | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| 10462091 | Kruppel-like factor 9 /// predicted gene 9971 | 10478594 | cathepsin A | 10346255 | ORMl-like 1 (*S. cerevisiae*) | | | | |
| 10498024 | solute carrier family 7 (cationic amino acid transporter, y+ system), member 11 | 10514128 | tetratricopeptide repeat domain 39B | 10400405 | nuclear factor of kappa light polypeptide gene enhancer in B-cells inhibitor, alpha | | | | |
| 10483719 | chimerin (chimaerin) 1 | 10535956 | StAR-related lipid transfer (START) domain containing 13 | 10528527 | family with sequence similarity 126, member A | | | | |
| 10606694 | Bruton agammaglobulinemia tyrosine kinase | 10503695 | BTB and CNC homology 2 | 10472738 | DDB1 and CUL4 associated factor 17 | | | | |
| 10443110 | synaptic Ras GTPase activating protein 1 homolog (rat) | 10584334 | sialic acid acetylesterase | 10368534 | nuclear receptor coactivator 7 | | | | |
| 10368062 | epithelial cell transforming sequence 2 oncogene-like | 10502890 | ST6 (alpha-N-acetyl-neuraminyl-2,3-beta-galactosyl-1,3)-N-acetylgalactosaminide alpha-2,6-sialyltransferase 3 | 10407543 | GTP binding protein 4 | | | | |
| 10575693 | vesicle amine transport protein 1 homolog-like (*T. californica*) | 10564467 | leucine rich repeat containing 28 | 10376555 | COP9 (constitutive photomorphogenic) homolog, subunit 3 (*Arabidopsis thaliana*) | | | | |
| 10562897 | zinc finger protein 473 /// vaccinia related kinase 3 | 10345715 | mitogen-activated protein kinase kinase kinase 4 | 10567297 | inositol 1,4,5-triphosphate receptor interacting protein-like 2 | | | | |
| 10373709 | eukaryotic translation initiation factor 4E nuclear import factor 1 | 10568668 | a disintegrin and metallopeptidase domain 12 (meltrin alpha) | 10589886 | RIKEN cDNA 4930520O04 gene | | | | |
| 10487238 | histidine decarboxylase | 10462406 | RIKEN cDNA C030046E11 gene | 10423593 | lysosomal-associated | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| | | | | | protein transmembrane 4B | | | | |
| 10594988 | mitogen-activated protein kinase 6 | 10472649 | myosin IIIB | 10577954 | RAB11 family interacting protein 1 (class I) | | | | |
| 10422436 | dedicator of cytokinesis 9 | 10363894 | inositol polyphosphate multikinase | 10604528 | muscleblind-like 3 (*Drosophila*) | | | | |
| 10459084 | synaptopodin | 10606058 | chemokine (C-X-C motif) receptor 3 | 10432675 | RIKEN cDNA I730030J21 gene | | | | |
| 10567450 | dynein, axonemal, heavy chain 3 | 10439955 | family with sequence similarity 55, member C | 10385747 | PHD finger protein 15 | | | | |
| 10604751 | fibroblast growth factor 13 | 10530615 | OCIA domain containing 2 | 10398240 | echinoderm microtubule associated protein like 1 | | | | |
| 10584827 | myelin protein zero-like 2 | 10528183 | spermatogenesis associated glutamate (E)-rich protein 4d /// spermatogenesis associated glutamate (E)-rich protein 4c /// spermatogenesis associated glutamate (E)-rich protein 4e /// predicted gene 9758 /// RIKEN cDNA 4930572O03 gene /// spermatogenesis associated glutamate (E)-rich protein 7, pseudogene 1 /// predicted gene 7361 | 10511803 | RIKEN cDNA 2610029I01 gene | | | | |

TABLE 1-continued

Summary of genes differentially expressed in $T_H1$, $T_H17$, and $T_H$-GM cells

| Genes differentially expressed in $T_H1$ | | Genes differentially expressed in $T_H17$ | | Genes differentially upregulated in $T_H$-GM cells | | Genes upregulated on $T_H$-GM surface | | Genes downregulated on $T_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| 10473356 | ubiquitin-conjugating enzyme E2L 6 | 10488507 | abhydrolase domain containing 12 | 10466606 | annexin A1 | | | | |
| 10498350 | purinergic receptor P2Y, G-protein coupled, 14 | 10420668 | microRNA 15a | 10520304 | ARP3 actin-related protein 3 homolog B (yeast) | | | | |
| 10497862 | transient receptor potential cation channel, subfamily C, member 3 | 10469951 | ring finger protein 208 | 10425903 | na | | | | |
| 10368056 | epithelial cell transforming sequence 2 oncogene-like | 10501629 | CDC14 cell division cycle 14 homolog A (S. cerevisiae) | 10488709 | RIKEN cDNA 8430427H17 gene | | | | |
| 10425357 | Smith-Magenis syndrome chromosome region, candidate 7-like (human) | 10386789 | Unc-51 like kinase 2 (C. elegans) | 10376096 | acyl-CoA synthetase long-chain family member 6 | | | | |
| 10498952 | guanylate cyclase 1, soluble, alpha 3 | 10401138 | ATPase, H+ transporting, lysosomal VI subunit D | 10429491 | activity regulated cytoskeletal-associated protein | | | | |
| 10548905 | epidermal growth factor receptor pathway substrate 8 | 10554118 | family with sequence similarity 169, member B | 10439710 | pleksktrin homology-like domain, family B, member 2 | | | | |
| 10579703 | calcium homeostasis endoplasmic reticulum protein // RIKEN cDNA 1700030K09 gene | 10603843 | synapsin I | 10467110 | expressed sequence AI747699 | | | | |
| 10404630 | RIO kinase 1 (yeast) | 10575184 | WW domain containing E3 ubiquitin protein ligase 2 | 10536898 | interferon regulatory factor 5 | | | | |
| 10518069 | EF hand domain containing 2 | 10537712 | glutathione S-transferase kappa 1 | 10505044 | fukutin | | | | |
| 10469672 | glutamic acid decarboxylase 2 | 10511541 | dpy-19-like 4 (C. elegans) | 10605370 | membrane protein, palmitoylated | | | | |

TABLE 1-continued

Summary of genes differentially expressed in $T_H1$, $T_H17$, and $T_H$-GM cells

| Genes differentially expressed in $T_H1$ | | Genes differentially expressed in $T_H17$ | | Genes differentially upregulated in $T_H$-GM cells | | Genes upregulated on $T_H$-GM surface | | Genes downregulated on $T_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| 10526941 | RIKEN cDNA D830046C22 gene | 10394816 | predicted gene 9282 | 10363669 | DnaJ (Hsp40) homolog, subfamily C, member 12 | | | | |
| 10567448 | dynein, axonemal, heavy chain 3 | 10587503 | SH3 domain binding glutamic acid-rich protein like 2 | 10496727 | dimethylarginine dimethylaminohydrolase 1 | | | | |
| 10437885 | myosin, heavy polypeptide 11, smooth muscle | 10411359 | proteolipid protein 2 | 10587683 | B-cell leukemia/lymphoma 2 related protein A1a /// B-cell leukemia/lymphoma 2 related protein A1d /// B-cell leukemia/lymphoma 2 related protein A1b /// B-cell leukemia/lymphoma 2 related protein A1c | | | | |
| 10600122 | X-linked lymphocyte-regulated 3B /// X-linked lymphocyte-regulated 3C /// X-linked lymphocyte-regulated 3A | 10579939 | ubiquitin specific peptidase 38 /// predicted gene 9725 | 10458816 | toll-like receptor adaptor molecule 2 | | | | |
| 10587665 | RIKEN cDNA 4930579C12 gene | 10370242 | poly(rC) binding protein 3 | 10513008 | Kruppel-like factor 4 (gut) | | | | |
| | | 10350753 | glutamate-ammonia ligase (glutamine synthetase) | 10550906 | plasminogen activator, urokinase receptor | | | | |
| | | 10456296 | mucosa associated lymphoid tissue lymphoma translocation gene 1 | 10362674 | U3A small nuclear RNA | | | | |

TABLE 1-continued

Summary of genes differentially expressed in $T_H1$, $T_H17$, and $T_H$-GM cells

| Genes differentially expressed in $T_H1$ | | Genes differentially expressed in $T_H17$ | | Genes differentially upregulated in $T_H$-GM cells | | Genes upregulated on $T_H$-GM surface | | Genes downregulated on $T_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| | | 10380571 | guanine nucleotide binding protein (G protein), gamma transducing activity polypeptide 2 /// ABI gene family, member 3 | 10473190 | DnaJ (Hsp40) homolog, subfamily C, member 10 | | | | |
| | | 10369413 | sphingosine phosphate lyase 1 | 10477581 | ribosomal protein L5 | | | | |
| | | 10552276 | ubiquitin-conjugating enzyme E2H /// predicted gene 2058 | 10571774 | aspartylglucosaminidase | | | | |
| | | 10394532 | ubiquitin-conjugating enzyme E2F (putative) /// ubiquitin-conjugating enzyme E2F (putative) pseudogene | 10395356 | anterior gradient homolog 3 (Xenopus laevis) | | | | |
| | | 10556463 | aryl hydrocarbon receptor nuclear translocator-like | 10392440 | solute carrier family 16 (monocarboxylic acid transporters), member 6 | | | | |
| | | 10471994 | kinesin family member 5C | 10352815 | interferon regulatory factor 6 | | | | |
| | | 10395328 | sorting nexin 13 | | | | | | |
| | | 10599348 | glutamate receptor, ionotropic, AMPA3 (alpha 3) | | | | | | |
| | | 10601595 | RIKEN cDNA 3110007F17 gene /// predicted gene 6604 /// predicted gene 5167 /// | | | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| | | | predicted gene 2411 /// predicted gene 14957 | | | | | | |
| | | 10372891 | SLIT-ROBO Rho GTPase activating protein 1 | | | | | | |
| | | 10355024 | islet cell autoantigen 1-like | | | | | | |
| | | 10518147 | podoplanin | | | | | | |
| | | 10473537 | olfactory receptor 1123 | | | | | | |
| | | 10424411 | tumor susceptibility gene 101 | | | | | | |
| | | 10439960 | centrosomal protein 97 | | | | | | |
| | | 10551852 | CAP-GLY domain containing linker protein 3 | | | | | | |
| | | 10599291 | reproductive homeobox 4E /// reproductive homeobox 4G /// reproductive homeobox 4F /// reproductive homeobox 4A /// reproductive homeobox 4C /// reproductive homeobox 4B /// reproductive homeobox 4D | | | | | | |
| | | 10587315 | glutathione S-transferase, alpha 4 | | | | | | |
| | | 10447167 | metastasis associated 3 | | | | | | |
| | | 10480288 | nebulette | | | | | | |
| | | 10491300 | SKI-like | | | | | | |
| | | 10596637 | mitogen-activated protein kinase-activated protein kinase 3 | | | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| | | 10518019 | DNA-damage inducible protein 2 /// regulatory solute carrier protein, family 1, member 1 | | | | | | |
| | | 10384685 | RIKEN cDNA 1700093K21 gene | | | | | | |
| | | 10439483 | Rho GTPase activating protein 31 | | | | | | |
| | | 10353844 | neuralized homolog 3 homolog (Drosophila) | | | | | | |
| | | 10459604 | RIKEN cDNA 4933403F05 gene | | | | | | |
| | | 10488892 | transient receptor potential cation channel, subfamily C, member 4 | | | | | | |
| | | 10542822 | RAB15 effector protein | | | | | | |
| | | 10553354 | neuron navigator 2 | | | | | | |
| | | 10425966 | ataxin 10 | | | | | | |
| | | 10360506 | thymoma viral proto-oncogene 3 | | | | | | |
| | | 10531610 | RasGEF domain family, member 1B | | | | | | |
| | | 10417787 | guanine nucleotide binding protein (G protein), gamma 2 | | | | | | |
| | | 10381588 | granulin | | | | | | |
| | | 10437080 | tetratricopeptide repeat domain 3 | | | | | | |
| | | 10509560 | ribosomal protein L38 | | | | | | |
| | | 10466886 | na | | | | | | |
| | | 10580457 | NEDD4 binding protein 1 | | | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| | | 10451061 | runt related transcription factor 2 | | | | | | |
| | | 10433953 | yippee-like 1 (Drosophila) | | | | | | |
| | | 10447461 | stonin 1 | | | | | | |
| | | 10501909 | methyltransferase like 14 /// Sec24 related gene family, member D (S. cerevisiae) | | | | | | |
| | | 10519693 | sema domain, immunoglobulin domain (Ig), short basic domain, secreted, (semaphorin) 3D | | | | | | |
| | | 10385557 | CCR4-NOT transcription complex, subunit 6 | | | | | | |
| | | 10413047 | plasminogen activator, urokinase | | | | | | |
| | | 10406663 | arylsulfatase B | | | | | | |
| | | 10430113 | Rho GTPase activating protein 39 | | | | | | |
| | | 10475830 | mitochondrial ribosomal protein S5 | | | | | | |
| | | 10410892 | RAS p21 protein activator 1 | | | | | | |
| | | 10515994 | stromal membrane-associated GTPase-activating protein 2 | | | | | | |
| | | 10410099 | CDC14 cell division cycle 14 homolog B (S. cerevisiae) | | | | | | |
| | | 10428157 | ring finger protein 19A | | | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| | | 10563643 | tumor susceptibility gene 101 | | | | | | |
| | | 10412260 | follistatin /// thyroid hormone receptor associated protein 3 | | | | | | |
| | | 10386539 | similar to ubiquitin A-52 residue ribosomal protein fusion product 1 | | | | | | |
| | | 10415574 | cyclin I | | | | | | |
| | | 10494978 | protein tyrosine phosphatase, non-receptor type 22 (lymphoid) | | | | | | |
| | | 10511416 | thymocyte selection-associated high mobility group box | | | | | | |
| | | 10562500 | dpy-19-like 3 (C. elegans) | | | | | | |
| | | 10568135 | proline-rich transmembrane protein 2 /// RIKEN cDNA 2900092E17 gene | | | | | | |
| | | 10514466 | Jun oncogene | | | | | | |
| | | 10500847 | membrane associated guanylate kinase, WW and PDZ domain containing 3 | | | | | | |
| | | 10549760 | zinc finger protein 580 | | | | | | |
| | | 10549377 | RIKEN cDNA 1700034J05 gene | | | | | | |
| | | 10430174 | apolipoprotein L9a /// apolipoprotein L9b | | | | | | |

TABLE 1-continued

Summary of genes differentially expressed in T_H1, T_H17, and T_H-GM cells

| Genes differentially expressed in T_H1 | | Genes differentially expressed in T_H17 | | Genes differentially upregulated in T_H-GM cells | | Genes upregulated on T_H-GM surface | | Genes downregulated on T_H-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| | | 10474333 | elongation protein 4 homolog (S. cerevisiae) | | | | | | |
| | | 10560791 | predicted gene, EG381936 /// predicted gene 6176 | | | | | | |
| | | 10407159 | ankyrin repeat domain 55 | | | | | | |
| | | 10603659 | mediator complex subunit 14 | | | | | | |
| | | 10576854 | cortexin 1 | | | | | | |
| | | 10353775 | BEN domain containing 6 | | | | | | |
| | | 10573865 | predicted gene 3579 | | | | | | |
| | | 10356886 | solute carrier organic anion transporter family, member 4C1 | | | | | | |
| | | 10507273 | phosphatidylinositol 3 kinase, regulatory subunit, polypeptide 3 (p55) | | | | | | |
| | | 10424252 | WDYHV motif containing 1 | | | | | | |
| | | 10518735 | sp1A/ryanodine receptor domain and SOCS box containing 1 | | | | | | |
| | | 10562576 | pleckstrin homology domain containing, family F (with FYVE domain) member 1 | | | | | | |
| | | 10375667 | ring finger protein 130 | | | | | | |
| | | 10528268 | protein tyrosine phosphatase, non-receptor type 12 | | | | | | |
| | | 10593205 | REX2, RNA exonuclease 2 | | | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| | | 10576056 | homolog (*S. cerevisiae*) microtubule-associated protein 1 light chain 3 beta | | | | | | |
| | | 10547916 | parathymosin | | | | | | |
| | | 10377689 | gamma-aminobutyric acid receptor associated protein | | | | | | |
| | | 10602307 | ovary testis transcribed /// predicted gene 15085 /// predicted gene 15127 /// predicted gene, OTTMUSG00000019001 /// leucine zipper protein 4 /// predicted gene 15097 /// predicted gene 15091 /// predicted gene 10439 /// predicted gene 15128 | | | | | | |
| | | 10426835 | DIP2 disco-interacting protein 2 homolog B (*Drosophila*) | | | | | | |
| | | 10439798 | DAZ interacting protein 3, zinc finger | | | | | | |
| | | 10375614 | glutamine fructose-6-phosphate transaminase 2 | | | | | | |
| | | 10361882 | NHS-like 1 | | | | | | |
| | | 10419274 | glia maturation factor, beta | | | | | | |
| | | 10424781 | glutamate receptor, ionotropic, N- | | | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| | | | methyl D-aspartate-associated protein 1 (glutamate binding) | | | | | | |
| | | 10546960 | na | | | | | | |
| | | 10514713 | WD repeat domain 78 | | | | | | |
| | | 10394954 | grainyhead-like 1 (Drosophila) | | | | | | |
| | | 10437205 | Purkinje cell protein 4 | | | | | | |
| | | 10464251 | attractin like 1 | | | | | | |
| | | 10496251 | 3-hydroxybutyrate dehydrogenase, type 2 | | | | | | |
| | | 10396383 | solute carrier family 38, member 6 | | | | | | |
| | | 10585794 | cytochrome P450, family 11, subfamily a, polypeptide 1 | | | | | | |
| | | 10385719 | Sec24 related gene family, member A (S. cerevisiae) | | | | | | |
| | | 10407358 | polyadenylate binding protein-interacting protein 1 | | | | | | |
| | | 10498775 | golgi integral membrane protein 4 | | | | | | |
| | | 10584435 | von Willebrand factor A domain containing 5A | | | | | | |
| | | 10466304 | deltex 4 homolog (Drosophila) | | | | | | |
| | | 10598292 | forkhead box P3 /// RIKEN cDNA 4930524L23 gene /// coiled-coil domain containing 22 | | | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| | | 10472440 | Tax1 (human T-cell leukemia virus type I) binding protein 3 | | | | | | |
| | | 10398455 | protein phosphatase 2, regulatory subunit B (B56), gamma isoform | | | | | | |
| | | 10493076 | SH2 domain protein 2A | | | | | | |
| | | 10409152 | RIKEN cDNA 1110007C09 gene | | | | | | |
| | | 10542880 | RIKEN cDNA 4833442119 gene | | | | | | |
| | | 10378523 | Smg-6 homolog, nonsense mediated mRNA decay factor (*C. elegans*) | | | | | | |
| | | 10531560 | anthrax toxin receptor 2 | | | | | | |
| | | 10467319 | retinol binding protein 4, plasma | | | | | | |
| | | 10395978 | predicted gene 527 | | | | | | |
| | | 10471715 | mitochondrial ribosome recycling factor | | | | | | |
| | | 10511755 | WW domain containing E3 ubiquitin protein ligase 1 | | | | | | |
| | | 10353754 | zinc finger protein 451 | | | | | | |
| | | 10477572 | chromatin modifying protein 4B | | | | | | |
| | | 10359161 | sterol O-acyltransferase 1 | | | | | | |
| | | 10462035 | lactate dehydrogenase B | | | | | | |
| | | 10543319 | family with sequence similarity 3, member C | | | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| | | 10579052 | predicted gene 10033 | | | | | | |
| | | 10475532 | sulfide quinone reductase-like (yeast) | | | | | | |
| | | 10428857 | metastasis suppressor 1 | | | | | | |
| | | 10475144 | calpain 3 /// glucosidase, alpha; neutral C | | | | | | |
| | | 10396645 | zinc finger and BTB domain containing 1 | | | | | | |
| | | 10428302 | Kruppel-like factor 10 | | | | | | |
| | | 10577882 | heparan-alpha-glucosaminide N-acetyltransferase | | | | | | |
| | | 10548069 | dual-specificity tyrosine-(Y)-phosphorylation regulated kinase 4 | | | | | | |
| | | 10436053 | developmental pluripotency associated 2 | | | | | | |
| | | 10401564 | RIKEN cDNA 1110018G07 gene | | | | | | |
| | | 10471535 | family with sequence similarity 129, member B | | | | | | |
| | | 10349404 | mannoside acetylglucosaminyltransferase 5 | | | | | | |
| | | 10520173 | amiloride-sensitive cation channel 3 | | | | | | |
| | | 10508860 | solute carrier family 9 (sodium/hydrogen exchanger), member 1 | | | | | | |
| | | 10374500 | vacuolar protein sorting 54 (yeast) | | | | | | |
| | | 10387723 | RIKEN cDNA 2810408A11 gene | | | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| | | 10488020 | thioredoxin-related transmembrane protein 4 | | | | | | |
| | | 10411126 | junction-mediating and regulatory protein | | | | | | |
| | | 10345706 | DNA segment, Chr 1, Brigham & Women's Genetics 0212 expressed | | | | | | |
| | | 10364375 | cystatin B | | | | | | |
| | | 10480379 | mitochondrial ribosomal protein S5 | | | | | | |
| | | 10521243 | G protein-coupled receptor kinase 4 | | | | | | |
| | | 10497920 | ankyrin repeat domain 50 | | | | | | |
| | | 10593723 | acyl-CoA synthetase bubblegum family member 1 | | | | | | |
| | | 10375634 | mitogen-activated protein kinase 9 | | | | | | |
| | | 10384555 | aftiphilin | | | | | | |
| | | 10468113 | Kv channel-interacting protein 2 | | | | | | |
| | | 10423363 | progressive ankylosis | | | | | | |
| | | 10538150 | transmembrane protein 176 A | | | | | | |
| | | 10396485 | synaptic nuclear envelope 2 | | | | | | |
| | | 10401007 | protein phosphatase 2, regulatory subunit B (B56), epsilon isoform | | | | | | |
| | | 10419151 | eosinophil-associated, ribonuclease A family, member 1 | | | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| | | 10390768 | SWI/SNF related, matrix associated, actin dependent regulator of chromatin, subfamily e, member 1 | | | | | | |
| | | 10478145 | protein phosphatase 1, regulatory (inhibitor) subunit 16B | | | | | | |
| | | 10433057 | calcium binding and coiled coil domain 1 | | | | | | |
| | | 10545921 | MAX dimerization protein 1 | | | | | | |
| | | 10392449 | WD repeat domain, phosphoinositide interacting 1 | | | | | | |
| | | 10545608 | sema domain, immunoglobulin domain (Ig), TM domain, and short cytoplasmic domain | | | | | | |
| | | 10567219 | ADP-ribosylation factor-like 6 interacting protein 1 | | | | | | |
| | | 10471201 | c-abl oncogene 1, receptor tyrosine kinase | | | | | | |
| | | 10505841 | predicted gene 13271 /// predicted gene 13290 /// predicted gene 13277 /// predicted gene 13276 | | | | | | |
| | | 10414360 | lectin, galactose binding, soluble 3 | | | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| | | 10403258 | guanosine diphosphate (GDP) dissociation inhibitor 2 | | | | | | |
| | | 10476759 | Ras and Rab interactor 2 | | | | | | |
| | | 10430866 | cytochrome P450, family 2, subfamily d, polypeptide 10 | | | | | | |
| | | 10432619 | POU domain, class 6, transcription factor 1 | | | | | | |
| | | 10521972 | protocadherin 7 | | | | | | |
| | | 10350646 | ER degradation enhancer, mannosidase alpha-like 3 | | | | | | |
| | | 10440993 | regulator of calcineurin 1 | | | | | | |
| | | 10505008 | solute carrier family 44, member 1 | | | | | | |
| | | 10566670 | olfactory receptor 478 | | | | | | |
| | | 10356172 | phosphotyrosine interaction domain containing 1 | | | | | | |
| | | 10418506 | stabilin 1 | | | | | | |
| | | 10419429 | olfactory receptor 723 /// olfactory receptor 724 | | | | | | |
| | | 10581434 | dipeptidase 2 | | | | | | |
| | | 10401365 | zinc finger, FYVE domain containing 1 | | | | | | |
| | | 10591188 | olfactory receptor 843 | | | | | | |
| | | 10565846 | signal peptidase complex subunit 2 homolog (S. cerevisiae) | | | | | | |
| | | 10467258 | myoferlin | | | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| | | 10548547 | predicted gene 6600 | | | | | | |
| | | 10523012 | deoxycytidine kinase | | | | | | |
| | | 10348547 | ubiquitin-conjugating enzyme E2F (putative) | | | | | | |
| | | 10483667 | corepressor interacting with RBPJ, 1 | | | | | | |
| | | 10584071 | PR domain containing 10 | | | | | | |
| | | 10585249 | protein phosphatase 2 (formerly 2A), regulatory subunit A (PR 65), beta isoform | | | | | | |
| | | 10546137 | ankyrin repeat and BTB (POZ) domain containing 1 | | | | | | |
| | | 10484720 | olfactory receptor 1166 | | | | | | |
| | | 10571415 | vacuolar protein sorting 37A (yeast) | | | | | | |
| | | 10595189 | solute carrier family 17 (anion/sugar transporter), member 5 | | | | | | |
| | | 10584426 | olfactory receptor 910 | | | | | | |
| | | 10585986 | myosin IXa | | | | | | |
| | | 10401753 | VPS33B interacting protein, apical-basolateral polarity regulator | | | | | | |
| | | 10349793 | dual serine/threonine and tyrosine protein kinase | | | | | | |

TABLE 1-continued

Summary of genes differentially expressed in T$_H$1, T$_H$17, and T$_H$-GM cells

| Genes differentially expressed in T$_H$1 | | Genes differentially expressed in T$_H$17 | | Genes differentially upregulated in T$_H$-GM cells | | Genes upregulated on T$_H$-GM surface | | Genes downregulated on T$_H$-GM cells surface | |
|---|---|---|---|---|---|---|---|---|---|
| Gene ID | Gene Title | Gene ID | Gene Title | Gene ID | Gene Title | Gene ID | Gene Title | Gene Symbol | Gene Title |
| | | 10527528 | SWI/SNF related, matrix associated, actin dependent regulator of chromatin, subfamily e, member 1 | | | | | | |
| | | 10485767 | olfactory receptor 1277 | | | | | | |
| | | 10557459 | mitogen-activated protein kinase 3 | | | | | | |
| | | 10471486 | endoglin | | | | | | |
| | | 10420846 | frizzled homolog 3 (Drosophila) | | | | | | |
| | | 10405849 | olfactory receptor 466 | | | | | | |
| | | 10568691 | RIKEN cDNA A130023I24 gene | | | | | | |
| | | 10351111 | dynamin 3, opposite strand /// microRNA214 /// microRNA 199a-2 | | | | | | |
| | | 10540785 | RIKEN cDNA 6720456B07 gene | | | | | | |
| | | 10540923 | makorin, ring finger protein, 2 | | | | | | |
| | | 10413416 | interleukin 17 receptor D | | | | | | |
| | | 10386636 | ubiquitin specific peptidase 22 | | | | | | |
| | | 10383799 | transcobalamin 2 | | | | | | |

REFERENCES

Afkarian, M., Sedy, J. R., Yang, J., Jacobson, N. G., Cereb, N., Yang, S. Y., Murphy, T. L., and Murphy, K. M. (2002). T-bet is a STAT1-induced regulator of IL-12R expression in naive CD4+ T cells. Nature immunology 3, 549-557.

Ansel, K. M., Djuretic, I., Tanasa, B., and Rao, A. (2006). Regulation of Th2 differentiation and Il4 locus accessibility. Annual review of immunology 24, 607-656.

Baron, J. L., Madri, J. A., Ruddle, N. H., Hashim, G., and Janeway, C. A., Jr. (1993). Surface expression of alpha 4 integrin by CD4 T cells is required for their entry into brain parenchyma. J Exp Med 177, 57-68.

Bell, A. L., Magill, M. K., McKane, W. R., Kirk, F., and Irvine, A. E. (1995). Measurement of colony-stimulating factors in synovial fluid: potential clinical value. Rheumatol Int 14, 177-182.

Berner, B., Akca, D., Jung, T., Muller, G. A., and Reuss-Borst, M. A. (2000). Analysis of Th1 and Th2 cytokines expressing CD4+ and CD8+ T cells in rheumatoid arthritis by flow cytometry. J Rheumatol 27, 1128-1135.

Bettelli, E., Carrier, Y., Gao, W., Korn, T., Strom, T. B., Oukka, M., Weiner, H. L., and Kuchroo, V. K. (2006). Reciprocal developmental pathways for the generation of pathogenic effector TH17 and regulatory T cells. Nature 441, 235-238.

Brustle, A., Heink, S., Huber, M., Rosenplanter, C., Stadelmann, C., Yu, P., Arpaia, E., Mak, T. W., Kamradt, T., and Lohoff, M. (2007). The development of inflammatory T(H)-17 cells requires interferon-regulatory factor 4. Nature immunology 8, 958-966.

Burchill, M. A., Yang, J., Vogtenhuber, C., Blazar, B. R., and Farrar, M. A. (2007). IL-2 receptor beta-dependent STAT5 activation is required for the development of Foxp3+ regulatory T cells. J Immunol 178, 280-290.

Campbell, I. K., Rich, M. J., Bischof, R. J., Dunn, A. R., Grail, D., and Hamilton, J. A. (1998). Protection from collagen-induced arthritis in granulocyte-macrophage colony-stimulating factor-deficient mice. J Immunol 161, 3639-3644.

Campbell, I. K., van Nieuwenhuijze, A., Segura, E., O'Donnell, K., Coghill, E., Hommel, M., Gerondakis, S., Villadangos, J. A., and Wicks, I. P. (2011). Differentiation of inflammatory dendritic cells is mediated by NF-kappaB1-dependent GM-CSF production in CD4 T cells. J Immunol 186, 5468-5477.

Choy, E. H., and Panayi, G. S. (2001). Cytokine pathways and joint inflammation in rheumatoid arthritis. N Engl J Med 344, 907-916.

Codarri, L., Gyulveszi, G., Tosevski, V., Hesske, L., Fontana, A., Magnenat, L., Suter, T., and Becher, B. (2011). RORgammat drives production of the cytokine GM-CSF in helper T cells, which is essential for the effector phase of autoimmune neuroinflammation. Nat Immunol 12, 560-567.

Cook, A. D., Braine, E. L., Campbell, I. K., Rich, M. J., and Hamilton, J. A. (2001). Blockade of collagen-induced arthritis post-onset by antibody to granulocyte-macrophage colony-stimulating factor (GM-CSF): requirement for GM-CSF in the effector phase of disease. Arthritis Res 3, 293-298.

Cope, A. P., Schulze-Koops, H., and Aringer, M. (2007). The central role of T cells in rheumatoid arthritis. Clin Exp Rheumatol 25, S4-11.

Cornish, A. L., Campbell, I. K., McKenzie, B. S., Chatfield, S., and Wicks, I. P. (2009). G-CSF and GM-CSF as therapeutic targets in rheumatoid arthritis. Nat Rev Rheumatol 5, 554-559.

Croxford, A. L., Mair, F., and Becher, B. (2012). IL-23: one cytokine in control of autoimmunity. European journal of immunology 42, 2263-2273.

Cua, D. J., Sherlock, J., Chen, Y., Murphy, C. A., Joyce, B., Seymour, B., Lucian, L., To, W., Kwan, S., Churakova, T., et al. (2003). Interleukin-23 rather than interleukin-12 is the critical cytokine for autoimmune inflammation of the brain. Nature 421, 744-748.

El-Behi, M., Ciric, B., Dai, H., Yan, Y., Cullimore, M., Safavi, F., Zhang, G. X., Dittel, B. N., and Rostami, A. (2011). The encephalitogenicity of T(H)17 cells is dependent on IL-1- and IL-23-induced production of the cytokine GM-CSF. Nat Immunol 12, 568-575.

Gran, B., Zhang, G. X., Yu, S., Li, J., Chen, X. H., Ventura, E. S., Kamoun, M., and Rostami, A. (2002). IL-12p35-deficient mice are susceptible to experimental autoimmune encephalomyelitis: evidence for redundancy in the IL-12 system in the induction of central nervous system autoimmune demyelination. J Immunol 169, 7104-7110.

Gregory, S. G., Schmidt, S., Seth, P., Oksenberg, J. R., Hart, J., Prokop, A., Caillier, S. J., Ban, M., Goris, A., Barcellos, L. F., et al. (2007). Interleukin 7 receptor alpha chain (IL7R) shows allelic and functional association with multiple sclerosis. Nature genetics 39, 1083-1091.

Greter, M., Helft, J., Chow, A., Hashimoto, D., Mortha, A., Agudo-Cantero, J., Bogunovic, M., Gautier, E. L., Miller, J., Leboeuf, M., et al. (2012). GM-CSF controls nonlymphoid tissue dendritic cell homeostasis but is dispensable for the differentiation of inflammatory dendritic cells. Immunity 36, 1031-1046.

Guedez, Y. B., Whittington, K. B., Clayton, J. L., Joosten, L. A., van de Loo, F. A., van den Berg, W. B., and Rosloniec, E. F. (2001). Genetic ablation of interferon-gamma upregulates interleukin-beta expression and enables the elicitation of collagen-induced arthritis in a nonsusceptible mouse strain. Arthritis Rheum 44, 2413-2424.

Gutcher, I., and Becher, B. (2007). APC-derived cytokines and T cell polarization in autoimmune inflammation. J Clin Invest 117, 1119-1127.

Haak, S., Croxford, A. L., Kreymborg, K., Heppner, F. L., Pouly, S., Becher, B., and Waisman, A. (2009). IL-17A and IL-17F do not contribute vitally to autoimmune neuroinflammation in mice. J Clin Invest 119, 61-69.

Hamilton, J. A. (2008). Colony-stimulating factors in inflammation and autoimmunity. Nat Rev Immunol 8, 533-544.

Harrington, L. E., Hatton, R. D., Mangan, P. R., Turner, H., Murphy, T. L., Murphy, K. M., and Weaver, C. T. (2005). Interleukin 17-producing CD4+ effector T cells develop via a lineage distinct from the T helper type 1 and 2 lineages. Nat Immunol 6, 1123-1132.

Hofstetter, H. H., Ibrahim, S. M., Koczan, D., Kruse, N., Weishaupt, A., Toyka, K. V., and Gold, R. (2005). Therapeutic efficacy of IL-17 neutralization in murine experimental autoimmune encephalomyelitis. Cell Immunol 237, 123-130.

Irmler, I. M., Gajda, M., and Brauer, R. (2007). Exacerbation of antigen-induced arthritis in IFN-gamma-deficient mice as a result of unrestricted IL-17 response. J Immunol 179, 6228-6236.

Ivanov, II, McKenzie, B. S., Zhou, L., Tadokoro, C. E., Lepelley, A., Lafaille, J. J., Cua, D. J., and Littman, D. R. (2006). The orphan nuclear receptor RORgammat directs the differentiation program of proinflammatory IL-17+ T helper cells. Cell 126, 1121-1133.

Kaplan, M. H., Schindler, U., Smiley, S. T., and Grusby, M. J. (1996a). Stat6 is required for mediating responses to IL-4 and for development of Th2 cells. Immunity 4, 313-319.

Kaplan, M. H., Sun, Y. L., Hoey, T., and Grusby, M. J. (1996b). Impaired IL-12 responses and enhanced development of Th2 cells in Stat4-deficient mice. Nature 382, 174-177.

Kolaczkowska, E., and Kubes, P. (2013). Neutrophil recruitment and function in health and inflammation. Nat Rev Immunol 13, 159-175.

Komatsu, N., and Takayanagi, H. (2012). Autoimmune arthritis: the interface between the immune system and joints. Adv Immunol 115, 45-71.

Korn, T., Bettelli, E., Gao, W., Awasthi, A., Jager, A., Strom, T. B., Oukka, M., and Kuchroo, V. K. (2007). IL-21 initiates an alternative pathway to induce proinflammatory T(H)17 cells. Nature 448, 484-487.

Langrish, C. L., Chen, Y., Blumenschein, W. M., Mattson, J., Basham, B., Sedgwick, J. D., McClanahan, T., Kastelein, R. A., and Cua, D. J. (2005). IL-23 drives a pathogenic T cell population that induces autoimmune inflammation. J Exp Med 201, 233-240.

Laurence, A., Tato, C. M., Davidson, T. S., Kanno, Y., Chen, Z., Yao, Z., Blank, R. B., Meylan, F., Siegel, R., Hennighausen, L., et al. (2007). Interleukin-2 signaling via STAT5 constrains T helper 17 cell generation. Immunity 26, 371-381.

Lawlor, K. E., Wong, P. K., Campbell, I. K., van Rooijen, N., and Wicks, I. P. (2005). Acute CD4+ T lymphocyte-dependent interleukin-1-driven arthritis selectively requires interleukin-2 and interleukin-4, joint macrophages, granulocyte-macrophage colony-stimulating factor, interleukin-6, and leukemia inhibitory factor. Arthritis Rheum 52, 3749-3754.

Lee, L. F., Logronio, K., Tu, G. H., Zhai, W., Ni, I., Mei, L., Dilley, J., Yu, J., Rajpal, A., Brown, C., et al. (2012). Anti-IL-7 receptor-alpha reverses established type 1 diabetes in nonobese diabetic mice by modulating effector T-cell function. Proc Natl Acad Sci USA 109, 12674-12679.

Leonard, J. P., Waldburger, K. E., and Goldman, S. J. (1995). Prevention of experimental autoimmune encephalomyelitis by antibodies against interleukin 12. J Exp Med 181, 381-386.

Lighvani, A. A., Frucht, D. M., Jankovic, D., Yamane, H., Aliberti, J., Hissong, B. D., Nguyen, B. V., Gadina, M., Sher, A., Paul, W. E., and O'Shea, J. J. (2001). T-bet is rapidly induced by interferon-gamma in lymphoid and myeloid cells. Proc Natl Acad Sci USA 98, 15137-15142.

Liu, X., Lee, Y. S., Yu, C. R., and Egwuagu, C. E. (2008). Loss of STAT3 in CD4+ T cells prevents development of experimental autoimmune diseases. J Immunol 180, 6070-6076.

Lock, C., Hermans, G., Pedotti, R., Brendolan, A., Schadt, E., Garren, H., Langer-Gould, A., Strober, S., Cannella, B., Allard, J., et al. (2002). Gene-microarray analysis of multiple sclerosis lesions yields new targets validated in autoimmune encephalomyelitis. Nat Med 8, 500-508.

Lundmark, F., Duvefelt, K., Iacobaeus, E., Kockum, I., Wallstrom, E., Khademi, M., Oturai, A., Ryder, L. P., Saarela, J., Harbo, H. F., et al. (2007). Variation in interleukin 7 receptor alpha chain (IL7R) influences risk of multiple sclerosis. Nature genetics 39, 1108-1113.

Manoury-Schwartz, B., Chiocchia, G., Bessis, N., Abehsira-Amar, O., Batteux, F., Muller, S., Huang, S., Boissier, M. C., and Fournier, C. (1997). High susceptibility to collagen-induced arthritis in mice lacking IFN-gamma receptors. J Immunol 158, 5501-5506.

McGeachy, M. J., Chen, Y., Tato, C. M., Laurence, A., Joyce-Shaikh, B., Blumenschein, W. M., McClanahan, T. K., O'Shea, J. J., and Cua, D. J. (2009). The interleukin 23 receptor is essential for the terminal differentiation of interleukin 17-producing effector T helper cells in vivo. Nat Immunol 10, 314-324.

McInnes, I. B., and Schett, G. (2007). Cytokines in the pathogenesis of rheumatoid arthritis. Nat Rev Immunol 7, 429-442.

McInnes, I. B., and Schett, G. (2011). The pathogenesis of rheumatoid arthritis. N Engl J Med 365, 2205-2219.

Muller-Ladner, U., Ospelt, C., Gay, S., Distler, O., and Pap, T. (2007). Cells of the synovium in rheumatoid arthritis. Synovial fibroblasts. Arthritis Res Ther 9, 223.

Muller, J., Sperl, B., Reindl, W., Kiessling, A., and Berg, T. (2008). Discovery of chromone-based inhibitors of the transcription factor STAT5. Chembiochem: a European journal of chemical biology 9, 723-727.

Nurieva, R., Yang, X. O., Martinez, G., Zhang, Y., Panopoulos, A. D., Ma, L., Schluns, K., Tian, Q., Watowich, S. S., Jetten, A. M., and Dong, C. (2007). Essential autocrine regulation by IL-21 in the generation of inflammatory T cells. Nature 448, 480-483.

Okada, Y., Wu, D., Trynka, G., Raj, T., Terao, C., Ikari, K., Kochi, Y., Ohmura, K., Suzuki, A., Yoshida, S., et al. (2014). Genetics of rheumatoid arthritis contributes to biology and drug discovery. Nature 506, 376-381.

Pernis, A. B. (2009). Th17 cells in rheumatoid arthritis and systemic lupus erythematosus. J Intern Med 265, 644-652.

Plater-Zyberk, C., Joosten, L. A., Helsen, M. M., Hepp, J., Baeuerle, P. A., and van den Berg, W. B. (2007). GM-CSF neutralisation suppresses inflammation and protects cartilage in acute streptococcal cell wall arthritis of mice. Ann Rheum Dis 66, 452-457.

Ponomarev, E. D., Shriver, L. P., Maresz, K., Pedras-Vasconcelos, J., Verthelyi, D., and Dittel, B. N. (2007). GM-CSF production by autoreactive T cells is required for the activation of microglial cells and the onset of experimental autoimmune encephalomyelitis. J Immunol 178, 39-48.

Reboldi, A., Coisne, C., Baumjohann, D., Benvenuto, F., Bottinelli, D., Lira, S., Uccelli, A., Lanzavecchia, A., Engelhardt, B., and Sallusto, F. (2009). C-C chemokine receptor 6-regulated entry of TH-17 cells into the CNS through the choroid plexus is required for the initiation of EAE. Nat Immunol 10, 514-523.

Segal, B. M., and Shevach, E. M. (1996). IL-12 unmasks latent autoimmune disease in resistant mice. J Exp Med 184, 771-775.

Shimoda, K., van Deursen, J., Sangster, M. Y., Sarawar, S. R., Carson, R. T., Tripp, R. A., Chu, C., Quelle, F. W., Nosaka, T., Vignali, D. A., et al. (1996). Lack of IL-4-induced Th2 response and IgE class switching in mice with disrupted Stat6 gene. Nature 380, 630-633.

Sonderegger, I., Iezzi, G., Maier, R., Schmitz, N., Kurrer, M., and Kopf, M. (2008). GM-CSF mediates autoimmunity by enhancing IL-6-dependent Th17 cell development and survival. J Exp Med 205, 2281-2294.

Steinman, L. (2007). A brief history of T(H)17, the first major revision in the T(H)1/T(H)2 hypothesis of T cell-mediated tissue damage. Nat Med 13, 139-145.

Stritesky, G. L., Yeh, N., and Kaplan, M. H. (2008). IL-23 promotes maintenance but not commitment to the Th17 lineage. J Immunol 181, 5948-5955.

Szabo, S. J., Sullivan, B. M., Stemmann, C., Satoskar, A. R., Sleckman, B. P., and Glimcher, L. H. (2002). Distinct effects of T-bet in TH1 lineage commitment and IFN-gamma production in CD4 and CD8 T cells. Science 295, 338-342.

Takeda, K., Tanaka, T., Shi, W., Matsumoto, M., Minami, M., Kashiwamura, S., Nakanishi, K., Yoshida, N., Kishimoto, T., and Akira, S. (1996). Essential role of Stat6 in IL-4 signalling. Nature 380, 627-630.

Thierfelder, W. E., van Deursen, J. M., Yamamoto, K., Tripp, R. A., Sarawar, S. R., Carson, R. T., Sangster, M. Y., Vignali, D. A., Doherty, P. C., Grosveld, G. C., and Ihle, J. N. (1996). Requirement for Stat4 in interleukin-12-mediated responses of natural killer and T cells. Nature 382, 171-174.

Veldhoen, M., Hirota, K., Westendorf, A. M., Buer, J., Dumoutier, L., Renauld, J. C., and Stockinger, B. (2008). The aryl hydrocarbon receptor links TH17-cell-mediated autoimmunity to environmental toxins. Nature 453, 106-109.

Veldhoen, M., Hocking, R. J., Atkins, C. J., Locksley, R. M., and Stockinger, B. (2006). TGFbeta in the context of an inflammatory cytokine milieu supports de novo differentiation of IL-17-producing T cells. Immunity 24, 179-189.

Vermeire, K., Heremans, H., Vandeputte, M., Huang, S., Billiau, A., and Matthys, P. (1997). Accelerated collagen-induced arthritis in IFN-gamma receptor-deficient mice. J Immunol 158, 5507-5513.

Willenborg, D. O., Fordham, S., Bernard, C. C., Cowden, W. B., and Ramshaw, I. A. (1996). IFN-gamma plays a critical down-regulatory role in the induction and effector phase of myelin oligodendrocyte glycoprotein-induced autoimmune encephalomyelitis. J Immunol 157, 3223-3227.

Wright, H. L., Moots, R. J., and Edwards, S. W. (2014). The multifactorial role of neutrophils in rheumatoid arthritis. Nat Rev Rheumatol 10, 593-601.

Yamada, H., Nakashima, Y., Okazaki, K., Mawatari, T., Fukushi, J. I., Kaibara, N., Hori, A., Iwamoto, Y., and Yoshikai, Y. (2008). Th1 but not Th17 cells predominate in the joints of patients with rheumatoid arthritis. Ann Rheum Dis 67, 1299-1304.

Yang, X. O., Panopoulos, A. D., Nurieva, R., Chang, S. H., Wang, D., Watowich, S. S., and Dong, C. (2007a). STAT3 regulates cytokine-mediated generation of inflammatory helper T cells. The Journal of biological chemistry 282, 9358-9363.

Yang, X. O., Pappu, B. P., Nurieva, R., Akimzhanov, A., Kang, H. S., Chung, Y., Ma, L., Shah, B., Panopoulos, A. D., Schluns, K. S., et al. (2008). T helper 17 lineage differentiation is programmed by orphan nuclear receptors ROR alpha and ROR gamma. Immunity 28, 29-39.

Yang, X. P., Ghoreschi, K., Steward-Tharp, S. M., Rodriguez-Canales, J., Zhu, J., Grainger, J. R., Hirahara, K., Sun, H. W., Wei, L., Vahedi, G., et al. (2011). Opposing regulation of the locus encoding IL-17 through direct, reciprocal actions of STAT3 and STAT5. Nat Immunol 12, 247-254.

Yang, Y., Ochando, J. C., Bromberg, J. S., and Ding, Y. (2007b). Identification of a distant T-bet enhancer responsive to IL-12/Stat4 and IFNgamma/Stat1 signals. Blood 110, 2494-2500.

Yang, Y. H., and Hamilton, J. A. (2001). Dependence of interleukin-1-induced arthritis on granulocyte-macrophage colony-stimulating factor. Arthritis Rheum 44, 111-119.

Yao, Z., Cui, Y., Watford, W. T., Bream, J. H., Yamaoka, K., Hissong, B. D., Li, D., Durum, S. K., Jiang, Q., Bhandoola, A., et al. (2006). Stat5a/b are essential for normal lymphoid development and differentiation. Proc Natl Acad Sci USA 103, 1000-1005.

Zhang, G. X., Gran, B., Yu, S., Li, J., Siglienti, I., Chen, X., Kamoun, M., and Rostami, A. (2003). Induction of experimental autoimmune encephalomyelitis in IL-12 receptor-beta 2-deficient mice: IL-12 responsiveness is not required in the pathogenesis of inflammatory demyelination in the central nervous system. J Immunol 170, 2153-2160.

Zhou, L., Ivanov, II, Spolski, R., Min, R., Shenderov, K., Egawa, T., Levy, D. E., Leonard, W. J., and Littman, D. R. (2007). IL-6 programs T(H)-17 cell differentiation by promoting sequential engagement of the IL-21 and IL-23 pathways. Nature immunology 8, 967-974.

Zhu, J., and Paul, W. E. (2010). Peripheral CD4+ T-cell differentiation regulated by networks of cytokines and transcription factors. Immunological reviews 238, 247-262.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating an inflammatory disorder in a patient, comprising administering an effective amount of a modulating agent that inhibits Th-GM function,
    wherein the patient exhibits a limited response or no response to a TNF-α inhibitor therapy, wherein the inflammatory disorder is mediated by granulocyte macrophage colony-stimulating factor (GM-CSF)-secreting T-helper (Th-GM) cells
    wherein the modulating agent is a signal transducer and activator of transcription 5 (STAT5) inhibitor, and
    wherein the inflammatory disorder is rheumatoid arthritis.

2. The method of claim 1, wherein the STAT5 inhibitor is an antibody or a small molecule.

3. The method of claim 1, wherein the modulating agent is pimozide or CAS 285986-31-4.

4. The method of claim 1, wherein the patient has an increased expression of STAT5, IL-7, GM-CSF or IL-3 relative to a reference level.

5. The method of claim 1, wherein the $T_H$-GM cells are differentiated from precursor CD4+ cells in the presence of activated STAT5 and IL-7.

6. The method of claim 5, wherein the $T_H$-GM cell expresses GM-CSF and IL-3.

7. The method of claim 5, wherein the $T_H$-GM cells overexpress one or more of basic helix-loop-helix family, member e40 (BHLHe40), preproenkephalin (PENK), IL-2, serine or cysteine peptidase inhibitor, clade B member 6b (Serpinb6b), neuritin 1 (Nrn1), stearoyl-Coenzyme A desaturase 1 (Scd1), and phosphotriesterase related C1q-like 3 (Pter).

8. The method of claim 5, wherein the $T_H$-GM cells underexpress one or more of lymphocyte antigen 6 complex, locus A (Ly6a); CD27; or selectin, lymphocyte (Sell).

9. The method of claim 1, further comprises
contacting a sample collected from the patient who exhibits a limited response or no response to a TNF-α therapy with a detecting agent that detects a polypeptide or nucleic acid level of STAT5, IL-7, GM-CSF or IL-3, or a combination thereof; and
quantifying the polypeptide or nucleic acid level of STAT5, IL-7, GM-CSF or IL-3, or a combination thereof, wherein an increased level of STAT5, IL-7, GM-CSF or IL-3, or a combination thereof relative to a reference level indicates that the patient suffers from the $T_H$-GM-mediated inflammatory disorder.

10. The method of claim 9, further comprising contacting the sample with a detecting agent that detects a polypeptide or nucleic acid level of at least one gene selected from the group consisting of basic helix-loop-helix family member e40 (BHLHE40), Chemokine (C-C Motif) Receptor 4 (CCR4), and Chemokine (C-C Motif) Receptor 6 (CCR6).

11. A method of treating an inflammatory disorder in a patient, comprising administering an effective amount of a modulating agent that inhibits Th-GM function,
wherein the patient exhibits a limited response or no response to a TNF-α inhibitor therapy,
wherein the modulating agent is pimozide, and
wherein the inflammatory disorder is rheumatoid arthritis.

* * * * *